(12) United States Patent
Talasaz

(10) Patent No.: US 10,457,995 B2
(45) Date of Patent: *Oct. 29, 2019

(54) SYSTEMS AND METHODS TO DETECT RARE MUTATIONS AND COPY NUMBER VARIATION

(71) Applicant: Guardant Health, Inc., Redwood City, CA (US)

(72) Inventor: AmirAli Talasaz, Menlo Park, CA (US)

(73) Assignee: GUARDANT HEALTH, INC., Redwood City, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/872,831

(22) Filed: Jan. 16, 2018

(65) Prior Publication Data

US 2018/0223374 A1 Aug. 9, 2018

Related U.S. Application Data

(63) Continuation of application No. 15/828,099, filed on Nov. 30, 2017, which is a continuation of application No. 15/467,570, filed on Mar. 23, 2017, now Pat. No. 9,840,743, which is a continuation of application No. 14/425,189, filed as application No. PCT/US2013/058061 on Sep. 4, 2013, now Pat. No. 10,041,127.

(60) Provisional application No. 61/845,987, filed on Jul. 13, 2013, provisional application No. 61/793,997, filed on Mar. 15, 2013, provisional application No. 61/704,400, filed on Sep. 21, 2012, provisional application No. 61/696,734, filed on Sep. 4, 2012.

(51) Int. Cl.
| | | |
|---|---|---|
| *C12P 19/34* | (2006.01) | |
| *C12Q 1/6886* | (2018.01) | |
| *G16B 30/00* | (2019.01) | |
| *C12Q 1/6869* | (2018.01) | |
| *C12N 15/10* | (2006.01) | |
| *C12Q 1/6806* | (2018.01) | |
| *C12Q 1/6874* | (2018.01) | |

(52) U.S. Cl.
CPC ....... *C12Q 1/6886* (2013.01); *C12N 15/1065* (2013.01); *C12Q 1/6806* (2013.01); *C12Q 1/6869* (2013.01); *C12Q 1/6874* (2013.01); *G16B 30/00* (2019.02); *C12Q 2600/118* (2013.01); *C12Q 2600/156* (2013.01); *C12Q 2600/158* (2013.01); *C12Q 2600/16* (2013.01)

(58) Field of Classification Search
None
See application file for complete search history.

(56) References Cited

U.S. PATENT DOCUMENTS

| | | |
|---|---|---|
| 4,725,536 A | 2/1988 | Fritsch et al. |
| 4,942,124 A | 7/1990 | Church |
| 5,124,246 A | 6/1992 | Urdea et al. |
| 5,149,625 A | 9/1992 | Church et al. |
| 5,200,314 A | 4/1993 | Urdea |
| 5,424,186 A | 6/1995 | Fodor et al. |
| 5,424,413 A | 6/1995 | Hogan et al. |
| 5,445,934 A | 8/1995 | Fodor et al. |
| 5,604,097 A | 2/1997 | Brenner |
| 5,635,352 A | 6/1997 | Urdea et al. |
| 5,635,400 A | 6/1997 | Brenner |
| 5,648,245 A | 7/1997 | Fire et al. |
| 5,654,413 A | 8/1997 | Brenner |
| 5,656,731 A | 8/1997 | Urdea |
| 5,658,737 A | 8/1997 | Nelson et al. |
| 5,714,330 A | 2/1998 | Brenner et al. |
| 5,744,305 A | 4/1998 | Fodor et al. |
| 5,759,778 A | 6/1998 | Li et al. |
| 5,763,175 A | 6/1998 | Brenner |
| 5,800,992 A | 9/1998 | Fodor et al. |
| 5,846,719 A | 12/1998 | Brenner et al. |
| 5,854,033 A | 12/1998 | Lizardi |
| 5,871,928 A | 2/1999 | Fodor et al. |
| 5,925,525 A | 7/1999 | Fodor et al. |
| 5,935,793 A | 8/1999 | Wong |
| 5,952,170 A | 9/1999 | Stroun et al. |
| 5,968,740 A | 10/1999 | Fodor et al. |
| 5,981,176 A | 11/1999 | Wallace |
| 5,981,179 A | 11/1999 | Lorinez et al. |
| 6,013,445 A | 1/2000 | Albrecht et al. |
| 6,020,124 A | 2/2000 | Sorenson |
| 6,040,138 A | 3/2000 | Lockhart et al. |
| 6,046,005 A | 4/2000 | Ju et al. |

(Continued)

FOREIGN PATENT DOCUMENTS

| | | |
|---|---|---|
| CN | 102933721 A | 2/2013 |
| EP | 0799897 B1 | 6/2006 |

(Continued)

OTHER PUBLICATIONS

Leung, et al. Plasma Epstein-Barr viral deoxyribonucleic acid quantitation complements tumor-node-metastasis staging prognostication in nasopharyngeal carcinoma. J Clin Oncol. Dec. 1, 2006;24(34):5414-8.

(Continued)

*Primary Examiner* — Kenneth R Horlick
(74) *Attorney, Agent, or Firm* — Timothy A. Holt

(57) ABSTRACT

The present disclosure provides a system and method for the detection of rare mutations and copy number variations in cell free polynucleotides. Generally, the systems and methods comprise sample preparation, or the extraction and isolation of cell free polynucleotide sequences from a bodily fluid; subsequent sequencing of cell free polynucleotides by techniques known in the art; and application of bioinformatics tools to detect rare mutations and copy number variations as compared to a reference. The systems and methods also may contain a database or collection of different rare mutations or copy number variation profiles of different diseases, to be used as additional references in aiding detection of rare mutations, copy number variation profiling or general genetic profiling of a disease.

26 Claims, 16 Drawing Sheets

(56) References Cited

U.S. PATENT DOCUMENTS

| | | |
|---|---|---|
| 6,060,596 A | 5/2000 | Lerner et al. |
| 6,117,631 A | 9/2000 | Nilsen |
| 6,124,092 A | 9/2000 | O'Neill et al. |
| 6,138,077 A | 10/2000 | Brenner |
| 6,140,489 A | 10/2000 | Brenner |
| 6,172,214 B1 | 1/2001 | Brenner |
| 6,197,506 B1 | 3/2001 | Fodor et al. |
| 6,235,475 B1 | 5/2001 | Brenner et al. |
| 6,242,186 B1 | 6/2001 | Salonen |
| 6,268,152 B1 | 7/2001 | Fodor et al. |
| 6,284,460 B1 | 9/2001 | Fodor et al. |
| 6,300,077 B1 | 10/2001 | Shuber et al. |
| 6,309,822 B1 | 10/2001 | Fodor et al. |
| 6,309,823 B1 | 10/2001 | Cronin et al. |
| 6,326,148 B1 | 12/2001 | Pauletti et al. |
| 6,355,431 B1 | 3/2002 | Chee et al. |
| 6,355,432 B1 | 3/2002 | Fodor et al. |
| 6,395,491 B1 | 5/2002 | Fodor et al. |
| 6,406,848 B1 | 6/2002 | Bridgham et al. |
| 6,440,667 B1 | 8/2002 | Fodor et al. |
| 6,440,706 B1 | 8/2002 | Vogelstein et al. |
| 6,451,536 B1 | 9/2002 | Fodor et al. |
| 6,458,530 B1 | 10/2002 | Morris et al. |
| 6,468,744 B1 | 10/2002 | Cronin et al. |
| 6,489,114 B2 | 12/2002 | Laayoun et al. |
| 6,492,121 B2 | 12/2002 | Kurane et al. |
| 6,498,012 B2 | 12/2002 | Laken |
| 6,503,718 B2 | 1/2003 | Shuber et al. |
| 6,512,105 B1 | 1/2003 | Hogan et al. |
| 6,514,699 B1 | 2/2003 | O'Neill et al. |
| 6,544,739 B1 | 4/2003 | Fodor et al. |
| 6,551,784 B2 | 4/2003 | Fodor et al. |
| 6,576,424 B2 | 6/2003 | Fodor et al. |
| 6,582,908 B2 | 6/2003 | Fodor et al. |
| 6,586,177 B1 | 7/2003 | Shuber |
| 6,600,996 B2 | 7/2003 | Webster et al. |
| 6,629,040 B1 | 9/2003 | Goodlett et al. |
| 6,653,077 B1 | 11/2003 | Brenner |
| 6,753,147 B2 | 6/2004 | Vogelstein et al. |
| 6,849,403 B1 | 2/2005 | Shuber |
| 6,849,404 B2 | 2/2005 | Park et al. |
| 6,852,488 B2 | 2/2005 | Fodor et al. |
| 6,858,412 B2 | 2/2005 | Willis et al. |
| 6,964,846 B1 | 11/2005 | Shuber |
| 7,163,789 B2 | 1/2007 | Chen et al. |
| 7,208,275 B2 | 4/2007 | Gocke et al. |
| 7,406,385 B2 | 7/2008 | Sorenson |
| 7,410,764 B2 | 8/2008 | Gocke et al. |
| 7,424,368 B2 | 9/2008 | Huang et al. |
| 7,424,371 B2 | 9/2008 | Kamentsky |
| 7,537,897 B2 | 5/2009 | Brenner et al. |
| 7,700,286 B2 | 4/2010 | Stroun et al. |
| 7,704,687 B2 | 4/2010 | Wang et al. |
| 7,727,720 B2 | 6/2010 | Dhallan |
| 7,803,929 B2 | 9/2010 | Melkonyan et al. |
| 7,811,757 B2 | 10/2010 | Shuber |
| 7,822,555 B2 | 10/2010 | Huang et al. |
| 7,824,889 B2 | 11/2010 | Vogelstein et al. |
| 7,838,647 B2 | 11/2010 | Hahn et al. |
| 7,915,015 B2 | 3/2011 | Vogelstein et al. |
| 7,935,487 B2 | 5/2011 | Gocke et al. |
| 7,937,225 B2 | 5/2011 | Mishra et al. |
| 7,957,913 B2 | 6/2011 | Chinitz et al. |
| 7,972,817 B2 | 7/2011 | Kopreski |
| 7,981,612 B2 | 7/2011 | Shuber et al. |
| 8,094,312 B2 | 1/2012 | Ulmer |
| 8,168,385 B2 | 5/2012 | Brenner |
| 8,195,415 B2 | 6/2012 | Fan et al. |
| 8,209,130 B1 | 6/2012 | Kennedy et al. |
| 8,216,789 B2 | 7/2012 | Disis et al. |
| 8,236,532 B2 | 8/2012 | Ronaghi et al. |
| 8,361,726 B2 | 1/2013 | Gocke et al. |
| 8,383,338 B2 | 2/2013 | Kitzman et al. |
| 8,383,345 B2 | 2/2013 | Shendure et al. |
| 8,455,193 B2 | 6/2013 | Travers et al. |
| 8,470,996 B2 | 6/2013 | Brenner |
| 8,481,292 B2 | 7/2013 | Casbon et al. |
| 8,603,749 B2 | 12/2013 | Gillevet |
| 8,685,678 B2 | 4/2014 | Casbon et al. |
| 8,697,408 B2 | 4/2014 | Kucera et al. |
| 8,704,165 B2 | 4/2014 | Huang |
| 8,715,967 B2 | 5/2014 | Casbon et al. |
| 8,722,368 B2 | 5/2014 | Casbon et al. |
| 8,728,766 B2 | 5/2014 | Casbon et al. |
| 8,741,606 B2 | 5/2014 | Casbon et al. |
| 8,775,092 B2 | 7/2014 | Colwell et al. |
| 8,835,358 B2 | 9/2014 | Fodor et al. |
| 8,865,410 B2 | 10/2014 | Shendure et al. |
| 9,018,365 B2 | 4/2015 | Brenner |
| 9,085,798 B2 | 7/2015 | Chee |
| 9,260,753 B2 | 2/2016 | Xie et al. |
| 9,340,830 B2 | 5/2016 | Lipson et al. |
| 9,376,719 B2 | 6/2016 | Eijk et al. |
| 9,404,156 B2 | 8/2016 | Hicks et al. |
| 9,476,095 B2 | 10/2016 | Vogelstein et al. |
| 9,598,731 B2 | 3/2017 | Talasaz |
| 9,752,188 B2 | 9/2017 | Schmitt et al. |
| 9,834,822 B2 | 12/2017 | Talasaz |
| 9,840,743 B2 | 12/2017 | Talasaz |
| 9,920,366 B2 | 3/2018 | Eltoukhy et al. |
| 2001/0053519 A1 | 12/2001 | Fodor et al. |
| 2002/0072058 A1 | 6/2002 | Voelker et al. |
| 2003/0003490 A1 | 1/2003 | Fan et al. |
| 2003/0049616 A1 | 3/2003 | Brenner et al. |
| 2003/0104436 A1 | 6/2003 | Morris et al. |
| 2003/0152490 A1 | 8/2003 | Trulson et al. |
| 2003/0165978 A1 | 9/2003 | Firth et al. |
| 2003/0186251 A1 | 10/2003 | Dunn et al. |
| 2003/0207300 A1 | 11/2003 | Matray et al. |
| 2004/0096892 A1 | 5/2004 | Wang et al. |
| 2004/0146901 A1 | 7/2004 | Morris et al. |
| 2004/0157243 A1 | 8/2004 | Huang et al. |
| 2004/0209299 A1 | 10/2004 | Pinter et al. |
| 2004/0259118 A1 | 12/2004 | Macevicz |
| 2005/0164241 A1 | 7/2005 | Hahn et al. |
| 2005/0221314 A1 | 10/2005 | Berlin et al. |
| 2005/0250147 A1 | 11/2005 | Macevicz |
| 2006/0035258 A1 | 2/2006 | Tadakamalla et al. |
| 2006/0046258 A1 | 3/2006 | Lapidus et al. |
| 2006/0073506 A1 | 4/2006 | Christians et al. |
| 2006/0211030 A1 | 9/2006 | Brenner |
| 2007/0020640 A1 | 1/2007 | McCloskey et al. |
| 2007/0065823 A1 | 3/2007 | Dressman et al. |
| 2007/0111233 A1 | 5/2007 | Bianchi et al. |
| 2007/0128724 A1 | 6/2007 | Miles et al. |
| 2007/0172839 A1 | 7/2007 | Smith et al. |
| 2007/0172873 A1 | 7/2007 | Brenner et al. |
| 2008/0014146 A1 | 1/2008 | Von Hoff et al. |
| 2008/0124721 A1 | 5/2008 | Fuchs et al. |
| 2008/0161420 A1 | 7/2008 | Shuber |
| 2008/0261204 A1 | 10/2008 | Lexow |
| 2008/0293055 A1 | 11/2008 | Freeman et al. |
| 2009/0029377 A1 | 1/2009 | Lo et al. |
| 2009/0087847 A1 | 4/2009 | Lo et al. |
| 2009/0098547 A1 | 4/2009 | Ghosh |
| 2009/0105959 A1 | 4/2009 | Braverman et al. |
| 2009/0162836 A1 | 6/2009 | Widschwendter |
| 2009/0298075 A1 | 12/2009 | Travers et al. |
| 2009/0298709 A1 | 12/2009 | Ma |
| 2009/0317818 A1 | 12/2009 | Ehrich et al. |
| 2010/0041048 A1 | 2/2010 | Diehl et al. |
| 2010/0062494 A1 | 3/2010 | Church et al. |
| 2010/0069250 A1 | 3/2010 | White, III et al. |
| 2010/0112575 A1 | 5/2010 | Fan et al. |
| 2010/0143932 A1 | 6/2010 | Lapidus |
| 2010/0166744 A1 | 7/2010 | Wong |
| 2010/0196898 A1 | 8/2010 | Sugarbaker et al. |
| 2010/0323348 A1 | 12/2010 | Hamady et al. |
| 2010/0330571 A1 | 12/2010 | Robins et al. |
| 2011/0014607 A1 | 1/2011 | Jirtle et al. |
| 2011/0160078 A1 | 6/2011 | Fodor et al. |
| 2011/0160290 A1 | 6/2011 | Tewari |
| 2011/0171640 A1 | 7/2011 | Bhatt et al. |
| 2011/0177512 A1 | 7/2011 | Shuber |

(56) References Cited

U.S. PATENT DOCUMENTS

| | | |
|---|---|---|
| 2011/0183330 A1 | 7/2011 | Lo et al. |
| 2011/0201507 A1 | 8/2011 | Rava et al. |
| 2011/0230358 A1 | 9/2011 | Rava |
| 2011/0230360 A1 | 9/2011 | Stephan et al. |
| 2011/0245482 A1 | 10/2011 | Hahn et al. |
| 2011/0264376 A1 | 10/2011 | Chinitz et al. |
| 2011/0275084 A1 | 11/2011 | Byron et al. |
| 2011/0281736 A1 | 11/2011 | Drmanac et al. |
| 2011/0319272 A1 | 12/2011 | Fan et al. |
| 2012/0003637 A1 | 1/2012 | Lo et al. |
| 2012/0034685 A1 | 2/2012 | Sparks et al. |
| 2012/0046877 A1 | 2/2012 | Hyland et al. |
| 2012/0053073 A1 | 3/2012 | Kassis |
| 2012/0059594 A1 | 3/2012 | Hatchwell et al. |
| 2012/0065081 A1 | 3/2012 | Chee |
| 2012/0095697 A1 | 4/2012 | Halpern et al. |
| 2012/0100548 A1 | 4/2012 | Rava et al. |
| 2012/0164630 A1 | 6/2012 | Porreca et al. |
| 2012/0165202 A1 | 6/2012 | Porreca et al. |
| 2012/0191367 A1 | 7/2012 | Stuelpnagel et al. |
| 2012/0208706 A1 | 8/2012 | Downing et al. |
| 2012/0214163 A1 | 8/2012 | Sugarbaker et al. |
| 2012/0214678 A1 | 8/2012 | Rava et al. |
| 2012/0220478 A1 | 8/2012 | Shaffer |
| 2012/0231479 A1 | 9/2012 | Puskas et al. |
| 2012/0238464 A1 | 9/2012 | Koi et al. |
| 2012/0270212 A1 | 10/2012 | Rabinowitz et al. |
| 2012/0316074 A1 | 12/2012 | Saxonov |
| 2012/0322681 A1 | 12/2012 | Kung et al. |
| 2013/0005585 A1 | 1/2013 | Anderson et al. |
| 2013/0017958 A1 | 1/2013 | Benz et al. |
| 2013/0022977 A1 | 1/2013 | Lapidus et al. |
| 2013/0029852 A1 | 1/2013 | Rava et al. |
| 2013/0034546 A1 | 2/2013 | Rava et al. |
| 2013/0040824 A1 | 2/2013 | Lo et al. |
| 2013/0053256 A1 | 2/2013 | Hubbell |
| 2013/0060483 A1 | 3/2013 | Struble et al. |
| 2013/0078626 A1 | 3/2013 | Wasserstrom et al. |
| 2013/0085681 A1 | 4/2013 | Deciu et al. |
| 2013/0102485 A1 | 4/2013 | Lee |
| 2013/0102487 A1 | 4/2013 | Gironella et al. |
| 2013/0116127 A1 | 5/2013 | Schuetz et al. |
| 2013/0116130 A1 | 5/2013 | Fu et al. |
| 2013/0122499 A1 | 5/2013 | Morris et al. |
| 2013/0130923 A1 | 5/2013 | Ehrich et al. |
| 2013/0137588 A1 | 5/2013 | Shendure et al. |
| 2013/0143747 A1 | 6/2013 | Gutin et al. |
| 2013/0210643 A1 | 8/2013 | Casbon et al. |
| 2013/0210645 A1 | 8/2013 | Volgelstein et al. |
| 2013/0224743 A1 | 8/2013 | Casbon et al. |
| 2013/0237431 A1 | 9/2013 | Lo et al. |
| 2013/0237458 A1 | 9/2013 | Casbon et al. |
| 2013/0260381 A1 | 10/2013 | Ramakrishnan |
| 2013/0267424 A1 | 10/2013 | Casbon et al. |
| 2013/0338933 A1 | 12/2013 | Deciu et al. |
| 2014/0011694 A1 | 1/2014 | Couronne |
| 2014/0065609 A1 | 3/2014 | Hicks et al. |
| 2014/0065630 A1 | 3/2014 | Von Bubnoff et al. |
| 2014/0066317 A1 | 3/2014 | Talasaz |
| 2014/0100121 A1 | 4/2014 | Lo et al. |
| 2014/0242588 A1 | 8/2014 | Boom et al. |
| 2014/0274731 A1 | 9/2014 | Raymond et al. |
| 2014/0274740 A1 | 9/2014 | Srinivasan et al. |
| 2014/0296094 A1 | 10/2014 | Domanus |
| 2014/0303008 A1 | 10/2014 | Schutz et al. |
| 2014/0336943 A1 | 11/2014 | Pellini et al. |
| 2014/0350130 A1 | 11/2014 | Sanborn et al. |
| 2014/0357500 A1 | 12/2014 | Vigneault et al. |
| 2015/0004158 A1 | 1/2015 | Shipp et al. |
| 2015/0024950 A1 | 1/2015 | Bielas et al. |
| 2015/0044687 A1 | 2/2015 | Schmitt et al. |
| 2015/0050647 A1 | 2/2015 | Luo et al. |
| 2015/0051085 A1 | 2/2015 | Vogelstein et al. |
| 2015/0065358 A1 | 3/2015 | Comstock et al. |
| 2015/0080266 A1 | 3/2015 | Volkmuth et al. |
| 2015/0087535 A1 | 3/2015 | Patel |
| 2015/0167069 A1 | 6/2015 | Schutz et al. |
| 2015/0197786 A1 | 7/2015 | Osborne et al. |
| 2015/0275289 A1 | 10/2015 | Otwinowski et al. |
| 2015/0299812 A1 | 10/2015 | Talasaz |
| 2015/0329917 A1 | 11/2015 | Shuber |
| 2015/0344970 A1 | 12/2015 | Vogelstein et al. |
| 2015/0366866 A1 | 12/2015 | Ali et al. |
| 2015/0368708 A1 | 12/2015 | Talasaz |
| 2016/0002739 A1 | 1/2016 | Schütz et al. |
| 2016/0002741 A1 | 1/2016 | Kitano et al. |
| 2016/0024576 A1 | 1/2016 | Chee |
| 2016/0026758 A1 | 1/2016 | Jabara et al. |
| 2016/0032396 A1 | 2/2016 | Diehn et al. |
| 2016/0040229 A1 | 2/2016 | Talasaz et al. |
| 2016/0046986 A1 | 2/2016 | Eltoukhy et al. |
| 2016/0053301 A1 | 2/2016 | Raymond et al. |
| 2016/0060691 A1 | 3/2016 | Giresi et al. |
| 2016/0071432 A1 | 3/2016 | Kurowski et al. |
| 2016/0115553 A1 | 4/2016 | Stephan et al. |
| 2016/0130649 A1 | 5/2016 | Xie et al. |
| 2016/0251704 A1 | 9/2016 | Talasaz et al. |
| 2016/0319345 A1 | 11/2016 | Gnerre et al. |
| 2016/0333417 A1 | 11/2016 | Talasaz |
| 2016/0376647 A1 | 12/2016 | Travers et al. |
| 2017/0051347 A1 | 2/2017 | Vogelstein et al. |
| 2017/0073774 A1 | 3/2017 | Lo et al. |
| 2017/0145516 A1 | 5/2017 | Kopetz et al. |
| 2017/0159120 A1 | 6/2017 | Eijk et al. |
| 2017/0211143 A1 | 7/2017 | Shendure et al. |
| 2017/0218459 A1 | 8/2017 | Talasaz et al. |
| 2017/0218460 A1 | 8/2017 | Talasaz |
| 2018/0023125 A1 | 1/2018 | Talasaz et al. |

FOREIGN PATENT DOCUMENTS

| | | |
|---|---|---|
| EP | 1647600 A3 | 6/2006 |
| EP | 2110442 A1 | 10/2009 |
| EP | 3070177 A1 | 9/2016 |
| EP | 3178941 A1 | 6/2017 |
| WO | 1997007241 A1 | 2/1997 |
| WO | 1997010365 A1 | 3/1997 |
| WO | 1999028505 A1 | 6/1999 |
| WO | 2000058516 A2 | 10/2000 |
| WO | 2002056014 A2 | 7/2002 |
| WO | 2005080604 A2 | 9/2005 |
| WO | 2005111242 A2 | 11/2005 |
| WO | 2006102264 A1 | 9/2006 |
| WO | 2007037678 A2 | 4/2007 |
| WO | 2008070144 A2 | 6/2008 |
| WO | 2008154317 A1 | 12/2008 |
| WO | 2009152928 A2 | 12/2009 |
| WO | 2009152928 A3 | 2/2010 |
| WO | 2011060240 A1 | 5/2011 |
| WO | 2011087760 A2 | 7/2011 |
| WO | 2011091046 A1 | 7/2011 |
| WO | 2011103236 A2 | 8/2011 |
| WO | 2011140510 A2 | 11/2011 |
| WO | 2011155833 A2 | 12/2011 |
| WO | 2012012693 A2 | 1/2012 |
| WO | 2012014877 A1 | 2/2012 |
| WO | 2012019200 A2 | 2/2012 |
| WO | 2012028746 A1 | 3/2012 |
| WO | 2012042374 A2 | 4/2012 |
| WO | 2012048341 A1 | 4/2012 |
| WO | 2012054873 A2 | 4/2012 |
| WO | 2012066451 A1 | 5/2012 |
| WO | 2012038839 A2 | 6/2012 |
| WO | 2012071621 A1 | 6/2012 |
| WO | 2012088348 A2 | 6/2012 |
| WO | 2012106559 A1 | 8/2012 |
| WO | 2012129363 A2 | 9/2012 |
| WO | 2012142213 A2 | 10/2012 |
| WO | 2012142611 A2 | 10/2012 |
| WO | 2012103031 A3 | 1/2013 |
| WO | 2013019075 A2 | 2/2013 |
| WO | 2013033721 A1 | 3/2013 |
| WO | 2013106737 A1 | 7/2013 |
| WO | 2013123442 A1 | 8/2013 |

(56) References Cited

FOREIGN PATENT DOCUMENTS

| | | |
|---|---|---|
| WO | 2013130512 A2 | 9/2013 |
| WO | 2013130674 A1 | 9/2013 |
| WO | 2013138510 A1 | 9/2013 |
| WO | 2013142213 A1 | 9/2013 |
| WO | 2013142389 A1 | 9/2013 |
| WO | 2013148496 A1 | 10/2013 |
| WO | 2013159035 A2 | 10/2013 |
| WO | 2013173394 A2 | 11/2013 |
| WO | 2013181170 A1 | 12/2013 |
| WO | 2013188471 A2 | 12/2013 |
| WO | 2013190441 A2 | 12/2013 |
| WO | 2014004726 A1 | 1/2014 |
| WO | 2014014497 A1 | 1/2014 |
| WO | 2014015319 A1 | 1/2014 |
| WO | 2014039556 A1 | 3/2014 |
| WO | 2014093330 A1 | 6/2014 |
| WO | 2014145078 A1 | 9/2014 |
| WO | 2014151117 A1 | 9/2014 |
| WO | 2014152990 A1 | 9/2014 |
| WO | 2015159293 A2 | 10/2015 |
| WO | 2016015058 A2 | 1/2016 |
| WO | 2016040901 A1 | 3/2016 |
| WO | 2017100441 A1 | 6/2017 |
| WO | 2017181146 A1 | 10/2017 |

OTHER PUBLICATIONS

Li, et al. Structure-independent and quantitative ligation of single-stranded DNA. Anal Biochem. Feb. 15, 2006;349(2):242-6. Epub Nov. 18, 2005.

Li, H. et al. Mapping short DNA sequencing reads and calling variants using mapping quality scores. Genome Res. Nov. 2008;18(11):1851-8. doi: 10.1101/gr.078212.108. Epub Aug. 19, 2008.

Lizardi, et al. Mutation detection and single-molecule counting using isothermal rolling-circle amplification. Nat Genet. Jul. 1998;19(3):225-32.

Lo, et al. Quantitative analysis of cell-free Epstein-Barr virus DNA in plasma of patients with nasopharyngeal carcinoma. Cancer Res. Mar. 15, 1999;59(6):1188-91.

Lockhart, et al. Expression monitoring by hybridization to high-density oligonucleotide arrays. Nature Biotechnology, 14: 1675-1680 (1996).

Lucito, et al. Detecting gene copy number fluctuations in tumor cells by microarray analysis of genomic representations. Genome Res. Nov. 2000;10(11):1726-36.

Maamar, et al. Noise in Gene Expression Determines Cell Fate in Bacillus subtilis. Science, 317: 526-529 (2007).

Mahmud, et al. Fast MCMC sampling for hidden Markov Models to determine copy number variations. BMC Bioinformatics. Nov. 2, 2011;12:428. doi: 10.1186/1471-2105-12-428.

Makrigiorgos, et al., A PCR-Based amplification method retaining quantative difference between two complex genomes. Nature Biotech, vol. 20, No. 9, pp. 936-939 (Sep. 2002).

Mandel, et al. Les acides nucleiques du plasma sanguin chez 10homme C R Seances Soc Biol Fil. Feb. 1948;142(3-4):241-3.

Marsit, et al. Epigenetic profiling reveals etiologically distinct patterns of DNA methylation in head and neck squamous cell carcinoma. Carcinogenesis. Mar. 2009;30(3):416-22. doi: 10.1093/carcin/bgp006. Epub Jan. 6, 2009.

McCloskey, et al. Encoding PCR products with batch-stamps and barcodes. Biochem Genet. Dec. 2007;45(11-12):761-7. Epub Oct. 23, 2007.

Medvedev, et al. Detecting copy number variation with mated short reads. Genome Res. Nov. 2010;20(11):1613-22. doi: 10.1101/gr.106344.110. Epub Aug. 30, 2010.

Mei, et al. Identification of recurrent regions of Copy-Number Variants across multiple individuals. BMC Bioinformatics. Mar. 22, 2010;11:147. doi: 10.1186/1471-2105-11-147.

Meldrum, et al. Next-Generation Sequencing for Cancer Diagnostics: a Practical Perspective. Clin Biochem Rev. Nov. 2011; 32:177-95.

Milbury, et al. COLD-PCR enrichment of rare cancer mutations prior to targeted amplicon resequencing. Clin Chem. Mar. 2012;58(3):580-9. doi: 10.1373/clinchem.2011.176198. Epub Dec. 21, 2011.

Miner, et al. Molecular barcodes detect redundancy and contamination in hairpin-bisulfite PCR. Nucleic Acids Res. Sep. 30, 2004;32(17):e135.

Mitchell, et al. Circulating microRNAs as stable blood-based markers for cancer detection. Proc Natl Acad Sci U S A. Jul. 29, 2008;105(30):10513-8. doi: 10.1073/pnas.0804549105. Epub Jul. 28, 2008.

Mohan; et al., "Changes in colorectal carcinoma genomes under anti-EGFR therapy identified by whole-genome plasma DNA sequencing.", doi: 10.1371/journal.pgen.1004271. eCollection 2014., Mar. 27, 2014, 10(3), e1004271.

Mori, et al. Predictive utility of circulating methylated DNA in serum of melanoma patients receiving biochemotherapy. J Clin Oncol. Dec. 20, 2005;23(36):9351-8.

Morrissy, A.S. et al. "Next-generation tag sequencing for cancer gene expression profiling" Genome Research (2009) 19(10): 1825-1835.

Mortazavi, et al. Mapping and quantifying mammalian transcriptomes by RNA-Seq. Nat. Methods. 2008; 5, 621-628.

Narayan, et al. Ultrasensitive measurement of hotspot mutations in tumor DNA in blood using error-suppressed multiplexed deep sequencing. Cancer Res. Jul. 15, 2012;72(14):3492-8. doi: 10.1158/0008-5472.CAN-11-4037. Epub May 10, 2012.

Nawroz, et al. Microsatellite alterations in serum DNA of head and neck cancer patients. Nat Met Sep. 1996;2(9):1035-7.

Newman, et al. An ultrasensitive method for quantitating circulating tumor DNA with broad patient coverage. Nat Med. May 2014;20(5):548-54. doi: 10.1038/nm.3519. Epub Apr. 6, 2014.

Nord, et al. Accurate and exact CNV identification from targeted high-throughput sequence data. BMC Genomics. Apr. 12, 2011;12:184. doi: 10.1186/1471-2164-12-184.

Ogino, et al. Quantification of PCR bias caused by a single nucleotide polymorphism in SMN gene dosage analysis. J Mol Diagn. Nov. 2002;4(4):185-90.

Pacific Biosciences. Template Preparation and Sequencing Guide. Publication date: Oct. 14, 2014. Pacific Biosciences website http://www.pacificbiosciences.com/support/pubmap/documentation.html.

Pan, et al. Loss of heterozygosity patterns provide fingerprints for genetic heterogeneity in multistep cancer progression of tobacco smoke-induced non-small cell lung cancer. Cancer Res. Mar. 1, 2005;65(5):1664-9.

Park, et al. Discovery of common Asian copy number variants using integrated high-resolution array CGH and massively parallel DNA sequencing. Nat Genet. May 2010;42(5):400-5. doi: 10.1038/ng.555. Epub Apr. 4, 2010.

Pihlak, et al. Rapid genome sequencing with short universal tiling probes. Nature Biotechnology, 26: 676-684 (2008).

Pinkel, et al. Comparative Genomic Hybridization. Annual Review of Genomics and Human Genetics, 6: 331-354 (2005).

Pleasance, et al. A small-cell lung cancer genome with complex signatures of tobacco exposure. Nature. Jan. 14, 2010;463(7278):184-90. doi: 10.1038/nature08629. Epub Dec. 16, 2009.

Pollack, et al. Genome-wide analysis of DNA copy-number changes using cDNA microarrays. Nat Genet. Sep. 1999;23(1):41-6.

Qiu, et al. DNA sequence-based "bar codes" for tracking the origins of expressed sequence tags from a maize cDNA library constructed using multiple mRNA sources. Plant Physiol. Oct. 2003;133(2):475-81.

Quail, et al. A large genome center's improvements to the Illumina sequencing system. Nat Methods. Dec. 2008;5(12):1005-10. doi: 10.1038/nmeth.1270.

Rand, K.N., et al. Headloop suppression PCR and its application to selective amplification of methylated DNA sequences. Nucleic Acids Res. Aug. 9, 2005;33(14):e127.

(56) References Cited

OTHER PUBLICATIONS

Ryan, et al. A prospective study of circulating mutant KRAS2 in the serum of patients with colorectal neoplasia: strong prognostic indicator in postoperative follow up. Gut. Jan. 2003; 52(1): 101-108.
Rygaard, et al. Abnormalities in structure and expression of the retinoblastoma gene in small cell lung cancer cell lines and xenografts in nude mice. Cancer Res. Sep. 1, 1990;50(17):5312-7.
Schmitt M.W. et al., "Detection of ultra-rare mutations by next-generation sequencing." PNAS, Aug. 1, 2012, 109(36):14508-14513.
Schwarzenbach, et al. A critical evaluation of loss of heterozygosity detected in tumor tissues, blood serum and bone marrow plasma from patients with breast cancer Breast Cancer Res. 2007;9(5):R66.
Schwarzenbach, et al. Cell-free tumor DNA in blood plasma as a marker for circulating tumor cells in prostate cancer. Clin Cancer Res. Feb. 1, 2009;15(3):1032-8. doi: 10.1158/1078-0432.CCR-8-1910.
Sebat, et al. Large-Scale Copy Number Polymorphism in the Human Genome. Science, 305: 525-528 (2004).
Shaw, et al. Genomic analysis of circulating cell-free DNA infers breast cancer dormancy. Genome Res. Feb. 2012;22(2):220-31. doi: 10.1101/gr.123497.111. Epub Oct. 11, 2011.
Shaw, et al. Microsatellite alterations plasma DNA of primary breast cancer patients. Clin Cancer Res. Mar. 2000;6(3):1119-24.
Shinozaki, et al. Utility of circulating B-RAF DNA mutation in serum for monitoring melanoma patients receiving biochemotherapy. Clin Cancer Res. Apr. 1, 2007;13(7):2068-74.
Shiroguchi, et al. Digital RNA sequencing minimizes sequence-dependent bias and amplification noise with optimized single-molecule barcodes, PNAS, Jan. 24, 2012;109(4):1347-52.
Shoemaker, et al. Quantitative phenotypic analysis of yeast deletion mutants using a highly parallel molecular bar-coding strategy. Nature Genetics, 14: 450-456 (1996).
Alkan, et al. "Personalized copy number and segmental duplication maps using next-generation sequencing." Nat Genet. Oct. 2009;41(10):1061-7. doi: 10.1038/ng.437. Epub Aug. 30, 2009.
Andersson, et al. "Bayesian detection of periodic mRNA time profiles without use of training examples." BMC Bioinformatics. Feb. 9, 2006 7:63.
Angeloni, D. Molecular analysis of deletions in human chromosome 3p21 and the role of resident cancer genes in disease. Brief Funct Genomic Proteomic. Mar. 2007 6(1):19-39. Epub May 24, 2007.
Ansorge "Next-generation DNA sequencing techniques." New Biotechnology, 25(4):195-203 (2009).
Appel, Maryke. Part II: It's all about conversion. Kapa Biosystems. Accessed Mar. 29, 2017.Printed Apr. 11, 2017. 5 pages. URL:< https://www.kapabiosytems.com/ngs/part-ii-conversion/.
Ashford, Monica. NGS Error Correction Method Described at AACR as Excitement Grows for Early Cancer Detection. Genomeweb.com. Apr. 5, 2017. 3 pages. URL:.
Atanur, et al. "The genome sequence of the spontaneously hypertensive rat: Analysis and functional significance." Genome Res. Jun. 2010;20(6):791-803. doi: 10.1101/gr.103499.109. Epub Apr. 29, 2010.
Audic, et al. "The Significance of Digital Gene Expression Profiles." Genome Research, 7: 986-995 (1997).
Barzon, et al. "Evaluation of circulating thyroid-specific transcripts as markers of thyroid cancer relapse." Int J Cancer. Jul. 20, 2004 110(6):914-20
Bendich, et al. "Circulating DNA as a possible factor in oncogenesis." Science. Apr. 16, 1965;148(3668):374-6.
Bonaldo, et al. "Normalization and subtraction: two approaches to facilitate gene discovery." Genome Res. Sep. 1996;6(9):791-806.
Bowcock, et al. "Exclusion of the retinoblastoma gene and chromosome 13q as the site of a primary lesion for human breast cancer." Am J Hum Genet. Jan. 1990;46(1):12-17.
Braha, et al. Simultaneous stochastic sensing of divalent metal ions. Nature Biotechnology, 18: 1005-1007 (2000).
Bremnes, et al. "Circulating tumour-derived DNA and RNA markers in blood: a tool for early detection, diagnostics, and follow-up?" Lung Cancer. Jul. 2005;49(1):1-12.
Brenner, et al. "Gene expression analysis by massively parallel signature sequencing (MPSS) on microbead arrays" Nature Biotechnology, 18: 630-634 (2000).
Brenner, et al. "In vitro cloning of complex mixtures of DNA on microbeads: physical separation of differentially expressed cDNAs." Proc Natl Acad Sci U S A. Feb. 15, 2000;97(4):1665-70.
Campbell, et al. "Identification of somatically acquired rearrangements in cancer using genome-wide massively parallel paired-end sequencing." Nat Genet. Jun. 2008;40(6):722-9. doi: 10.1038/ng.128. Epub Apr. 27, 2008.
Caramazza, et al. "Chromosome 1 abnormalities in myeloid malignancies: a literature survey and karyotype-phenotype associations." Eur J Haematol. Mar. 2010;84(3):191-200. doi: 10.1111/j.1600-0609.2009.01392.x. Epub Nov. 30, 2009.
Carr, et al. "Inferring relative proportions of DNA variants from sequencing electropherograms." Bioinformatics. Dec. 15, 2009;25(24):3244-50. doi: 10.1093/bioinformatics/btp583. Epub Oct. 9, 2009.
Casbon, et al. "A method for counting PCR template molecules with application to next-generation sequencing." Nucleic Acids Res. Jul. 2011;39(12):e81. doi: 10.1093/nar/gkr217. Epub Apr. 13, 2011.
Castle, et al. "DNA copy number, including telomeres and mitochondria, assayed using next-generation sequencing." BMC Genomics. Apr. 16, 2010;11:244. doi: 10.1186/1471-2164-11-244.
Chang, et al. "Detection of allelic imbalance in ascitic supernatant by digital single nucleotide polymorphism analysis." Clin Cancer Res. Aug. 2002;8(8):2580-5.
Chee, et al. "Accessing genetic information with high-density DNA arrays." Science, 274: 610-614 (1996).
Chee. "Enzymatic multiplex DNA sequencing." Nucleic Acids Research, 19(12): 3301-3305 (1991).
Chen, et al. "Microsatellite alterations in plasma DNA of small cell lung cancer patients." Nat Med. Sep. 1996;2(9):1033-5.
Chin et al. "A SNP in a let-7 microRNA complementary site in the KRAS 3'UTR Increases Non-Small Cell Lung Cancer Risk" (2008) Cancer Res.68(20):8535-8540. Doi:10.1158/0008-5472.CAN-8-2129.
Chiu, et al. "Non-invasive prenatal assessment of trisomy 21 by multiplexed maternal plasma DNA sequencing: large scale validity study." BMJ. Jan. 11, 2011;342:c7401. doi: 10.1136/bmj.c7401.
Chiu, et al. "Quantitative analysis of circulating mitochondrial DNA in plasma." Clin Chem. May 2003;49(5):719-26.
Church, et al. "Multiplex DNA sequencing." Science, 240: 185-188 (1988).
Cook, et al. "Methylated DNA labels for marking objects." Biotechnol Lett. Jan. 2003;25(1):89-94.
Costello, et al. "Discovery and characterization of artifactual mutations in deep coverage targeted capture sequencing data due to oxidative DNA damage during sample preparation." Nucleic Acids Res. Apr. 1, 2013;41(6): e67. doi: 10.1093/nar/gks1443. Epub Jan. 8, 2013.
Coulet, et al. "Detection of plasma tumor DNA in head and neck squamous cell carcinoma by microsatellite typing and p53 mutation analysis." Cancer Res. Feb. 1, 2000;60(3):707-11.
Cox, J. "Bar coding objects with DNA." Analyst. May 2001;126(5):545-7.
Craig, et al. "Identification of genetic variants using bar-coded multiplexed sequencing." Nat Methods. Oct. 2008;5(10):887-93. doi: 10.1038/nmeth.1251. Epub Sep. 14, 2008.
Daines, et al. "High-throughput multiplex sequencing to discover copy number variants in *Drosophila*." Genetics. Aug. 2009;182(4):935-41. doi: 10.1534/genetics.109.103218. Epub Jun. 15, 2009.
D'Antoni, et al. "Rapid quantitative analysis using a single molecule counting approach." Anal Biochem. May 1, 2006;352(1):97-109. Epub Feb. 10, 2006.
Daser, et al. "Interrogation of genomes by molecular copy-number counting (MCC)." Nature Methods, 3(6): 447-453 (2006).
De Saizieu, et al. "Bacterial transcript imaging by hybridization of total RNA to oligonucleotide arrays." Nature Biotechnology, 16: 45-48 (1998).

(56) References Cited

OTHER PUBLICATIONS

Diehl, et al. "Circulating mutant DNA to assess tumor dynamics." Nat Med. Sep. 2008;14(9):985-90. doi: 10.1038/nm.1789. Epub Jul. 31, 2007.

Diehl, et al. Detection and quantification of mutations in the plasma of patients with colorectal tumors. Proc Natl Acad Sci US A. Nov. 8, 2005;102(45):16368-73. Epub Oct. 28, 2005.

Ding, et al. "Clonal evolution in relapsed acute myeloid leukaemia revealed by whole-genome sequencing." Nature. Jan. 11, 2012;481(7382):506-10. doi: 10.1038/nature10738.

Ehrich et al. "Noninvasive detection of fetal trisomy 21 by sequencing of DNA in maternal blood: a study in a clinical setting." Am J Obstet Gynecol. Mar. 2011;204(3):205.e1-11. doi: 10.1016/j.ajog. 2010.12.060. Epub Feb. 18, 2011.

Eisenmann, et al. "5q-myelodysplastic syndromes: chromosome 5q genes direct a tumor-suppression network sensing actin dynamics." Oncogene. Oct. 1, 2009;28(39):3429-41. doi: 10.1038/onc. 2009207. Epub Jul. 13, 2009.

Elshire et al. "A Robust, Simple Genotyping-by-Sequencing (GBS) Approach for High Diversity Species" (May 4, 2011) PloS ONE 6(5): e 19379. Doi:10.1371/journal.pone.0019379.

Fan, et al. "Microfluidic digital PCR enables rapid prenatal diagnosis of fetal aneuploidy." Am Obstet Gynecol. 2009; 200:541e1-543.e7.

Fan, et al. "Noninvasive diagnosis of fetal aneuploidy by shotgun sequencing DNA from maternal blood." Proc Natl Acad Sci U S A. Oct. 21, 2008;105(42)16266-71. doi: 10.1073/pnas.0808319105. Epub Oct. 6, 2008.

Fan, et al. "Non-invasive prenatal measurement of the fetal genome." Nature. Jul. 19, 2012;487(7407):320-4. doi: 10.1038/nature11251.

Fan, et al. "Parallel Genotyping of Human SNPs Using Generic High-density Oligonucleotide Tag Arrays." Genome Research, 10: 853-860 (2000).

Fonatsch, C. "The role of chromosome 21 in hematology and oncology." Genes Chromosomes Cancer. Jun. 2010;49(6):497-508. doi: 10.1002/gcc.20764.

Forster, et al. "From next-generation sequencing alignments to accurate comparison and validation of single-nucleotide variants: the pibase software." Nucleic Acids Res. Jan. 7, 2013;41(1):e16. doi: 10.1093/nar/gks836. Epub Sep. 10, 2012.

Fournie, et al. "Plasma DNA as a marker of cancerous cell death. Investigations in patients suffering from lung cancer and in nude mice bearing human tumours." Cancer Lett. May 8, 1995;91(2):221-7.

Freeman, J.D. et al. "Profiling the T-cell receptor beta-chain repertoire by massively parallel sequencing." Genome Res. Oct. 2009;19(10):1817-24. doi: 10.1101/gr.092924.109. Epub Jun. 18, 2009.

Fu, et al. "Counting individual DNA molecules by the stochastic attachment of diverse labels." Proc Natl Acad Sci U S A. May 31, 2011;108(22):9026-31. Epub May 11, 2011.

Fujiwara, et al. Identification of epigenetic aberrant promoter methylation in serum DNA is useful for early detection of lung cancer. Clin Cancer Res. Feb. 1, 2005;11(3):1219-25.

Fujiwara, et al. Plasma DNA microsatellites as tumor-specific markers and indicators of tumor progression in melanoma patients. Cancer Res. Apr. 1, 1999;59(7):1567-71.

Gerry, et al. Universal DNA microarray method for multiplex detection of low abundance point mutations. Journal of Molecular Biology, 292(2): 251-262 (1999).

Gillespie. Exact stochastic simulation of coupled chemical reactions. The Journal of Physical Chemistry, 81(25): 2340-2361 (1977).

Gordian, et al. Serum free circulating DNA is a useful biomarker to distinguish benign versus malignant prostate disease. Cancer Epidemiol Biomarkers Prev. Aug. 2010;19(8):1984-91. doi: 10.1158/1055-9965.EPI-10-0287. Epub Jul. 20, 2010.

Gormally, et al. Amount of DNA in plasma and cancer risk: a prospective study. Int J Cancer. Sep. 20, 2004;111(5):746-9.

Grant, et al. SNP genotyping on a genome-wide amplified DOP-PCR template. Nucleic Acids Res. Nov. 15, 2002;30(22):e125.

Grutzmann, et al. Sensitive detection of colorectal cancer in peripheral blood by septin 9 DNA methylation assay. PLoS One. 2008;3(11):e3759. doi: 10.1371/journal.pone.0003759. Epub Nov. 19, 2008.

Gundry, et al. Direct mutation analysis by high-throughput sequencing: from germline to low-abundant, somatic variants. Mutat Res. Jan. 3, 2012;729(1-2):1-15. doi: 10.1016/mrfmmm.2011.10.001. Epub Oct. 12, 2011.

Gundry, et al. Direct, genome-wide assessment of DNA mutations in single cells. Nucleic Acids Res. Mar. 2012;40(5):2032-40. doi: 10.1093/nar/gkr949. Epub Nov. 15, 2011.

Hacia, et al. Determination of ancestral alleles for human single-nucleotide polymorphisms using high-density oligonucleotide arrays. Nature Genetics, 22: 164-167 (1999).

Hafner M. et al. "RNA-ligase-dependent biases in miRNA representation in deep-sequenced small RNA cDNA libraries", RNA, Sep. 1, 2011 (Sep. 1, 2011), 17(9):1697-1712, XP055076478, ISSN: 1355-8382, DOI: 10.1261 /rna.2799511.

Hamady, et al. Error-correcting barcoded primers for pyrosequencing hundreds of samples in multiplex. Nat Methods. Mar. 2008;5(3):235-7. doi: 10.1038/nmeth.1184. Epub Feb. 10, 2008.

Hensel, et al. Simultaneous identification of bacterial virulence genes by negative selection. Science. Jul. 21, 1995;269(5222):400-3.

Hiatt, et al. Parallel, tag-directed assembly of locally derived short sequence reads. Nat Methods. Feb. 2010;7(2):119-22. doi: 10.1038/nmeth.1416. Epub Jan. 17, 2010.

Hiatt, et al. Single molecule molecular inversion probes for targeted, high-accuracy detection of low-frequency variation. Genome Res. May 2013;23(5):843-54. doi: 10.1101/gr.147686.112. Epub Feb. 4, 2013.

Hibi, et al. Molecular detection of genetic alterations in the serum of colorectal cancer patients. Cancer Res. Apr. 1, 1998;58(7):1405-7.

Holdenrieder, et al. Circulating nucleosomes and cytokeratin 19-fragments in patients with colorectal cancer during chemotherapy. Anticancer Res. May-Jun. 2005;25(3A):1795-801.

Holies, et al. A stochastic approach to count RNA molecules using DNA sequencing methods. 2003, Lecture Notes in Computer Science, vol. 2812, pp. 55-62.

Hoque, et al. Detection of aberrant methylation of four genes in plasma DNA for the detection of breast cancer. J Clin Oncol. Sep. 10, 2006;24(26):4262-9. Epub Aug. 14, 2006.

Howe, et al. Retinoblastoma growth suppressor and a 300-kDa protein appear to regulate cellular DNA synthesis.Proc Natl Acad Sci U S A. Aug. 1990;87(15):5883-7.

Hug, et al. Measurement of the number of molecules of a single mRNA species in a complex mRNA preparation. J Theor Biol. Apr. 21, 2003;221(4):615-24.

Hyland, et al. The normal and tumor spectrum of copy number variation: Copy number alterations correlate with changes in gene expression in tumor transcriptome. Nov. 15, 2009. 1page. Retreived from:< https://tools.thermofisher.com/contents/sfs/posters/cms_073633.pdf>.

Iafrate, et al. Detection of large-scale variation in the human genome. Nat Genet. Sep. 2004;36(9):949-51. Epub Aug. 1, 2004.

Ikeguchi, et al. Detection of loss of heterozygosityat microsatellite loci in esophageal squamous-cell carcinoma. Oncology. 1999;56(2)164-8.

Ingolia, et al. Genome-wide analysis in vivo of translation with nucleotide resolution using ribosome profiling. Science. Apr. 10, 2009;324(5924):218-23. Epub Feb. 12, 2009.

Jabara, C. Capturing the cloud: High throughput sequencing of multiple individual genomes from a retroviral population. Biology Lunch Bunch Series, Training Initiatives in Biomedical & Biological Sciences of the University of North Carolina at Chapel Hill, Apr. 23, 2010.

Jabara, et al. Accurate sampling and deep sequencing of the HIV-1 protease gene using a Primer ID. (Paper # 665), The 18th Annual Conference on Retroviruses and Opportunistic Infections, Boston, Massachusetts, Mar. 2011.

(56) References Cited

OTHER PUBLICATIONS

Jabara, et al. Accurate sampling and deep sequencing of the HIV-1 protease gene using a Primer ID. Proc Natl Aced Sci U S A. Dec. 13, 2011;108(50):20166-71. doi: 10.1073/pnas.1110064108. Epub Nov. 30, 2011.
Jahr, et al. DNA fragments in the blood plasma of cancer patients: quantitations and evidence for their origin from apoptotic and necrotic cells. Cancer Res. Feb. 15, 2001;61(4):1659-65.
Jeronimo, et al. Quantitative GSTP1 hypermethylation in bodily fluids of patients with prostate cancer. Urology. Dec. 2002;60(6):1131-5.
Kanagawa. Bias and artifacts in multitemplate polymerase chain reactions (PCR), 2003, Journal of Bioscience and Bioengineering, vol. 96, No. 4, p. 317-323.
Kimura, et al. EGFR mutation status in tumour-derived DNA from pleural effusion fluid is a practical basis for predicting the response to gefitinib. Br J Cancer. Nov. 20, 2006;95(10):1390-5. Epub Oct. 24, 2006.
Kinde, et al. Detection and quantification of rare mutations with massively parallel sequencing. Proc Natl Acad Sci U S A. Jun. 7, 2011;108(23):9530-5. doi: 10.1073/pnas.1105422108. Epub May 17, 2011.
Kivioja, T., et al. Counting absolute numbers of molecules using unique molecular identifiers. Nat Methods. Nov. 20, 2011;9(1):72-4. doi: 10.1038/nmeth.1778.
Koboldt, et al. "Massively parallel sequencing approaches for characterization of structural variation" Methods Mol Biol (Aug. 12, 2011) 838:369-384.
Kolble, et al. Microsatellite alterations in serum DNA of patients with colorectal cancer. Lab Invest. Sep. 1999;79(9):1145-50.
Konig, et al. iCLIP reveals the function of hnRNAP particles in splicing at individual nucleotide resolution, Jul. 2010, Nature Structural & Molecular Biology, 17(7):909-916.
Kopreski, et al. Detection of mutant K-ras DNA in plasma or serum of patients with colorectal cancer. Br J Cancer. 1997;76(10):1293-9.
Koyanagi, et al. Association of circulating tumor cells with serum tumor-related methylated DNA in peripheral blood of melanoma patients. Cancer Res. Jun. 15, 2006;66(12):6111-7.
Lam, et al. Plasma DNA as a prognostic marker for stroke patients with negative neuroimaging within the first 24 h of symptom onset. Resuscitation. Jan. 2006;68(1):71-8. Epub Dec. 1, 2005.
Lanman, et al., Analytical and Clinical Validation of a Digital Sequencing Panel for Quantitative, Highly Accurate Evaluation of Cell-Free Circulating Tumor DNA PLoS One, Oct. 2015, 10(10), webpage, retrieved on Mar. 24, 2017. https://www.ncbi.nlm.nih.gov/pmc/articles/PMC4608804/.
Larson, et al. A single molecule view of of gene expression. Trends Cell Biol. Nov. 2009;19(11):630-7. Epub Oct. 8, 2009.
Leary, et al. Detection of chromosomal alterations in the circulation of cancer patients with whole-genome sequencing. Sci Transl Med. Nov. 28, 2012;4(162):162ra154. doi: 10.1126/scitranslmed.3004742.
Leary, et al. Development of personalized tumor biomarkers using massively parallel sequencing. Sci Transl Med. Feb 24, 2010;2(20):20ra14. doi: 10.1126/scitranslmed.3000702.
Lecomte, et al. Detection of free-circulating tumor-associate DNA in plasma of colorectal cancer patients and its association with prognosis. Int J Cancer. Aug. 10, 2002;100(5):542-8.
Leon, et al. Free DNA in the serum of cancer patients and the effect of therapy. Cancer Res. Mar. 1977;37(3):646-50.
Simpson, et al. Copy number variant detection in inbred strains from short read sequence data. Bioinformatics. Feb. 15, 2010;26(4):565-7. doi: 10.1093/bioinformatics/btp693. Epub Dec. 18, 2009.
Smith, et al. Highly-multiplexed barcode sequencing: an efficient method for parallel analysis of pooled samples. Nucleic Acids Research, 38(13): e142 (2010).
Sorenson, et al. Soluble normal and mutated DNA sequences from single-copy genes in human blood. Cancer Epidemiol Biomarkers Prev. Jan.-Feb. 1994;3(1):67-71.

Sparks et al. "Selective analysis of cell-free DNA in maternal blood for evaluation of fetal trisomy" (Jan. 6, 2012 first on line publication date) DOI: 10.1002/pd.2922. Prenatal Diagnosis (2012) vol. 32: 3-9.
Steinman. Free NA in serum and plasma from normal adults. J Clin Invest. Aug. 1975;56(2):512-5.
Stitziel, et al. Computational and statistical approaches to analyzing variants identified byexome sequencing. Genome Biol. Sep. 14, 2011;12(9):227. doi: 10.1186/gb-2011-12-9-227.
Stroun, et al. About the possible origin and mechanism of circulating DNA apoptosis and active DNA release. Clin Chim Acta. Nov. 2001;313(1-2):139-42.
Taback, et al. Detection of tumor-specific genetic alterations in bone marrow from early-stage breast cancer patients. Cancer Res. Apr. 15, 2003;63(8):1884-7.
Tan, et al. Genome-wide comparison of DNA hydroxymethylation in mouse embryonic stem cells and neural progenitor cells by a new comparative hMeDIP-seq method. Nucleic Acids Res. Apr. 2013;41(7):e84. doi: 10.1093/nar/gkt091. Epub Feb. 13, 2013.
Taudien, et al. Haplotyping and copy number estimation of the highly polymorphic human beta-defensin locus on 8p23 by 454 amplicon sequencing. BMC Genomics. Apr. 19, 2010;11:252. doi: 10.1186/1471-2164-11-252.
Tomaz, et al. Differential methylation as a cause of allele dropout at the imprinted GNAS locus. Genet Test Mol Biomarkers. Aug. 2010;14(4):455-60. doi: 10.1089/gtmb.2010.0029.
Tomlinson et al. (2007) Nature Genetics vol. 39: No. 8 pp. 984-988 doi:10.1038/ng2085.
Tsai, et al. Discovery of rare mutations in populations: Tilling by sequencing. Plant Physiol. Jul. 2011;156(3):1257-68. doi: 10.1104/pp.110.169748. Epub Apr. 29, 2011.
UCSC Genome Bioinformatics. About the UCSC Genome Bioinformatics Site. http://genome.ucsc.edu/index.html. Accessed on May 26, 2015. 2 pgs.
Umetani, et al. Prediction of breast tumor progression by integrity of free circulating DNA in serum. J Clin Oncol. Sep. 10, 2006;24(26):4270-6.
Utting, et al. Microsatellite analysis of free tumor DNA in urine, serum, and plasma of patients: a minimally invasive method for the detection of bladder cancer. Clin Cancer Res. Jan. 2002;8(1):35-40.
Van Houten, et al. Mutated p53 as a molecular marker for the diagnosis of head and neck cancer. J Pathol. Dec. 2002;198(4):476-86.
Velculescu, et al. Characterization of the Yeast Transcriptome. Cell, 88: 243-251 (1997).
Velculescu, et al. Serial Analysis of Gene Expression. Science, 270: 484-487 (1995).
Vogelstein, et al. Digital PCR. Proc. Natl. Acad. Sci., 96(16): 9236-9241 (1999).
Walker, et al. "Isothermal in vitro amplification of DNA by a restriction enzyme/DNA polymerase system." Proc Natl Acad Sci U S A. Jan. 1, 1992;89(1):392-6.
Walsh, et al. Detection of inherited mutations for breast and ovarian cancer using genomic capture and massively parallel sequencing. Proc Natl Acad Sci U S A. Jul. 13, 2010;107(28):12629-33. doi: 10.1073/pnas.1007983107. Epub Jun. 28, 2010.
Wang, et al. iCLIP predicts the dual splicing effects of TIA-RNA interactions, Oct. 2010, PLoS Biol, 8(10):e1000530.
Wang, et al. Molecular detection of APC, K-ras, and p53 mutations in the serum of colorectal cancer patients as circulating biomarkers. World J Surg. Jul. 2004;28(7):721-6. Epub Jun. 8, 2004.
Wang, et al. RNA-Seq: a revolutionary tool for transcriptomics. Nature Reviews Genetics, 10: 57-63 (2009).
Weber, et al. A real-time polymerase chain reaction assay for quantification of allele ratios and correction of amplification bias. Anal Biochem. Sep. 15, 2003;320(2):252-8.
Wines, et al. Searching for Evidence of Altered Gene Expression: a Comment on Statistical Analysis of Microarray Data. Journal of the National Cancer Institute, 91(5): 400-401 (1999).
Wodicka, et al. Genome-wide expression monitoring in *Saccharomyces cerevisiae*. Nature Biotechnology, 15: 1359-1367 (1997).

(56) References Cited

OTHER PUBLICATIONS

Wojdacs, et al. Primer design versus PCR bias in methylation independent PCR amplifications. Epigenetics. May 16, 2009;4(4):231-4. Epub May 14, 2009.
Wood, et al. The genomic landscapes of human breast and colorectal cancers. Science. Nov. 16, 2007;318(5853)1108-13. Epub Oct. 11, 2007.
Wood, et al. Using next-generation sequencing for high resolution multiplex analysis of copy number variation from nanogram quantities of DNA from formalin-fixed paraffin-embedded specimens. Nucleic Acids Res. Aug. 2010;38(14): e151. doi: 10.1093/nar/gkq510. Epub Jun. 4, 2010.
Xi, et al. Copy number variation detection in whole-genome sequencing data using the Bayesian information criterion. Proc Natl Acad Sci U S A. Nov. 15, 2011;108(46):E1128-36. doi: 10.1073/pnas.1110574108. Epub Nov. 7, 2011.
Yandell, et al. A probabilistic disease-gene finder for personal genomes. Genome Res. Sep. 2011;21(9):1529-42. doi: 10.1101/gr.123158.111. Epub Jun. 23, 2011.
Yang. Simple binary segmentation frameworks for identifying variation in DNA copy number. BMC Bioinformatics. Oct. 30, 2012;13:277. doi: 10.1186/1471-2105-13-277.
Yang; et al., "EGFR gene copy number as a predictive biomarker for the treatment of metastatic colorectal cancer with anti-EGFR monoclonal antibodies: a meta-analysis.", Aug. 16, 2012, 5:52, 1-9.
Ye, et al. Fluorescent microsphere-based readout technology for multiplexed human single nucleotide polymorphism analysis and bacterial identification. Human Mutation, 17(4): 305-316 (2001).
Yoon, et al. Sensitive and accurate detection of copy number variants using read depth of coverage. Genome Res. Sep. 2009;19(9):1586-92. doi: 10.1101/gr.092981.109. Epub Aug. 5, 2009.
Zhang, et al. The impact of next-generation sequencing on genomics. J Genet Genomics. Mar. 20, 2011;38(3):95-109. doi: 10.1016/j.jgg.2011.02.003. Epub Mar. 15, 2011.
Zhao, et al. Homozygous Deletions and Chromosome Amplifications in Human Lung Carcinomas Revealed by Single Nucleotide Polymorphism Array Analysis. Cancer Research, 65: 5561-5570 (2005).
Zhou, et al. Counting alleles reveals a connection between chromosome 18q loss and vascularinvasion. Nature Biotechnology, 19: 78-81 (2001).
Opposition Brief dated Aug. 7, 2018 for Japanese Opposition No. 2018-700659 to JP Patent 6275145.
"LB-246/12—Detection of circulating tumor DNA in early stage cancers," Available at https://www.genomeweb.com/cancer/ngs-error-correction-method-described-aacr-excitement-grows-early-cancer-detection, Accessed on Apr. 26, 2017.
Chiu, R.W.K. et al. "Noninvasive prenatal diagnosis of fetal chromosomal aneuploidy by massively parallel genomic sequencing of DNA in maternal plasma" PNAS (2008) 105(51):20458-20463.
Fong, S.L. et al. "Comparison of 7 Methods for Extracting Cell-Free DNA from Serum Samples of Colorectal Cancer Patients" Clinical Chem (2009) 55(3):587-598.
Forshew, T. et al. "Noninvasive Identification and Monitoring of Cancer Mutations by Targeted Deep Sequencing of Plasma DNA" Sci Transl Med (2012) 4(136) ra68.
Gregory et al. "Targeted Single Molecule Mutation Detection with Massively Parallel Sequencing" Nucleic Acids Research (2015) 44(3):2-11.
Hollstein, M. et al. "p53 mutations in human cancers" Science (1991) 253(5015):49-53.
Kinde, et al. Supplemental Information, Detection and quantification of rare mutations with massively parallel sequencing. Proc Natl Acad Sci U S A. Jun. 7, 2011;108(23):1-10.
Kukita, Y. et al. "High-fidelity target sequencing of individual molecules identified using barcode sequences: de novo detection and absolute quantitation of mutations in plasma cell-free DNA from cancer patients" DNA Research (2015) 22(4):269-277.

Lodes, et al. Novel Chimera-Free, High Efficiency Library Preparation for NGS Plafforms.Poster. Presented at the Plant & Animal Genome XX Conference. San Diego, California. Jan. 14-18, 2012. 1 page.
Mitelman, F. et al. "The impact of translocations and gene fusions on cancer causation" Nature Rev. Cancer (2007) 7(4):233-245.
Sanger, F. et al. "DNA sequencing with chain-terminating inhibitors" PNAS (1977) 74(12):5463-5467.
Teer, J.K. et al. "Systematic comparison of three genomic enrichment methods for massively parallel DNA sequencing" Genome Res (2010) 20(10):1420-1431.
Van Orsouw, N. et al. "Complexity Reduction of Polymorphic Sequences (CRoPSTM): A Novel Approach for Large-Scale Polymorphism Discovery in Complex Genomes" PLoS One (2007) 11(e1172):1-10.
Wang, T.L. et al. "Digital Karyotyping" PNAS (2002) 99(25):16156-16161.
Zhang et al. "Comprehensive One-Step Molecular Analysis of Mitochondrial Genome by Massively Parallel Sequencing" Clinical Chem (2012) 58(9):1322-1331.
"Blood Plasma" Oxford Dictionary of Biochemistry and Molecular Biology 81 (2d ed. 2006).
"Cohesive End," Oxford Dictionary of Biochemistry and Molecular Biology 132 (2d ed. 2006).
Fleischhacker, M. et al. "Circulating nucleic acids (CNAs) and cancer—A survey" Biochimica et Biophysica Acta (2007) 1775:181-232.
Instructions for Norit Rapid DNA Ligation Kit (Nov. 6, 2004).
Invitrogen Instructions for T4 DNA Ligase (May 5, 2002).
Mertes, F. et al. "Targeted enrichment of genomic DNA regions for next-generation sequencing" Brief Functional Genomics (2011) 10(6):374-386.
Metzker, M.L. "Sequencing technologies—the next generation" Nature Reviews Genetics (2010) 11:31-46.
Meyerson, M. et al. "Advances in understanding cancer genomes through second-generation sequencing" Nature Reviews Genetics (2010) 11:685-696.
Nielsen, R. et al. "Genotype and SNP calling from next-generation sequencing data" Nature Reviews Genetics (2011) 12(6):443-451.
Schmitt et al. Supplemental Information http://www.pnas.org/content/suppl/2012/08/01/1208715109. DCSupplemental.
Schwarzenbach, H. et al. "Cell-free nucleic acids as biomarkers in cancer patients" Nature Reviews Cancer (2011) 11:426-437.
Sehnert, A.J. et al. "Optimal Detection of Fetal Chromosomal Abnormalities by Massively Parallel DNA Sequencing of Cell-Free Fetal DNA from Maternal Blood" Clin Chem (2011) 57(7):1042-1049.
Vasyukhin, V. et al., "K-Ras Point Mutations in the Blood Plasma DNA of Patients with Colorectal Tumors" Challenges of Modern Medicine, 141-150 (Verna and Shamoo eds, 1994).
Wagle, N. et al., "High-throughput Detection of actionable Genomic alterations in clinical tumor samples by targeted, Massively Parallel sequencing," Cancer Discov. 2012, (2)1:82-93.
Wang, Y. et al., "Detection of somatic mutations and HPV in the saliva and plasma of patients with head and neck squamous cell carcinomas," Sci. Transl. Med. 2015, 7(293):293ra104.
Wang, Y. et al., "Detection of tumor-derived DNA in cerebrospinal fluid of patients with primary tumors of the brain and spinal cord," Proc. Natl. Acad. Sci. USA 2015, 112(31), 9704-9709.
Wang, Y. et al., "Diagnostic potential of tumor DNA from ovarian cyst fluid," eLife 2016, 5:e15175.
Wheeler, D.A. et al., "The complete genome of an individual by massively parallel DNA sequencing," Nature 2008, 152(7189), 872-876.
Williford, A. et al., "Gene Fusion," eLS 2013, 1-8.
"Control," Oxford Dictionary of Biochemistry and Molecular Biology (2d ed. 2006), 143.
Ajay, S.S. et al., "Accurate and comprehensive sequencing of personal genomes," Genome Res. 2011, 21(9), 1498-1505.
Albert, T.J. et al., "Direct selection of human genomic loci by microarray hybridization," Nat. Methods 2007, 4(11), 903-905.

(56) References Cited

OTHER PUBLICATIONS

Arneson, N. et al., "Whole-Genome Amplification by Adaptor-Ligation PCR of Randomly Sheared Genomic DNA (PRSG)," CSH Protocols, 2008, 3(1).
Bentley, D.R. et al., "Accurate Whole Human Genome Sequencing using Reversible Terminator Chemistry," Nature, 2008, 456(7218):53-59.
Bettegowda et al., "Detection of Circulating Tumor DNA in Early- and Late-Stage Human Malignancies," Sci. Transl. Med. 2014, 6(224):224ra24.
Bianchi, D.W. et al. "Genome-Wide Fetal Aneuploidy Detection by Maternal Plasma DNA Sequencing," Obstetrics & Gynecology, (2012) 119(5), 1-12.
Bryzgunova,O. et al., "A reliable method to concentrate circulating DNA," Analytical Biochem., 2010, 408:354-356.
CASAVA v1.8.2 User Guide http://gensoft.pasteur.fr/docs/casava/1.8.2/CASAVA_1_8_2_UG_15011196C.pdf (Oct. 2011).
Ding, L. et al., "Analysis of next-generation genomic data in cancer: accomplishments and challenges," Hum. Mol. Genet. 2010 19(R2), R188-R196.
Duncan, D.L. et al. "Next-Generation Sequencing in the Clinical Laboratory" Diagnostic Molecular Pathology: A Guide to Applied Molecular Testing 25-33 (Coleman and Tsongalis eds., 1st ed. 2016).
Gordon, D.J. et al., "Causes and consequences of aneuploidy in cancer," Nat. Rev. Genet. 2012 13(3), 189-203.
Hall, A., Short-Read DNA Sequence Alignmnet with Custom Designed FPGA-based Hardware, Thesis 2010.
Ilumina "Multiplexed Sequencing with Illumina Genome Analyzer System" https://www.illumina.com/Documents/products/datasheets/datasheet_sequencing_multiplex.pdf (Dec. 2008).
IPR2019-00130, Preliminary Response to Petition for Inter Partes Review U.S. Pat. No. 9,598,731, filed Mar. 6, 2019.
Jiang, H. et al., "SeqMap: mapping massive amount of oligonucleotides to the genome," Bioinformatics 2008, 24(20):2395-2396.
Kao,W-C. et al., "BayesCall: A model-based base-calling algorithm for high-throughput short-read sequencing," Genome Res. 2009 19(10), 1884-1895.
Kennedy, S.R. et al., "Detecting ultralow-frequency mutations by Duplex Sequencing," Nat. Protoc. 2014, 9(11), 2586-2606.
Kinde, I. et al., "Evaluation of DNA from the Papanicolaou Test to Detect Ovarian and Endometrial Cancers," Sci. Transl. Med. 2013, 5(167):167ra4.
Kinde, I. et al., "FAST-SeqS: a simple and efficient method for the detection of aneuploidy by massively parallel sequencing," PLoS One 2012, 7(7), e41162.
Kircher, M. et al., "Improved base calling for the Illumina Genome Analyzer using machine learning strategies," Genome Biol. 2009, 10(8), R83.
Kirsch, S. et al. "Sequence error storms and the landscape of mutations in cancer," Proc. Natl. Acad. Sci. USA 2012, 109(36), 14289-14290.
Koboldt, D.C.et al., "The next-generation sequencing revolution and its impact on genomics," Cell 2013, 155(1), 27-38.
Korbel, J.O. et al., "Paired-end mapping reveals extensive structural variation in the human genome," Science 2007, 318(5849), 420-426.
Krimmel, J.D. et al., "Ultra-deep sequencing detects ovarian cancer cells in peritoneal fluid and reveals somatic TP53 mutations in noncancerous tissues," Proc. Natl. Acad. Sci. USA 2016, 113(21), 6005-6010.
Ledergerber, C. et al., "Base-calling for next-generation sequencing platforms," Brief Bioinform. 2011 12(5), 489-497.
Li, H. et al., "Fast and accurate short read alignment with Burrows-Wheeler transform," Bioinformatics 2009, 25(14), 1754-1760.
Liang, K-C. et al., "Bayesian basecalling for DNA sequence analysis using hidden Markov models," IEE/ACM Trans. Comput. Biol. Bioinform. 2007 4(3), 430-440.
Liao, G.J.W. et al., "Targeted massively parallel sequencing of maternal plasma DNA permits efficient and unbiased detection of fetal alleles," Clin. Chem. 2011, 57(1), 92-101.
Lo, Y.M.D et al., "Quantitative analysis of fetal DNA in maternal plasma and serum: implications for noninvasive prenatal diagnosis," Am. J. Hum. Genet. 1998, 62(4), 768-775.
Lo, Y.M.D. et al. "Maternal Plasma DNA Sequencing Reveals the Genome-Wide Genetic and Mutational Profile of the Fetus," Sci Transl Med (2010) 2(61):1-13.
Lunter, G. et al., "Stampy: A statistical algorithm for sensitive and fast mapping of Illumina sequence reads," Genome Res. 2011, 21(6):936-939.
Mamanova, L. et al., "Target-enrichment strategies for next-generation sequencing," Nat. Methods 2010, 7(2), 111-118.
McKernon, K.J. et al., "Sequence and structural variation in a human genome uncovered by short-read, massively parallel ligation sequencing using two-base encoding," Genome Res. 2009, 19(9), 1527-1541.
Meyer, M. et al. "Illumina sequencing library preparation for highly multiplexed target capture and sequencing," Cold Spring Harb. Protoc. 2010, (6), prot5448.
Ng, S.B., et al., "Targeted capture and massively parallel sequencing of 12 human exomes," Nature 2009, 461(7261), p. 272-276.
Office action dated Dec. 21, 2018 for U.S. Appl. No. 15/978,848.
Opposition Decision dated Jan. 15, 2019 for Japanese Opposition No. 2018-700659 to JP Patent 6275145.
Parkinson, N.J. et al., "Preparation of high-quality next-generation sequencing libraries from picogram quantities of target DNA," Genome Res. 2012, 22(1), 125-133.
Quinlan, A.R. et al., "Pyrobayes: an improved base caller for SNP discovery in pyrosequences," Nat. Methods 2008 5(2), 179-181.
Redon, R. et al., "Global variation in copy number in the human genome," Nature 2006 444(7118), 444-454.
Rizzo, J.M. et al. "Key Principles and Clinical Applications of 'Next Generation' DNA Sequencing," Cancer Prev. Res., (2012) 5, 887-900.
Sausen, M. et al. "Integrated genomic analyses identify ARID1A and ARID1B alterations in the childhood cancer neuroblastoma", Nature Genetics 2013, 45(1), 12-17.
Schweiger et al., "Genome-wide massively parallel sequencing of formaldehyde fixed-paraffin embedded (FFPE) tumor tissues for copy-number- and mutation-analysis," PLoS One 2009, 4(5), e5548.
Shendure, J. et al. "Next-generation DNA sequencing," Nat. Biotechnol. 2008 26(10), 1135-1145.
Stein, et al. "The case for cloud computing in genome informatics", Genome Biol. 2010, 11 (5):207. Epub May 5, 2010.
Tie, J. et al., "Circulating tumor DNA analysis detects minimal residual disease and predicts recurrence in patients with stage II colon cancer," Sci. Transl. Med. 2016, 8(346):346ra92.
U.S. Appl. No. 61/613,413 ("Schmitt '413 provisional").
U.S. Appl. No. 61/625,319 ("Schmitt '319 provisional").
Diehl, F. et al., "Analysis of Mutations in DNA Isolated From Plasma and Stool of Colorectal Cancer Patients," Gastroenterology (2008) 135(2):489-498.
Genome Analyzer IIx Systems Specification Sheet (2009).
Guardant Health vs. FMI 1st Amended Answer to Second Amended Complaint dated May 6, 2019 (C.A. No. 17-cv-1616-LPS-CJB).
Guardant Health vs. FMI Invalidity Contentions dated Jun. 25, 2018 (C.A. No. 17-cv-1616-LPS-CJB).
Guardant Health vs. FMI Second Amended Complaint dated Mar. 6, 2018 (C.A. No. 17-cv-1616-LPS-CJB).
Guardant Health vs. FMI Suppl Invalidity References dated Feb. 15, 2019 (C.A. No. 17-cv-1616-LPS-CJB).
Guardant Health vs. FMI Supplemental Invalidity Contentions dated Mar. 29, 2019 (C.A. No. 17-cv-1616-LPS-CJB).
Guardant Health vs. PGDx Amended Answer to Second Amended Complaint dated Apr. 30, 2019 (C.A. No. 17-cv-1623-LPS-CJB).
Guardant Health vs. PGDx Invalidity Contentions dated Jun. 25, 2018 (C.A. No. 17-cv-1623-LPS-CJB).
Guardant Health vs. PGDx Second Amended Complaint dated Mar. 23, 2018 (C.A. No. 17-cv-1623-LPS-CJB).
Guardant Health vs. PGDx Second Updated Invalidity Contentions dated May 13, 2019 (C.A. No. 17-cv-1623-LPS-CJB).

(56) References Cited

OTHER PUBLICATIONS

Guardant Health vs. PGDx Updated Invalidity Contentions dated Mar. 29, 2019 (C.A. No. 17-cv-1623-LPS-CJB).
HiSeq 2000 User Guide (2010).
Illumina Preparing Samples for Paired-End Sequencing (2008).
IPR2018-00130, Petition for Inter Partes Review of U.S. Pat. No. 9,598,731, dated Nov. 7, 2018.
IPR2019-00130, Decision Denying Inter Partes Review U.S. Pat. No. 9,598,731, issued Jun. 5, 2019.
IPR2019-00634, Petition for Inter Partes Review of U.S. Pat. No. 9,840,743, dated Feb. 1, 2019.
IPR2019-00636, Petition for Inter Partes Review of U.S. Pat. No. 9,902,992, dated Feb. 1, 2019.
IPR2019-00637, Petition for Inter Partes Review of U.S. Pat. No. 9,902,992, dated Feb. 1, 2019.
IPR2019-00652, Petition for Inter Partes Review of U.S. Pat. No. 9,834,822, dated Feb. 1, 2019.
IPR2019-00653, Petition for Inter Partes Review of U.S. Pat. No. 9,834,822, dated Feb. 1, 2019.
Karow, J. "Hopkins Team Develops Method to Improve Rare Mutation Detection for Early Cancer Dx" Genome Web (2011) 3 pages.
Office action dated May 13, 2019 for U.S. Appl. No. 15/669,779.
Pel, J. et al. "Duplex proximity sequencing (pro-seq): A method to improve DNA sequencing accuracy without the cost of molecular barcoding redundancy" bioRxiv (2017) https://doi.org/10.1101/163444.
Perakis, S. et al. "Advances in Circulating Tumor DNA Analysis" Adv Clin Chem (2017) pp. 1-81.
Rafi, I. et al. "Cell-free fetal DNA and non-invasive prenatal diagnosis," Br. J. Gen. Pract. May 1, 2019; 59(562):e146-148.
Smith, T.F. et al. "Comparison of Biosequences" Adv App Math (1981) 2:482-489.
Stumm, M. et al. "Noninvasive prenatal detection of chromosomal aneuploidies using different next generation sequencing strategies and algorithms" Prenatal Diagnosis (2012) 32:569-577.
Notice of Allowance dated Aug. 1, 2019 for U.S. Appl. No. 15/978,848.
Guardant Health vs. FMI Invalidity Exhibit A-1, dated Jun. 25, 2018 (C.A. No. 17-cv-1616-LPS-CJB).
Guardant Health vs. FMI Invalidity Exhibit A-2, dated Jun. 25, 2018 (C.A. No. 17-cv-1616-LPS-CJB).
Guardant Health vs. FMI Invalidity Exhibit A-3, dated Jun. 25, 2018 (C.A. No. 17-cv-1616-LPS-CJB).
Guardant Health vs. FMI Invalidity Exhibit A-8, dated Jun. 25, 2018 (C.A. No. 17-cv-1616-LPS-CJB).
Guardant Health vs. FMI Invalidity Exhibit B-1, dated Jun. 25, 2018 (C.A. No. 17-cv-1616-LPS-CJB).
Guardant Health vs. FMI Invalidity Exhibit B-2, dated Jun. 25, 2018 (C.A. No. 17-cv-1616-LPS-CJB).
Guardant Health vs. FMI Invalidity Exhibit B-3, dated Jun. 25, 2018 (C.A. No. 17-cv-1616-LPS-CJB).
Guardant Health vs. FMI Invalidity Exhibit B-7, dated Jun. 25, 2018 (C.A. No. 17-cv-1616-LPS-CJB).
Guardant Health vs. FMI Invalidity Exhibit C-1, dated Jun. 25, 2018 (C.A. No. 17-cv-1616-LPS-CJB).
Guardant Health vs. FMI Invalidity Exhibit C-11, dated Jun. 25, 2018 (C.A. No. 17-cv-1616-LPS-CJB).
Guardant Health vs. FMI Invalidity Exhibit C-2, dated Jun. 25, 2018 (C.A. No. 17-cv-1616-LPS-CJB).
Guardant Health vs. FMI Invalidity Exhibit C-3, dated Jun. 25, 2018 (C.A. No. 17-cv-1616-LPS-CJB).
Guardant Health vs. FMI Invalidity Exhibit C-4, dated Jun. 25, 2018 (C.A. No. 17-cv-1616-LPS-CJB).
Guardant Health vs. FMI Invalidity Exhibit C-5, dated Jun. 25, 2018 (C.A. No. 17-cv-1616-LPS-CJB).
Guardant Health vs. FMI Invalidity Exhibit D-1, dated Jun. 25, 2018 (C.A. No. 17-cv-1616-LPS-CJB).
Guardant Health vs. FMI Invalidity Exhibit D-2, dated Jun. 25, 2018 (C.A. No. 17-cv-1616-LPS-CJB).
Guardant Health vs. FMI Invalidity Exhibit D-3, dated Jun. 25, 2018 (C.A. No. 17-cv-1616-LPA-CJB).
Guardant Health vs. FMI Invalidity Exhibit D-5, dated Jun. 25, 2018 (C.A. No. 17-cv-1616-LPS-CJB).
Guardant Health vs. PGDx Invalidity Claim Chart A, dated May 13, 2019 (C.A. No. 17-cv-1623-LPS-CJB).
Guardant Health vs. PGDx Invalidity Claim Chart B, dated May 13, 2019 (C.A. No. 17-cv-1623-LPS-CJB).
Guardant Health vs. PGDx Invalidity Claim Chart C, dated May 13, 2019 (C.A. No. 17-cv-1623-LPS-CJB).
Guardant Health vs. PGDx Invalidity Claim Chart D, dated May 13, 2019 (C.A. No. 17-cv-1623-LPS-CJB).
Guardant Health vs. PGDx Invalidity Claim Chart E, dated May 13, 2019 (C.A. No. 17-cv-1623-LPS-CJB).
Guardant Health vs. PGDx Invalidity Claim Chart F, dated May 13, 2019 (C.A. No. 17-cv-1623-LPS-CJB).
Guardant Health vs. PGDx Invalidity Claim Chart G, dated May 13, 2019 (C.A. No. 17-cv-1623-LPS-CJB).
Guardant Health vs. PGDx Invalidity Claim Chart H, dated May 13, 2019 (C.A. No. 17-cv-1623-LPS-CJB).
Guardant Health vs. PGDx Invalidity Claim Chart I, dated May 13, 2019 (C.A. No. 17-cv-1623-LPS-CJB).
Guardant Health vs. PGDx Invalidity Claim Chart J, dated May 13, 2019 (C.A No. 17-cv-1623-LPS-CJB).
Guardant Health vs. PGDx Invalidity Claim Chart K, dated May 13, 2019 (C.A. No. 17-cv-1623-LPS-CJB).
Guardant Health vs. PGDx Invalidity Claim Chart L, dated May 13, 2019 (C.A. No. 17-cv-1623-LPS-CJB).
Office action dated Aug. 6, 2019 for U.S. Appl. No. 14/855,301.
IPR2019-00634, Decision Instituting Inter Partes Review U.S. Pat. No.9,840,743, dated Aug. 19, 2019.
IPR2019-00636 and IPR2019-00637, Decision Denying Inter Partes Review U.S. Pat. No.9,902,992, dated Aug. 20, 2019.
IPR2019-00652, Decision Granting Inter Partes Review U.S. Pat. No.9,834,822, dated Aug. 19, 2019.
IPR2019-00653, Decision Denying Inter Partes Review U.S. Pat. No.9,834,822, dated Aug. 19, 2019.

SYSTEMS AND METHODS TO DETECT RARE MUTATIONS AND COPY NUMBER VARIATION

CROSS-REFERENCE

This application is a continuation application of U.S. patent application Ser. No. 15/828,099, filed Nov. 30, 2017, which is a continuation application of U.S. patent application Ser. No. 15/467,570, filed Mar. 23, 2017 (now U.S. Pat. No. 9,840,743), issued Dec. 12, 2017), which is a continuation application of U.S. patent application Ser. No. 14/425,189, filed Mar. 2, 2015, which is a national stage entry of international Application No. PCT/US2013/058061, filed Sep. 4, 2013, which claims priority to U.S. Provisional Patent Application No. 61/696,734, filed Sep. 4, 2012, U.S. Provisional Patent Application No. 61/704,400, filed Sep. 21, 2012, and U.S. Provisional Patent Application No. 61/793,997, filed Mar. 15, 2013, and U.S. Provisional Patent Application No. 61/845,987, filed Jul. 13, 2013, each of which is entirely incorporated herein by reference for all purposes.

BACKGROUND OF THE INVENTION

The detection and quantification of polynucleotides is important for molecular biology and medical applications such as diagnostics. Genetic testing is particularly useful for a number of diagnostic methods. For example, disorders that are caused by rare genetic alterations (e.g., sequence variants) or changes in epigenetic markers, such as cancer and partial or complete aneuploidy, may be detected or more accurately characterized with DNA sequence information.

Early detection and monitoring of genetic diseases, such as cancer is often useful and needed in the successful treatment or management of the disease. One approach may include the monitoring of a sample derived from cell free nucleic acids, a population of polynucleotides that can be found in different types of bodily fluids. In some cases, disease may be characterized or detected based on detection of genetic aberrations, such as a change in copy number variation and/or sequence variation of one or more nucleic acid sequences, or the development of other certain rare genetic alterations. Cell free DNA ("cfDNA") has been known in the art for decades, and may contain genetic aberrations associated with a particular disease. With improvements in sequencing and techniques to manipulate nucleic acids, there is a need in the art for improved methods and systems for using cell free DNA to detect and monitor disease.

SUMMARY OF THE INVENTION

The disclosure provides for a method for detecting copy number variation comprising: a) sequencing extracellular polynucleotides from a bodily sample from a subject, wherein each of the extracellular polynucleotide are optionally attached to unique barcodes; b) filtering out reads that fail to meet a set threshold; c) mapping sequence reads obtained from step (a) to a reference sequence; d) quantifying/counting mapped reads in two or more predefined regions of the reference sequence; e) determining a copy number variation in one or more of the predefined regions by (i) normalizing the number of reads in the predefined regions to each other and/or the number of unique barcodes in the predefined regions to each other; and (ii) comparing the normalized numbers obtained in step (i) to normalized numbers obtained from a control sample.

The disclosure also provides for a method for detecting a rare mutation in a cell-free or substantially cell free sample obtained from a subject comprising: a) sequencing extracellular polynucleotides from a bodily sample from a subject, wherein each of the extracellular polynucleotide generate a plurality of sequencing reads; b) sequencing extracellular polynucleotides from a bodily sample from a subject, wherein each of the extracellular polynucleotide generate a plurality of sequencing reads; sequencing extracellular polynucleotides from a bodily sample from a subject, wherein each of the extracellular polynucleotide generate a plurality of sequencing reads; c) filtering out reads that fail to meet a set threshold; d) mapping sequence reads derived from the sequencing onto a reference sequence; e) identifying a subset of mapped sequence reads that align with a variant of the reference sequence at each mappable base position; f) for each mappable base position, calculating a ratio of (a) a number of mapped sequence reads that include a variant as compared to the reference sequence, to (b) a number of total sequence reads for each mappable base position; g) normalizing the ratios or frequency of variance for each mappable base position and determining potential rare variant(s) or mutation(s); h) and comparing the resulting number for each of the regions with potential rare variant(s) or mutation(s) to similarly derived numbers from a reference sample.

Additionally, the disclosure also provides for a method of characterizing the heterogeneity of an abnormal condition in a subject, the method comprising generating a genetic profile of extracellular polynucleotides in the subject, wherein the genetic profile comprises a plurality of data resulting from copy number variation and/or other rare mutation (e.g., genetic alteration) analyses.

In some embodiments, the prevalence/concentration of each rare variant identified in the subject is reported and quantified simultaneously. In other embodiments, a confidence score, regarding the prevalence/concentrations of rare variants in the subject, is reported.

In some embodiments, extracellular polynucleotides comprise DNA. In other embodiments, extracellular polynucleotides comprise RNA. Polynucleotides may be fragments or fragmented after isolation. Additionally, the disclosure provides for a method for circulating nucleic acid isolation and extraction.

In some embodiments, extracellular polynucleotides are isolated from a bodily sample that may be selected from a group consisting of blood, plasma, serum, urine, saliva, mucosal excretions, sputum, stool and tears.

In some embodiments, the methods of the disclosure also comprise a step of determining the percent of sequences having copy number variation or other rare genetic alteration (e.g., sequence variants) in said bodily sample.

In some embodiments, the percent of sequences having copy number variation in said bodily sample is determined by calculating the percentage of predefined regions with an amount of polynucleotides above or below a predetermined threshold.

In some embodiments, bodily fluids are drawn from a subject suspected of having an abnormal condition which may be selected from the group consisting of, mutations, rare mutations, single nucleotide variants, indels, copy number variations, transversions, translocations, inversion, deletions, aneuploidy, partial aneuploidy, polyploidy, chromosomal instability, chromosomal structure alterations, gene fusions, chromosome fusions, gene truncations, gene amplification, gene duplications, chromosomal lesions, DNA lesions, abnormal changes in nucleic acid chemical modifications, abnormal changes in epigenetic patterns, abnormal changes in nucleic acid methylation infection and cancer.

In some embodiments, the subject may be a pregnant female in which the abnormal condition may be a fetal abnormality selected from the group consisting of, single nucleotide variants, indels, copy number variations, transversions, translocations, inversion, deletions, aneuploidy, partial aneuploidy, polyploidy, chromosomal instability, chromosomal structure alterations, gene fusions, chromosome fusions, gene truncations, gene amplification, gene duplications, chromosomal lesions, DNA lesions, abnormal changes in nucleic acid chemical modifications, abnormal changes in epigenetic patterns, abnormal changes in nucleic acid methylation infection and cancer In some embodiments, the method may comprise comprising attaching one or more barcodes to the extracellular polynucleotides or fragments thereof prior to sequencing, in which the barcodes comprise are unique. In other embodiments barcodes attached to extracellular polynucleotides or fragments thereof prior to sequencing are not unique.

In some embodiments, the methods of the disclosure may comprise selectively enriching regions from the subject's genome or transcriptome prior to sequencing. In other embodiments the methods of the disclosure comprise selectively enriching regions from the subject's genome or transcriptome prior to sequencing. In other embodiments the methods of the disclosure comprise non-selectively enriching regions from the subject's genome or transcriptome prior to sequencing.

Further, the methods of the disclosure comprise attaching one or more barcodes to the extracellular polynucleotides or fragments thereof prior to any amplification or enrichment step.

In some embodiments, the barcode is a polynucleotide, which may further comprise random sequence or a fixed or semi-random set of oligonucleotides that in combination with the diversity of molecules sequenced from a select region enables identification of unique molecules and be at least a 3, 5, 10, 15, 20 25, 30, 35, 40, 45, or 50mer base pairs in length.

In some embodiments, extracellular polynucleotides or fragments thereof may be amplified. In some embodiments amplification comprises global amplification or whole genome amplification.

In some embodiments, sequence reads of unique identity may be detected based on sequence information at the beginning (start) and end (stop) regions of the sequence read and the length of the sequence read. In other embodiments sequence molecules of unique identity are detected based on sequence information at the beginning (start) and end (stop) regions of the sequence read, the length of the sequence read and attachment of a barcode.

In some embodiments, amplification comprises selective amplification, non-selective amplification, suppression amplification or subtractive enrichment.

In some embodiments, the methods of the disclosure comprise removing a subset of the reads from further analysis prior to quantifying or enumerating reads.

In some embodiments, the method may comprise filtering out reads with an accuracy or quality score of less than a threshold, e.g., 90%, 99%, 99.9%, or 99.99% and/or mapping score less than a threshold, e.g., 90%, 99%, 99.9% or 99.99%. In other embodiments, methods of the disclosure comprise filtering reads with a quality score lower than a set threshold.

In some embodiments, predefined regions are uniform or substantially uniform in size, about 10 kb, 20 kb, 30 kb 40 kb, 50 kb, 60 kb, 70 kb, 80 kb, 90 kb, or 100 kb in size. In some embodiments, at least 50, 100, 200, 500, 1000, 2000, 5000, 10,000, 20,000, or 50,000 regions are analyzed.

In some embodiments, a genetic variant, rare mutation or copy number variation occurs in a region of the genome selected from the group consisting of gene fusions, gene duplications, gene deletions, gene translocations, microsatellite regions, gene fragments or combination thereof. In other embodiments a genetic variant, rare mutation, or copy number variation occurs in a region of the genome selected from the group consisting of genes, oncogenes, tumor suppressor genes, promoters, regulatory sequence elements, or combination thereof. In some embodiments the variant is a nucleotide variant, single base substitution, or small indel, transversion, translocation, inversion, deletion, truncation or gene truncation about 1, 2, 3, 4, 5, 6, 7, 8, 9, 10, 15 or 20 nucleotides in length.

In some embodiments, the method comprises correcting/normalizing/adjusting the quantity of mapped reads using the barcodes or unique properties of individual reads.

In some embodiments, enumerating the reads is performed through enumeration of unique barcodes in each of the predefined regions and normalizing those numbers across at least a subset of predefined regions that were sequenced. In some embodiments, samples at succeeding time intervals from the same subject are analyzed and compared to previous sample results. The method of the disclosure may further comprise determining partial copy number variation frequency, loss of heterozygosity, gene expression analysis, epigenetic analysis and hypermethylation analysis after amplifying the barcode-attached extracellular polynucleotides.

In some embodiments, copy number variation and rare mutation analysis is determined in a cell-free or substantially cell free sample obtained from a subject using multiplex sequencing, comprising performing over 10,000 sequencing reactions; simultaneously sequencing at least 10,000 different reads; or performing data analysis on at least 10,000 different reads across the genome. The method may comprise multiplex sequencing comprising performing data analysis on at least 10,000 different reads across the genome. The method may further comprise enumerating sequenced reads that are uniquely identifiable.

In some embodiments, the methods of the disclosure comprise normalizing and detection is performed using one or more of hidden markov, dynamic programming, support vector machine, Bayesian network, trellis decoding, Viterbi decoding, expectation maximization, Kalman filtering, or neural network methodologies.

In some embodiments the methods of the disclosure comprise monitoring disease progression, monitoring residual disease, monitoring therapy, diagnosing a condition, prognosing a condition, or selecting a therapy based on discovered variants.

In some embodiments, a therapy is modified based on the most recent sample analysis. Further, the methods of the disclosure comprise inferring the genetic profile of a tumor, infection or other tissue abnormality. In some embodiments growth, remission or evolution of a tumor, infection or other tissue abnormality is monitored. In some embodiments the subject's immune system are analyzed and monitored at single instances or over time.

In some embodiments, the methods of the disclosure comprise identification of a variant that is followed up through an imaging test (e.g., CT, PET-CT, MRI, X-ray, ultrasound) for localization of the tissue abnormality suspected of causing the identified variant.

In some embodiments, the methods of the disclosure comprise use of genetic data obtained from a tissue or tumor biopsy from the same patient. In some embodiments, whereby the phylogenetics of a tumor, infection or other tissue abnormality is inferred.

In some embodiments, the methods of the disclosure comprise performing population-based no-calling and identification of low-confidence regions. In some embodiments, obtaining the measurement data for the sequence coverage comprises measuring sequence coverage depth at every position of the genome. In some embodiments correcting the measurement data for the sequence coverage bias comprises calculating window-averaged coverage. In some embodiments correcting the measurement data for the sequence coverage bias comprises performing adjustments to account for GC bias in the library construction and sequencing process. In some embodiments correcting the measurement data for the sequence coverage bias comprises performing adjustments based on additional weighting factor associated with individual mappings to compensate for bias.

In some embodiments, the methods of the disclosure comprise extracellular polynucleotide derived from a diseased cell origin. In some embodiments, the extracellular polynucleotide is derived from a healthy cell origin.

The disclosure also provides for a system comprising a computer readable medium for performing the following steps: selecting predefined regions in a genome; enumerating number of sequence reads in the predefined regions; normalizing the number of sequence reads across the predefined regions; and determining percent of copy number variation in the predefined regions. In some embodiments, the entirety of the genome or at least 10%, 20%, 30%, 40%, 50%, 60%, 70%, 80%, or 90% of the genome is analyzed. In some embodiments, computer readable medium provides data on percent cancer DNA or RNA in plasma or serum to the end user.

In some embodiments, the amount of genetic variation, such as polymorphisms or causal variants is analyzed. In some embodiments, the presence or absence of genetic alterations is detected.

The disclosure also provides for a method for detecting a rare mutation in a cell-free or a substantially cell free sample obtained from a subject comprising: a) sequencing extracellular polynucleotides from a bodily sample from a subject, wherein each of the extracellular polynucleotides generate a plurality of sequencing reads; b) filtering out reads that fail to meet a set threshold; c) mapping sequence reads derived from the sequencing onto a reference sequence; d) identifying a subset of mapped sequence reads that align with a variant of the reference sequence at each mappable base position; e) for each mappable base position, calculating a ratio of (a) a number of mapped sequence reads that include a variant as compared to the reference sequence, to (b) a number of total sequence reads for each mappable base position; f) normalizing the ratios or frequency of variance for each mappable base position and determining potential rare variant(s) or other genetic alteration(s); and g) comparing the resulting number for each of the regions This disclosure also provides for a method comprising: a. providing at least one set of tagged parent polynucleotides, and for each set of tagged parent polynucleotides; b. amplifying the tagged parent polynucleotides in the set to produce a corresponding set of amplified progeny polynucleotides; c. sequencing a subset (including a proper subset) of the set of amplified progeny polynucleotides, to produce a set of sequencing reads; and d. collapsing the set of sequencing reads to generate a set of consensus sequences, each consensus sequence corresponding to a unique polynucleotide among the set of tagged parent polynucleotides. In certain embodiments the method further comprises: e. analyzing the set of consensus sequences for each set of tagged parent molecules.

In some embodiments each polynucleotide in a set is mappable to a reference sequence.

In some embodiments the method comprises providing a plurality of sets of tagged parent polynucleotides, wherein each set is mappable to a different reference sequence.

In some embodiments the method further comprises converting initial starting genetic material into the tagged parent polynucleotides.

In some embodiments the initial starting genetic material comprises no more than 100 ng of polynucleotides.

In some embodiments the method comprises bottlenecking the initial starting genetic material prior to converting.

In some embodiments the method comprises converting the initial starting genetic material into tagged parent polynucleotides with a conversion efficiency of at least 10%, at least 20%, at least 30%, at least 40%, at least 50%, at least 60%, at least 80% or at least 90%.

In some embodiments converting comprises any of blunt-end ligation, sticky end ligation, molecular inversion probes, PCR, ligation-based PCR, single strand ligation and single strand circularization.

In some embodiments the initial starting genetic material is cell-free nucleic acid.

In some embodiments a plurality of the reference sequences are from the same genome.

In some embodiments each tagged parent polynucleotide in the set is uniquely tagged.

In some embodiments the tags are non-unique.

In some embodiments the generation of consensus sequences is based on information from the tag and/or at least one of sequence information at the beginning (start) region of the sequence read, the end (stop) regions of the sequence read and the length of the sequence read.

In some embodiments the method comprises sequencing a subset of the set of amplified progeny polynucleotides sufficient to produce sequence reads for at least one progeny from of each of at least 20%, at least 30%, at least 40%, at least 50%, at least 60%, at least 70%, at least 80%, at least 90% at least 95%, at least 98%, at least 99%, at least 99.9% or at least 99.99% of unique polynucleotides in the set of tagged parent polynucleotides.

In some embodiments the at least one progeny is a plurality of progeny, e.g., at least 2, at least 5 or at least 10 progeny.

In some embodiments the number of sequence reads in the set of sequence reads is greater than the number of unique tagged parent polynucleotides in the set of tagged parent polynucleotides.

In some embodiments the subset of the set of amplified progeny polynucleotides sequenced is of sufficient size so that any nucleotide sequence represented in the set of tagged parent polynucleotides at a percentage that is the same as the percentage per-base sequencing error rate of the sequencing platform used, has at least a 50%, at least a 60%, at least a 70%, at least a 80%, at least a 90% at least a 95%, at least a 98%, at least a 99%, at least a 99.9% or at least a 99.99% chance of being represented among the set of consensus sequences.

In some embodiments the method comprises enriching the set of amplified progeny polynucleotides for polynucleotides mapping to one or more selected reference sequences by: (i) selective amplification of sequences from initial starting genetic material converted to tagged parent polynucleotides; (ii) selective amplification of tagged parent polynucleotides; (iii) selective sequence capture of amplified progeny polynucleotides; or (iv) selective sequence capture of initial starting genetic material.

In some embodiments analyzing comprises normalizing a measure (e.g., number) taken from a set of consensus sequences against a measure taken from a set of consensus sequences from a control sample.

In some embodiments analyzing comprises detecting mutations, rare mutations, single nucleotide variants, indels, copy number variations, transversions, translocations, inversion, deletions, aneuploidy, partial aneuploidy, polyploidy, chromosomal instability, chromosomal structure alterations, gene fusions, chromosome fusions, gene truncations, gene amplification, gene duplications, chromosomal lesions, DNA lesions, abnormal changes in nucleic acid chemical modifications, abnormal changes in epigenetic patterns, abnormal changes in nucleic acid methylation infection or cancer.

In some embodiments the polynucleotides comprise DNA, RNA, a combination of the two or DNA plus RNA-derived cDNA.

In some embodiments a certain subset of polynucleotides is selected for or is enriched based on polynucleotide length in base-pairs from the initial set of polynucleotides or from the amplified polynucleotides.

In some embodiments analysis further comprises detection and monitoring of an abnormality or disease within an individual, such as, infection and/or cancer.

In some embodiments the method is performed in combination with immune repertoire profiling.

In some embodiments the polynucleotides are extract from the group consisting of blood, plasma, serum, urine, saliva, mucosal excretions, sputum, stool, and tears.

In some embodiments collapsing comprising detecting and/or correcting errors, nicks or lesions present in the sense or anti-sense strand of the tagged parent polynucleotides or amplified progeny polynucleotides.

This disclosure also provides for a method comprising detecting genetic variation in initial starting genetic material with a sensitivity of at least 5%, at least 1%, at least 0.5%, at least 0.1% or at least 0.05%. In some embodiments the initial starting genetic material is provided in an amount less than 100 ng of nucleic acid, the genetic variation is copy number/heterozygosity variation and detecting is performed with sub-chromosomal resolution; e.g., at least 100 megabase resolution, at least 10 megabase resolution, at least 1 megabase resolution, at least 100 kilobase resolution, at least 10 kilobase resolution or at least 1 kilobase resolution. In another embodiment the method comprises providing a plurality of sets of tagged parent polynucleotides, wherein each set is mappable to a different reference sequence. In another embodiment the reference sequence is the locus of a tumor marker, and analyzing comprises detecting the tumor marker in the set of consensus sequences. In another embodiment the tumor marker is present in the set of consensus sequences at a frequency less than the error rate introduced at the amplifying step. In another embodiment the at least one set is a plurality of sets, and the reference sequences comprise a plurality of reference sequences, each of which is the locus of a tumor marker. In another embodiment analyzing comprises detecting copy number variation of consensus sequences between at least two sets of parent polynucleotides. In another embodiment analyzing comprises detecting the presence of sequence variations compared with the reference sequences. In another embodiment analyzing comprises detecting the presence of sequence variations compared with the reference sequences and detecting copy number variation of consensus sequences between at least two sets of parent polynucleotides. In another embodiment collapsing comprises: i. grouping sequences reads sequenced from amplified progeny polynucleotides into families, each family amplified from the same tagged parent polynucleotide; and ii. determining a consensus sequence based on sequence reads in a family.

This disclosure also provides for a system comprising a computer readable medium for performing the following steps: a. providing at least one set of tagged parent polynucleotides, and for each set of tagged parent polynucleotides; b. amplifying the tagged parent polynucleotides in the set to produce a corresponding set of amplified progeny polynucleotides; c. sequencing a subset (including a proper subset) of the set of amplified progeny polynucleotides, to produce a set of sequencing reads; and d. collapsing the set of sequencing reads to generate a set of consensus sequences, each consensus sequence corresponding to a unique polynucleotide among the set of tagged parent polynucleotides and, optionally, e. analyzing the set of consensus sequences for each set of tagged parent molecules.

This disclosure also provides a method comprising: a. providing at least one set of tagged parent polynucleotides, and for each set of tagged parent polynucleotides; b. amplifying the tagged parent polynucleotides in the set to produce a corresponding set of amplified progeny polynucleotides; c. sequencing a subset (including a proper subset) of the set of amplified progeny polynucleotides, to produce a set of sequencing reads; d. collapsing the set of sequencing reads to generate a set of consensus sequences, each consensus sequence corresponding to a unique polynucleotide among the set of tagged parent polynucleotides; and e. filtering out from among the consensus sequences those that fail to meet a quality threshold. In one embodiment the quality threshold considers a number of sequence reads from amplified progeny polynucleotides collapsed into a consensus sequence. In another embodiment the quality threshold considers a number of sequence reads from amplified progeny polynucleotides collapsed into a consensus sequence. This disclosure also provides a system comprising a computer readable medium for performing the aforesaid method.

This disclosure also provides a method comprising: a. providing at least one set of tagged parent polynucleotides, wherein each set maps to a different reference sequence in one or more genomes, and, for each set of tagged parent polynucleotides; i. amplifying the first polynucleotides to produce a set of amplified polynucleotides; ii. sequencing a subset of the set of amplified polynucleotides, to produce a set of sequencing reads; and iii. collapsing the sequence reads by: 1. grouping sequences reads sequenced from amplified progeny polynucleotides into families, each family amplified from the same tagged parent polynucleotide. In one embodiment collapsing further comprises: 2. determining a quantitative measure of sequence reads in each family. In another embodiment the method further comprises (including a) including a): b. determining a quantitative measure of unique families; and c. based on (1) the quantitative measure of unique families and (2) the quantitative measure of sequence reads in each group, inferring a measure of unique tagged parent polynucleotides in the set. In another embodiment inferring is performed using statistical or probabilistic models. In another embodiment wherein the at least one set is a plurality of sets. In another embodiment the method further comprises correcting for amplification or representational bias between the two sets. In another embodiment the method further comprises using a control or set of control samples to correct for amplification or representational biases between the two sets. In another embodiment the method further comprises determining copy number variation between the sets. In another embodiment the method further comprises (including a, b, c): d. determining a quantitative measure of polymorphic forms among the families; and e. based on the determined quantitative measure of polymorphic forms, inferring a quantitative measure of polymorphic forms in the number of inferred unique tagged parent polynucleotides. In another embodiment wherein polymorphic forms include but are not limited to: substitutions, insertions, deletions, inversions, microsatellite changes, transversions, translocations, fusions, methylation, hypermethylation, hyrdroxymethylation, acetylation, epigenetic variants, regulatory-associated variants or protein binding sites. In another embodiment wherein the sets derive from a common sample, the method further comprising: a. inferring copy number variation for the plurality of sets based on a comparison of the inferred number of tagged parent polynucleotides in each set mapping to each of a plurality of reference sequences. In another embodiment the original number of polynucleotides in each set is further inferred. This disclosure also provides a system comprising a computer readable medium for performing the aforesaid methods.

This disclosure also provides a method of determining copy number variation in a sample that includes polynucleotides, the method comprising: a. providing at least two sets of first polynucleotides, wherein each set maps to a different reference sequence in a genome, and, for each set of first polynucleotides; i. amplifying the polynucleotides to produce a set of amplified polynucleotides; ii. sequencing a subset of the set of amplified polynucleotides, to produce a set of sequencing reads; iii. grouping sequences reads sequenced from amplified polynucleotides into families, each family amplified from the same first polynucleotide in the set; iv. inferring a quantitative measure of families in the set; b. determining copy number variation by comparing the quantitative measure of families in each set. This disclosure also provides a system comprising a computer readable medium for performing the aforesaid methods.

This disclosure also provides a method of inferring frequency of sequence calls in a sample of polynucleotides comprising: a. providing at least one set of first polynucleotides, wherein each set maps to a different reference sequence in one or more genomes, and, for each set of first polynucleotides; i. amplifying the first polynucleotides to produce a set of amplified polynucleotides; ii. sequencing a subset of the set of amplified polynucleotides, to produce a set of sequencing reads; iii. grouping the sequence reads into families, each family comprising sequence reads of amplified polynucleotides amplified from the same first polynucleotide; b. inferring, for each set of first polynucleotides, a call frequency for one or more bases in the set of first polynucleotides, wherein inferring comprises: i. assigning, for each family, confidence score for each of a plurality of calls, the confidence score taking into consideration a frequency of the call among members of the family; and ii. estimating a frequency of the one or more calls taking into consideration the confidence scores of the one or more calls assigned to each family. This disclosure also provides a system comprising a computer readable medium for performing the aforesaid methods.

This disclosure also provides a method of communicating sequence information about at least one individual polynucleotide molecule comprising: a. providing at least one individual polynucleotide molecule; b. encoding sequence information in the at least one individual polynucleotide molecule to produce a signal; c. passing at least part of the signal through a channel to produce a received signal comprising nucleotide sequence information about the at least one individual polynucleotide molecule, wherein the received signal comprises noise and/or distortion; d. decoding the received signal to produce a message comprising sequence information about the at least one individual polynucleotide molecule, wherein decoding reduces noise and/or distortion in the message; and e. providing the message to a recipient. In one embodiment the noise comprises incorrect nucleotide calls. In another embodiment distortion comprises uneven amplification of the individual polynucleotide molecule compared with other individual polynucleotide molecules. In another embodiment distortion results from amplification or sequencing bias. In another embodiment the at least one individual polynucleotide molecule is a plurality of individual polynucleotide molecules, and decoding produces a message about each molecule in the plurality. In another embodiment encoding comprises amplifying the at least individual polynucleotide molecule which has optionally been tagged, wherein the signal comprises a collection of amplified molecules. In another embodiment the channel comprises a polynucleotide sequencer and the received signal comprises sequence reads of a plurality of polynucleotides amplified from the at least one individual polynucleotide molecule. In another embodiment decoding comprises grouping sequence reads of amplified molecules amplified from each of the at least one individual polynucleotide molecules. In another embodiment the decoding consists of a probabilistic or statistical method of filtering the generated sequence signal. This disclosure also provides a system comprising a computer readable medium for performing the aforesaid methods.

In another embodiment the polynucleotides are derived from tumor genomic DNA or RNA. In another embodiment the polynucleotides are derived from cell-free polynucleotides, exosomal polynucleotides, bacterial polynucleotides or viral polynucleotides. In another embodiment further comprising the detection and/or association of affected molecular pathways. In another embodiment further comprising serial monitoring of the health or disease state of an individual. In another embodiment whereby the phylogeny of a genome associated with a disease within an individual is inferred. In another embodiment further comprising diagnosis, monitoring or treatment of a disease. In another embodiment the treatment regimen is selected or modified based on detected polymorphic forms or CNVs or associated pathways. In another embodiment the treatment comprises of a combination therapy.

This disclosure also provides a computer readable medium in non-transitory, tangible form comprising executable code configured to perform the following steps: selecting predefined regions in a genome; accessing sequence reads and enumerating number of sequence reads in the predefined regions; normalizing the number of sequence reads across the predefined regions; and determining percent of copy number variation in the predefined regions.

This disclosure also provides a computer readable medium in non-transitory, tangible form comprising executable code configured to perform the following steps: a. accessing a data file comprising a plurality of sequencing reads; b. filtering out reads that fail to meet a set threshold;

c. mapping sequence reads derived from the sequencing onto a reference sequence; d. identifying a subset of mapped sequence reads that align with a variant of the reference sequence at each mappable base position; e. for each mappable base position, calculating a ratio of (a) a number of mapped sequence reads that include a variant as compared to the reference sequence, to (b) a number of total sequence reads for each mappable base position; f. normalizing the ratios or frequency of variance for each mappable base position and determining potential rare variant(s) or other genetic alteration(s); and g. comparing the resulting number for each of the regions with potential rare variant(s) or mutation(s) to similarly derived numbers from a reference sample.

This disclosure also provides a computer readable medium in non-transitory, tangible form comprising executable code configured to perform the following steps: a. accessing a data file comprising a plurality of sequencing reads, wherein the sequence reads derive from a set of progeny polynucleotides amplified from at least one set of tagged parent polynucleotides; b. collapsing the set of sequencing reads to generate a set of consensus sequences, each consensus sequence corresponding to a unique polynucleotide among the set of tagged parent polynucleotides.

This disclosure also provides a computer readable medium in non-transitory, tangible form comprising executable code configured to perform the following steps: a. accessing a data file comprising a plurality of sequencing reads, wherein the sequence reads derive from a set of progeny polynucleotides amplified from at least one set of tagged parent polynucleotides; b. collapsing the set of sequencing reads to generate a set of consensus sequences, each consensus sequence corresponding to a unique polynucleotide among the set of tagged parent polynucleotides; c. filtering out from among the consensus sequences those that fail to meet a quality threshold.

This disclosure also provides a computer readable medium in non-transitory, tangible form comprising executable code configured to perform the following steps: a. accessing a data file comprising a plurality of sequencing reads, wherein the sequence reads derive from a set of progeny polynucleotides amplified from at least one set of tagged parent polynucleotides; and i. collapsing the sequence reads by: 1. grouping sequences reads sequenced from amplified progeny polynucleotides into families, each family amplified from the same tagged parent polynucleotide and, optionally, 2. determining a quantitative measure of sequence reads in each family. In certain embodiments, the executable code further performs the steps of: b. determining a quantitative measure of unique families; c. based on (1) the quantitative measure of unique families and (2) the quantitative measure of sequence reads in each group, inferring a measure of unique tagged parent polynucleotides in the set. In certain embodiments, the executable code further performs the steps of: d. determining a quantitative measure of polymorphic forms among the families; and e. based on the determined quantitative measure of polymorphic forms, inferring a quantitative measure of polymorphic forms in the number of inferred unique tagged parent polynucleotides.

This disclosure also provides a computer readable medium in non-transitory, tangible form comprising executable code configured to perform the following steps: a. accessing a data file comprising a plurality of sequencing reads, wherein the sequence reads derive from a set of progeny polynucleotides amplified from at least one set of tagged parent polynucleotides grouping sequences reads sequenced from amplified polynucleotides into families, each family amplified from the same first polynucleotide in the set; b. inferring a quantitative measure of families in the set; c. determining copy number variation by comparing the quantitative measure of families in each set.

This disclosure also provides a computer readable medium in non-transitory, tangible form comprising executable code configured to perform the following steps: a. accessing a data file comprising a plurality of sequencing reads, wherein the sequence reads derive from a set of progeny polynucleotides amplified from at least one set of tagged parent polynucleotides grouping the sequence reads into families, each family comprising sequence reads of amplified polynucleotides amplified from the same first polynucleotide; b. inferring, for each set of first polynucleotides, a call frequency for one or more bases in the set of first polynucleotides, wherein inferring comprises: c. assigning, for each family, confidence score for each of a plurality of calls, the confidence score taking into consideration a frequency of the call among members of the family; and d. estimating a frequency of the one or more calls taking into consideration the confidence scores of the one or more calls assigned to each family.

This disclosure also provides a computer readable medium in non-transitory, tangible form comprising executable code configured to perform the following steps: a. accessing a data accessing a data file comprising a received signal that comprises endoded sequence information from at least one individual polynucleotide molecule wherein the received signal comprises noise and/or distortion; b. decoding the received signal to produce a message comprising sequence information about the at least one individual polynucleotide molecule, wherein decoding reduces noise and/or distortion about each individual polynucleotide in the message; and c. writing the message comprising sequence information about the at least one individual polynucleotide molecule to a computer file.

This disclosure also provides a computer readable medium in non-transitory, tangible form comprising executable code configured to perform the following steps: a. accessing a data file comprising a plurality of sequencing reads, wherein the sequence reads derive from a set of progeny polynucleotides amplified from at least one set of tagged parent polynucleotides; b. collapsing the set of sequencing reads to generate a set of consensus sequences, each consensus sequence corresponding to a unique polynucleotide among the set of tagged parent polynucleotides; c. filtering out from among the consensus sequences those that fail to meet a quality threshold.

This disclosure also provides a computer readable medium in non-transitory, tangible form comprising executable code configured to perform the following steps: a. accessing a data file comprising a plurality of sequencing reads, wherein the sequence reads derive from a set of progeny polynucleotides amplified from at least one set of tagged parent polynucleotides; and b. collapsing the sequence reads by: i. grouping sequences reads sequenced from amplified progeny polynucleotides into families, each family amplified from the same tagged parent polynucleotide; and ii. optionally, determining a quantitative measure of sequence reads in each family. In certain embodiments, the executable code further performs the steps of: c. determining a quantitative measure of unique families; d. based on (1) the quantitative measure of unique families and (2) the quantitative measure of sequence reads in each group, inferring a measure of unique tagged parent polynucleotides in the set. In certain embodiments, the executable code further performs the steps of: e. determining a quantitative measure of polymorphic forms among the families; and f. based on the determined quantitative measure of polymorphic forms, inferring a quantitative measure of polymorphic forms in the number of inferred unique tagged parent polynucleotides. In certain embodiments, the executable code further performs the steps of: e. inferring copy number variation for the plurality of sets based on a comparison of the inferred number of tagged parent polynucleotides in each set mapping to each of a plurality of reference sequences.

This disclosure also provides a computer readable medium in non-transitory, tangible form comprising executable code configured to perform the following steps: a. accessing a data file comprising a plurality of sequencing reads, wherein the sequence reads derive from a set of progeny polynucleotides amplified from at least one set of tagged parent polynucleotides; b. grouping sequences reads sequenced from amplified polynucleotides into families, each family amplified from the same first polynucleotide in the set; c. inferring a quantitative measure of families in the set; d. determining copy number variation by comparing the quantitative measure of families in each set.

This disclosure also provides a computer readable medium in non-transitory, tangible form comprising executable code configured to perform the following steps: a. accessing a data file comprising a plurality of sequencing reads, wherein the sequence reads derive from a set of progeny polynucleotides amplified from at least one set of tagged parent polynucleotides grouping the sequence reads into families, each family comprising sequence reads of amplified polynucleotides amplified from the same first polynucleotide; and b. inferring, for each set of first polynucleotides, a call frequency for one or more bases in the set of first polynucleotides, wherein inferring comprises: i. assigning, for each family, confidence score for each of a plurality of calls, the confidence score taking into consideration a frequency of the call among members of the family; and ii. estimating a frequency of the one or more calls taking into consideration the confidence scores of the one or more calls assigned to each family.

This disclosure also provides a method comprising: a. providing a sample comprising between 100 and 100,000 haploid human genome equivalents of cell free DNA (cfDNA) polynucleotides; and b. tagging the polynucleotides with between 2 and 1,000,000 unique identifiers. In certain embodiments, the number of unique identifiers is at least 3, at least 5, at least 10, at least 15 or at least 25 and at most 100, at most 1000 or at most 10,000. In certain embodiments, the number of unique identifiers is at most 100, at most 1000, at most 10,000, at most 100,000.

This disclosure also provides a method comprising: a. providing a sample comprising a plurality of human haploid genome equivalents of fragmented polynucleotides; b. determining z, wherein z is a measure of central tendency (e.g., mean, median or mode) of expected number of duplicate polynucleotides starting at any position in the genome, wherein duplicate polynucleotides have the same start and stop positions; and c. tagging polynucleotides in sample with n unique identifiers, wherein n is between 2 and 100,000*z, 2 and 10,000*z, 2 and 1,000*z or 2 and 100*z.

This disclosure also provides a method comprising: a. providing at least one set of tagged parent polynucleotides, and for each set of tagged parent polynucleotides; b. producing a plurality of sequence reads for each tagged parent polynucleotide in the set to produce a set of sequencing reads; and c. collapsing the set of sequencing reads to generate a set of consensus sequences, each consensus sequence corresponding to a unique polynucleotide among the set of tagged parent polynucleotides.

The disclosure provides for a method for detecting copy number variation comprising: a) sequencing extracellular polynucleotides from a bodily sample from a subject, wherein each of the extracellular polynucleotide generate a plurality of sequencing reads; b) filtering out reads that fail to meet a set threshold; c) mapping the sequence reads obtained from step (a), after reads are filtered out, to a reference sequence; d) quantifying or enumerating mapped reads in two or more predefined regions of the reference sequence; and e) determining copy number variation in one or more of the predefined regions by: (ii) normalizing number of reads in the predefined regions to each other and/or the number of unique sequence reads in the predefined regions to one another; (ii) comparing the normalized numbers obtained in step (i) to normalized numbers obtained from a control sample.

The disclosure also provides for a method for detecting a rare mutation in a cell-free or substantially cell free sample obtained from a subject comprising: a) sequencing extracellular polynucleotides from a bodily sample from a subject, wherein each of the extracellular polynucleotide generate a plurality of sequencing reads; b) performing multiplex sequencing on regions or whole-genome sequencing if enrichment is not performed; c) filtering out reads that fail to meet a set threshold; d) mapping sequence reads derived from the sequencing onto a reference sequence; e) identifying a subset of mapped sequence reads that align with a variant of the reference sequence at each mappable base position; f) for each mappable base position, calculating a ratio of (a) a number of mapped sequence reads that include a variant as compared to the reference sequence, to (b) a number of total sequence reads for each mappable base position; g) normalizing the ratios or frequency of variance for each mappable base position and determining potential rare variant(s) or mutation(s); and h) and comparing the resulting number for each of the regions with potential rare variant(s) or mutation(s) to similarly derived numbers from a reference sample.

The disclosure also provides for a method of characterizing the heterogeneity of an abnormal condition in a subject, the method comprising generating a genetic profile of extracellular polynucleotides in the subject, wherein the genetic profile comprises a plurality of data resulting from copy number variation and rare mutation analyses.

In some embodiments, the prevalence/concentration of each rare variant identified in the subject is reported and quantified simultaneously. In some embodiments, a confidence score, regarding the prevalence/concentrations of rare variants in the subject, is reported.

In some embodiments, the extracellular polynucleotides comprise DNA. In some embodiments, the extracellular polynucleotides comprise RNA.

In some embodiments, the methods further comprise isolating extracellular polynucleotides from the bodily sample. In some embodiments, the isolating comprises a method for circulating nucleic acid isolation and extraction. In some embodiments, the methods further comprise fragmenting said isolated extracellular polynucleotides. In some embodiments, the bodily sample is selected from the group consisting of blood, plasma, serum, urine, saliva, mucosal excretions, sputum, stool and tears.

In some embodiments, the methods further comprise the step of determining the percent of sequences having copy number variation or rare mutation or variant in said bodily sample. In some embodiments, the determining comprises calculating the percentage of predefined regions with an amount of polynucleotides above or below a predetermined threshold.

In some embodiments, the subject is suspected of having an abnormal condition. In some embodiments, the abnormal condition is selected from the group consisting of mutations, rare mutations, indels, copy number variations, transversions, translocations, inversion, deletions, aneuploidy, partial aneuploidy, polyploidy, chromosomal instability, chromosomal structure alterations, gene fusions, chromosome fusions, gene truncations, gene amplification, gene duplications, chromosomal lesions, DNA lesions, abnormal changes in nucleic acid chemical modifications, abnormal changes in epigenetic patterns, abnormal changes in nucleic acid methylation infection and cancer.

In some embodiments, the subject is a pregnant female. In some embodiments, the copy number variation or rare mutation or genetic variant is indicative of a fetal abnormality. In some embodiments, the fetal abnormality is selected from the group consisting of mutations, rare mutations, indels, copy number variations, transversions, translocations, inversion, deletions, aneuploidy, partial aneuploidy, polyploidy, chromosomal instability, chromosomal structure alterations, gene fusions, chromosome fusions, gene truncations, gene amplification, gene duplications, chromosomal lesions, DNA lesions, abnormal changes in nucleic acid chemical modifications, abnormal changes in epigenetic patterns, abnormal changes in nucleic acid methylation infection and cancer.

In some embodiments, the methods further comprise attaching one or more barcodes to the extracellular polynucleotides or fragments thereof prior to sequencing. In some embodiments, each barcode attached to extracellular polynucleotides or fragments thereof prior to sequencing is unique. In some embodiments, each barcode attached to extracellular polynucleotides or fragments thereof prior to sequencing is not unique.

In some embodiments, the methods further comprise selectively enriching regions from the subject's genome or transcriptome prior to sequencing. In some embodiments, the methods further comprise non-selectively enriching regions from the subject's genome or transcriptome prior to sequencing.

In some embodiments, the methods further comprise attaching one or more barcodes to the extracellular polynucleotides or fragments thereof prior to any amplification or enrichment step. In some embodiments, the barcode is a polynucleotide. In some embodiments, the barcode comprises random sequence. In some embodiments, the barcode comprises a fixed or semi-random set of oligonucleotides that in combination with the diversity of molecules sequenced from a select region enables identification of unique molecules. In some embodiments, the barcodes comprise oligonucleotides is at least a 3, 5, 10, 15, 20 25, 30, 35, 40, 45, or 50mer base pairs in length.

In some embodiments, the methods further comprise amplifying the extracellular polynucleotides or fragments thereof. In some embodiments, the amplification comprises global amplification or whole genome amplification. In some embodiments, the amplification comprises selective amplification. In some embodiments, the amplification comprises non-selective amplification. In some embodiments, suppression amplification or subtractive enrichment is performed.

In some embodiments, sequence reads of unique identity are detected based on sequence information at the beginning (start) and end (stop) regions of the sequence read and the length of the sequence read. In some embodiments, sequence molecules of unique identity are detected based on sequence information at the beginning (start) and end (stop) regions of the sequence read, the length of the sequence read and attachment of a barcode.

In some embodiments, the methods further comprise removing a subset of the reads from further analysis prior to quantifying or enumerating reads. In some embodiments, removing comprises filtering out reads with an accuracy or quality score of less than a threshold, e.g., 90%, 99%, 99.9%, or 99.99% and/or mapping score less than a threshold, e.g., 90%, 99%, 99.9% or 99.99%. In some embodiments, the methods further comprise filtering reads with a quality score lower than a set threshold.

In some embodiments, the predefined regions are uniform or substantially uniform in size. In some embodiments, the predefined regions are at least about 10 kb, 20 kb, 30 kb 40 kb, 50 kb, 60 kb, 70 kb, 80 kb, 90 kb, or 100 kb in size.

In some embodiments, at least 50, 100, 200, 500, 1000, 2000, 5000, 10,000, 20,000, or 50,000 regions are analyzed.

In some embodiments, the variant occurs in a region of the genome selected from the group consisting of gene fusions, gene duplications, gene deletions, gene translocations, microsatellite regions, gene fragments or combination thereof. In some embodiments, the variant occurs in a region of the genome selected from the group consisting of genes, oncogenes, tumor suppressor genes, promoters, regulatory sequence elements, or combination thereof. In some embodiments, the variant is a nucleotide variant, single base substitution, small indel, transversion, translocation, inversion, deletion, truncation or gene truncation of 1, 2, 3, 4, 5, 6, 7, 8, 9, 10, 15 or 20 nucleotides in length.

In some embodiments, the methods further comprise correcting/normalizing/adjusting the quantity of mapped reads using the barcodes or unique properties of individual reads. In some embodiments, enumerating the reads is performed through enumeration of unique barcodes in each of the predefined regions and normalizing those numbers across at least a subset of predefined regions that were sequenced.

In some embodiments, samples at succeeding time intervals from the same subject are analyzed and compared to previous sample results. In some embodiments, the method further comprises amplifying the barcode-attached extracellular polynucleotides. In some embodiments, the methods further comprise determining partial copy number variation frequency, determining loss of heterozygosity, performing gene expression analysis, performing epigenetic analysis and/or performing hypermethylation analysis.

The disclosure also provides for a method comprising determining copy number variation or performing rare mutation analysis in a cell-free or substantially cell free sample obtained from a subject using multiplex sequencing.

In some embodiments, the multiplex sequencing comprises performing over 10,000 sequencing reactions. In some embodiments, the multiplex sequencing comprises simultaneously sequencing at least 10,000 different reads. In some embodiments, the multiplex sequencing comprising performing data analysis on at least 10,000 different reads across the genome. In some embodiments, the normalizing and detection is performed using one or more of hidden markov, dynamic programming, support vector machine, Bayesian or probabilistic modeling, trellis decoding, Viterbi decoding, expectation maximization, Kalman filtering, or neural network methodologies. In some embodiments, the methods further comprise monitoring disease progression, monitoring residual disease, monitoring therapy, diagnosing a condition, prognosing a condition, or selecting a therapy based on discovered variants for the subject. In some embodiments, a therapy is modified based on the most recent sample analysis. In some embodiments, the genetic profile of a tumor, infection or other tissue abnormality is inferred.

In some embodiments, the growth, remission or evolution of a tumor, infection or other tissue abnormality is monitored. In some embodiments, sequences related to the subject's immune system are analyzed and monitored at single instances or over time. In some embodiments, identification of a variant is followed up through an imaging test (e.g., CT, PET-CT, MRI, X-ray, ultrasound) for localization of the tissue abnormality suspected of causing the identified variant. In some embodiments, the analysis further comprises use of genetic data obtained from a tissue or tumor biopsy from the same patient. In some embodiments, the phylogenetics of a tumor, infection or other tissue abnormality is inferred. In some embodiments, the method further comprises performing population-based no-calling and identification of low-confidence regions. In some embodiments, obtaining the measurement data for the sequence coverage comprises measuring sequence coverage depth at every position of the genome. In some embodiments, correcting the measurement data for the sequence coverage bias comprises calculating window-averaged coverage. In some embodiments, correcting the measurement data for the sequence coverage bias comprises performing adjustments to account for GC bias in the library construction and sequencing process. In some embodiments, correcting the measurement data for the sequence coverage bias comprises performing adjustments based on additional weighting factor associated with individual mappings to compensate for bias.

In some embodiments, extracellular polynucleotide is derived from a diseased cell origin. In some embodiments, extracellular polynucleotide is derived from a healthy cell origin.

The disclosure also provides for a system comprising a computer readable medium for performing the following steps: selecting predefined regions in a genome; enumerating number of sequence reads in the predefined regions; normalizing the number of sequence reads across the predefined regions; and determining percent of copy number variation in the predefined regions.

In some embodiments, the entirety of the genome or at least 85% of the genome is analyzed. In some embodiments, the computer readable medium provides data on percent cancer DNA or RNA in plasma or serum to the end user. In some embodiments, the copy number variants identified are fractional (i.e., non-integer levels) due to heterogeneity in the sample. In some embodiments, enrichment of selected regions is performed. In some embodiments, copy number variation information is simultaneously extracted based on the methods described herein. In some embodiments, the methods comprise an initial step of polynucleotide bottlenecking to limit the number of starting initial copies or diversity of polynucleotides in the sample.

The disclosure also provides for a method for detecting a rare mutation in a cell-free or a substantially cell free sample obtained from a subject comprising: a) sequencing extracellular polynucleotides from a bodily sample of a subject, wherein each of the extracellular polynucleotides generate a plurality of sequencing reads; b) filtering out reads that fail to meet a set quality threshold; c) mapping sequence reads derived from the sequencing onto a reference sequence; d) identifying a subset of mapped sequence reads that align with a variant of the reference sequence at each mappable base position; e) for each mappable base position, calculating a ratio of (a) a number of mapped sequence reads that include a variant as compared to the reference sequence, to (b) a number of total sequence reads for each mappable base position; f) normalizing the ratios or frequency of variance for each mappable base position and determining potential rare variant(s) or other genetic alteration(s); and g) comparing the resulting number for each of the regions with potential rare variant(s) or mutation(s) to similarly derived numbers from a reference sample.

The disclosure also provides for a method comprising: a) providing at least one set of tagged parent polynucleotides, and for each set of tagged parent polynucleotides; b) amplifying the tagged parent polynucleotides in the set to produce a corresponding set of amplified progeny polynucleotides; c) sequencing a subset (including a proper subset) of the set of amplified progeny polynucleotides, to produce a set of sequencing reads; and d) collapsing the set of sequencing reads to generate a set of consensus sequences, each consensus sequence corresponding to a unique polynucleotide among the set of tagged parent polynucleotides.

In some embodiments, each polynucleotide in a set is mappable to a reference sequence. In some embodiments, the methods comprise providing a plurality of sets of tagged parent polynucleotides, wherein each set is mappable to a different mappable position in the reference sequence. In some embodiments, the method further comprises: e) analyzing the set of consensus sequences for each set of tagged parent molecules separately or in combination. In some embodiments, the method further comprises converting initial starting genetic material into the tagged parent polynucleotides. In some embodiments, the initial starting genetic material comprises no more than 100 ng of polynucleotides. In some embodiments, the method comprises bottlenecking the initial starting genetic material prior to converting. In some embodiments, the method comprises converting the initial starting genetic material into tagged parent polynucleotides with a conversion efficiency of at least 10%, at least 20%, at least 30%, at least 40%, at least 50%, at least 60%, at least 80% or at least 90%. In some embodiments, the converting comprises any of blunt-end ligation, sticky end ligation, molecular inversion probes, PCR, ligation-based PCR, single strand ligation and single strand circularization. In some embodiments, the initial starting genetic material is cell-free nucleic acid. In some embodiments, a plurality of the sets map to different mappable positions in a reference sequence from the same genome.

In some embodiments, each tagged parent polynucleotide in the set is uniquely tagged. In some embodiments, each set of parent polynucleotides is mappable to a position in a reference sequence, and the polynucleotides in each set are not uniquely tagged. In some embodiments, the generation of consensus sequences is based on information from the tag and/or at least one of (i) sequence information at the beginning (start) region of the sequence read, (ii) the end (stop) regions of the sequence read and (iii) the length of the sequence read.

In some embodiments, the method comprises sequencing a subset of the set of amplified progeny polynucleotides sufficient to produce sequence reads for at least one progeny from of each of at least 20%, at least 30%, at least 40%, at least 50%, at least 60%, at least 70%, at least 80%, at least 90%, at least 95%, at least 98%, at least 99%, at least 99.9% or at least 99.99% of unique polynucleotides in the set of tagged parent polynucleotides. In some embodiments, the at least one progeny is a plurality of progeny, e.g., at least 2, at least 5 or at least 10 progeny. In some embodiments, the number of sequence reads in the set of sequence reads is greater than the number of unique tagged parent polynucleotides in the set of tagged parent polynucleotides. In some embodiments, the subset of the set of amplified progeny polynucleotides sequenced is of sufficient size so that any nucleotide sequence represented in the set of tagged parent polynucleotides at a percentage that is the same as the percentage per-base sequencing error rate of the sequencing platform used, has at least a 50%, at least a 60%, at least a 70%, at least a 80%, at least a 90% at least a 95%, at least a 98%, at least a 99%, at least a 99.9% or at least a 99.99% chance of being represented among the set of consensus sequences.

In some embodiments, the method comprises enriching the set of amplified progeny polynucleotides for polynucleotides mapping to one or more selected mappable positions in a reference sequence by: (i) selective amplification of sequences from initial starting genetic material converted to tagged parent polynucleotides; (ii) selective amplification of tagged parent polynucleotides; (iii) selective sequence capture of amplified progeny polynucleotides; or (iv) selective sequence capture of initial starting genetic material.

In some embodiments, analyzing comprises normalizing a measure (e.g., number) taken from a set of consensus sequences against a measure taken from a set of consensus sequences from a control sample. In some embodiments, analyzing comprises detecting mutations, rare mutations, indels, copy number variations, transversions, translocations, inversion, deletions, aneuploidy, partial aneuploidy, polyploidy, chromosomal instability, chromosomal structure alterations, gene fusions, chromosome fusions, gene truncations, gene amplification, gene duplications, chromosomal lesions, DNA lesions, abnormal changes in nucleic acid chemical modifications, abnormal changes in epigenetic patterns, abnormal changes in nucleic acid methylation infection or cancer.

In some embodiments, the polynucleotides comprise DNA, RNA, a combination of the two, or DNA plus RNA-derived cDNA. In some embodiments, a certain subset of polynucleotides is selected for, or is enriched based on, polynucleotide length in base-pairs from the initial set of polynucleotides or from the amplified polynucleotides. In some embodiments, analysis further comprises detection and monitoring of an abnormality or disease within an individual, such as, infection and/or cancer. In some embodiments, the method is performed in combination with immune repertoire profiling. In some embodiments, the polynucleotides are extracted from a sample selected from the group consisting of blood, plasma, serum, urine, saliva, mucosal excretions, sputum, stool, and tears. In some embodiments, collapsing comprises detecting and/or correcting errors, nicks or lesions present in the sense or anti-sense strand of the tagged parent polynucleotides or amplified progeny polynucleotides.

The disclosure also provides for a method comprising detecting genetic variation in non-uniquely tagged initial starting genetic material with a sensitivity of at least 5%, at least 1%, at least 0.5%, at least 0.1% or at least 0.05%.

In some embodiments, the initial starting genetic material is provided in an amount less than 100 ng of nucleic acid, the genetic variation is copy number/heterozygosity variation and detecting is performed with sub-chromosomal resolution; e.g., at least 100 megabase resolution, at least 10 megabase resolution, at least 1 megabase resolution, at least 100 kilobase resolution, at least 10 kilobase resolution or at least 1 kilobase resolution. In some embodiments, the method comprises providing a plurality of sets of tagged parent polynucleotides, wherein each set is mappable to a different mappable position in a reference sequence. In some embodiments, the mappable position in the reference sequence is the locus of a tumor marker and analyzing comprises detecting the tumor marker in the set of consensus sequences.

In some embodiments, the tumor marker is present in the set of consensus sequences at a frequency less than the error rate introduced at the amplifying step. In some embodiments, the at least one set is a plurality of sets, and the mappable position of the reference sequence comprise a plurality of mappable positions in the reference sequence, each of which mappable position is the locus of a tumor marker. In some embodiments, analyzing comprises detecting copy number variation of consensus sequences between at least two sets of parent polynucleotides. In some embodiments, analyzing comprises detecting the presence of sequence variations compared with the reference sequences.

In some embodiments, analyzing comprises detecting the presence of sequence variations compared with the reference sequences and detecting copy number variation of consensus sequences between at least two sets of parent polynucleotides. In some embodiments, collapsing comprises: (i) grouping sequences reads sequenced from amplified progeny polynucleotides into families, each family amplified from the same tagged parent polynucleotide; and (ii) determining a consensus sequence based on sequence reads in a family.

The disclosure also provides for a system comprising a computer readable medium for performing the following steps: a) accepting at least one set of tagged parent polynucleotides, and for each set of tagged parent polynucleotides; b) amplifying the tagged parent polynucleotides in the set to produce a corresponding set of amplified progeny polynucleotides; c) sequencing a subset (including a proper subset) of the set of amplified progeny polynucleotides, to produce a set of sequencing reads; d) collapsing the set of sequencing reads to generate a set of consensus sequences, each consensus sequence corresponding to a unique polynucleotide among the set of tagged parent polynucleotides and, optionally, e) analyzing the set of consensus sequences for each set of tagged parent molecules.

The disclosure also provides for a method comprising detecting the presence or absence of genetic alteration or amount of genetic variation in an individual, wherein the detecting is performed with the aid of sequencing of cell-free nucleic acid, wherein at least 10% of the individual's genome is sequenced.

The disclosure also provides for a method comprising detecting the presence or absence of genetic alteration or amount of genetic variation in an individual, wherein the detecting is performed with the aid of sequencing of cell-free nucleic acid, wherein at least 20% of the individual's genome is sequenced.

The disclosure also provides for a method comprising detecting the presence or absence of genetic alteration or amount of genetic variation in an individual, wherein the detecting is performed with the aid of sequencing of cell-free nucleic acid, wherein at least 30% of the individual's genome is sequenced.

The disclosure also provides for a method comprising detecting the presence or absence of genetic alteration or amount of genetic variation in an individual, wherein the detecting is performed with the aid of sequencing of cell-free nucleic acid, wherein at least 40% of the individual's genome is sequenced.

The disclosure also provides for a method comprising detecting the presence or absence of genetic alteration or amount of genetic variation in an individual, wherein the detecting is performed with the aid of sequencing of cell-free nucleic acid, wherein at least 50% of the individual's genome is sequenced.

The disclosure also provides for a method comprising detecting the presence or absence of genetic alteration or amount of genetic variation in an individual, wherein the detecting is performed with the aid of sequencing of cell-free nucleic acid, wherein at least 60% of the individual's genome is sequenced.

The disclosure also provides for a method comprising detecting the presence or absence of genetic alteration or amount of genetic variation in an individual, wherein the detecting is performed with the aid of sequencing of cell-free nucleic acid, wherein at least 70% of the individual's genome is sequenced.

The disclosure also provides for a method comprising detecting the presence or absence of genetic alteration or amount of genetic variation in an individual, wherein the detecting is performed with the aid of sequencing of cell-free nucleic acid, wherein at least 80% of the individual's genome is sequenced.

The disclosure also provides for a method comprising detecting the presence or absence of genetic alteration or amount of genetic variation in an individual, wherein the detecting is performed with the aid of sequencing of cell-free nucleic acid, wherein at least 90% of the individual's genome is sequenced.

The disclosure also provides for a method comprising detecting the presence or absence of genetic alteration and amount of genetic variation in an individual, wherein the detecting is performed with the aid of sequencing of cell-free nucleic acid, wherein at least 10% of the individual's genome is sequenced.

The disclosure also provides for a method comprising detecting the presence or absence of genetic alteration and amount of genetic variation in an individual, wherein the detecting is performed with the aid of sequencing of cell-free nucleic acid, wherein at least 20% of the individual's genome is sequenced.

The disclosure also provides for a method comprising detecting the presence or absence of genetic alteration and amount of genetic variation in an individual, wherein the detecting is performed with the aid of sequencing of cell-free nucleic acid, wherein at least 30% of the individual's genome is sequenced.

The disclosure also provides for a method comprising detecting the presence or absence of genetic alteration and amount of genetic variation in an individual, wherein the detecting is performed with the aid of sequencing of cell-free nucleic acid, wherein at least 40% of the individual's genome is sequenced.

The disclosure also provides for a method comprising detecting the presence or absence of genetic alteration and amount of genetic variation in an individual, wherein the detecting is performed with the aid of sequencing of cell-free nucleic acid, wherein at least 50% of the individual's genome is sequenced.

The disclosure also provides for a method comprising detecting the presence or absence of genetic alteration and amount of genetic variation in an individual, wherein the detecting is performed with the aid of sequencing of cell-free nucleic acid, wherein at least 60% of the individual's genome is sequenced.

The disclosure also provides for a method comprising detecting the presence or absence of genetic alteration and amount of genetic variation in an individual, wherein the detecting is performed with the aid of sequencing of cell-free nucleic acid, wherein at least 70% of the individual's genome is sequenced.

The disclosure also provides for a method comprising detecting the presence or absence of genetic alteration and amount of genetic variation in an individual, wherein the detecting is performed with the aid of sequencing of cell-free nucleic acid, wherein at least 80% of the individual's genome is sequenced.

The disclosure also provides for a method comprising detecting the presence or absence of genetic alteration and amount of genetic variation in an individual, wherein the detecting is performed with the aid of sequencing of cell-free nucleic acid, wherein at least 90% of the individual's genome is sequenced.

In some embodiments, the genetic alteration is copy number variation or one or more rare mutations. In some embodiments, the genetic variation comprises one or more causal variants and one or more polymorphisms. In some embodiments, the genetic alteration and/or amount of genetic variation in the individual may be compared to a genetic alteration and/or amount of genetic variation in one or more individuals with a known disease. In some embodiments, the genetic alteration and/or amount of genetic variation in the individual may be compared to a genetic alteration and/or amount of genetic variation in one or more individuals, without a disease. In some embodiments, the cell-free nucleic acid is DNA. In some embodiments, the cell-free nucleic acid is RNA. In some embodiments, the cell-free nucleic acid is DNA and RNA. In some embodiments, the disease is cancer or pre-cancer. In some embodiments, the method further comprising diagnosis or treatment of a disease.

The disclosure also provides for a method comprising: a) providing at least one set of tagged parent polynucleotides, and for each set of tagged parent polynucleotides; b) amplifying the tagged parent polynucleotides in the set to produce a corresponding set of amplified progeny polynucleotides; c) sequencing a subset (including a proper subset) of the set of amplified progeny polynucleotides, to produce a set of sequencing reads; d) collapsing the set of sequencing reads to generate a set of consensus sequences, each consensus sequence corresponding to a unique polynucleotide among the set of tagged parent polynucleotides; and e) filtering out from among the consensus sequences those that fail to meet a quality threshold.

In some embodiments, the quality threshold considers a number of sequence reads from amplified progeny polynucleotides collapsed into a consensus sequence. In some embodiments, the quality threshold considers a number of sequence reads from amplified progeny polynucleotides collapsed into a consensus sequence.

The disclosure also provides for a system comprising a computer readable medium for performing the methods described herein.

The disclosure also provides for a method comprising: a) providing at least one set of tagged parent polynucleotides, wherein each set maps to a different mappable position in a reference sequence in one or more genomes, and, for each set of tagged parent polynucleotides; i) amplifying the first polynucleotides to produce a set of amplified polynucleotides; ii) sequencing a subset of the set of amplified polynucleotides, to produce a set of sequencing reads; and iii) collapsing the sequence reads by: (1) grouping sequences reads sequenced from amplified progeny polynucleotides into families, each family amplified from the same tagged parent polynucleotide.

In some embodiments, collapsing further comprises determining a quantitative measure of sequence reads in each family. In some embodiments, the method further comprises: a) determining a quantitative measure of unique families; and b) based on (1) the quantitative measure of unique families and (2) the quantitative measure of sequence reads in each group, inferring a measure of unique tagged parent polynucleotides in the set. In some embodiments, inferring is performed using statistical or probabilistic models. In some embodiments, the at least one set is a plurality of sets. In some embodiments, the method further comprises correcting for amplification or representational bias between the two sets. In some embodiments, the method further comprises using a control or set of control samples to correct for amplification or representational biases between the two sets. In some embodiments, the method further comprises determining copy number variation between the sets.

In some embodiments, the method further comprises: d) determining a quantitative measure of polymorphic forms among the families; and e) based on the determined quantitative measure of polymorphic forms, inferring a quantitative measure of polymorphic forms in the number of inferred unique tagged parent polynucleotides. In some embodiments, polymorphic forms include but are not limited to: substitutions, insertions, deletions, inversions, microsatellite changes, transversions, translocations, fusions, methylation, hypermethylation, hyrdroxymethylation, acetylation, epigenetic variants, regulatory-associated variants or protein binding sites.

In some embodiments, the sets derive from a common sample, and the method further comprises: d) inferring copy number variation for the plurality of sets based on a comparison of the inferred number of tagged parent polynucleotides in each set mapping to each of a plurality of mappable positions in a reference sequence. In some embodiments, the original number of polynucleotides in each set is further inferred. In some embodiments, at least a subset of the tagged parent polynucleotides in each set are non-uniquely tagged.

The disclosure also provides for a method of determining copy number variation in a sample that includes polynucleotides, the method comprising: a) providing at least two sets of first polynucleotides, wherein each set maps to a different mappable position in a reference sequence in a genome, and, for each set of first polynucleotides; (i) amplifying the polynucleotides to produce a set of amplified polynucleotides; (ii) sequencing a subset of the set of amplified polynucleotides, to produce a set of sequencing reads; (iii) grouping sequences reads sequenced from amplified polynucleotides into families, each family amplified from the same first polynucleotide in the set; (iv) inferring a quantitative measure of families in the set; and b) determining copy number variation by comparing the quantitative measure of families in each set.

The disclosure also provides for a method of inferring frequency of sequence calls in a sample of polynucleotides comprising: a) providing at least one set of first polynucleotides, wherein each set maps to a different mappable position in a reference sequence in one or more genomes, and, for each set of first polynucleotides; (i) amplifying the first polynucleotides to produce a set of amplified polynucleotides; (ii) sequencing a subset of the set of amplified polynucleotides, to produce a set of sequencing reads; (iii) grouping the sequence reads into families, each family comprising sequence reads of amplified polynucleotides amplified from the same first polynucleotide; b) inferring, for each set of first polynucleotides, a call frequency for one or more bases in the set of first polynucleotides, wherein inferring comprises: (i) assigning, for each family, confidence score for each of a plurality of calls, the confidence score taking into consideration a frequency of the call among members of the family; and (ii) estimating a frequency of the one or more calls taking into consideration the confidence scores of the one or more calls assigned to each family.

The disclosure also provides for a method of communicating sequence information about at least one individual polynucleotide molecule, comprising: a) providing at least one individual polynucleotide molecule; b) encoding sequence information in the at least one individual polynucleotide molecule to produce a signal; c) passing at least part of the signal through a channel to produce a received signal comprising nucleotide sequence information about the at least one individual polynucleotide molecule, wherein the received signal comprises noise and/or distortion; d) decoding the received signal to produce a message comprising sequence information about the at least one individual polynucleotide molecule, wherein decoding reduces noise and/or distortion about each individual polynucleotide in the message; and e) providing the message comprising sequence information about the at least one individual polynucleotide molecule to a recipient.

In some embodiments, the noise comprises incorrect nucleotide calls. In some embodiments, distortion comprises uneven amplification of the individual polynucleotide molecule compared with other individual polynucleotide molecules. In some embodiments, distortion results from amplification or sequencing bias. In some embodiments, the at least one individual polynucleotide molecule is a plurality of individual polynucleotide molecules, and decoding produces a message about each molecule in the plurality. In some embodiments, encoding comprises amplifying the at least one individual polynucleotide molecule, which has optionally been tagged, wherein the signal comprises a collection of amplified molecules. In some embodiments, the channel comprises a polynucleotide sequencer and the received signal comprises sequence reads of a plurality of polynucleotides amplified from the at least one individual polynucleotide molecule. In some embodiments, decoding comprises grouping sequence reads of amplified molecules amplified from each of the at least one individual polynucleotide molecules. In some embodiments, the decoding consists of a probabilistic or statistical method of filtering the generated sequence signal.

In some embodiments, the polynucleotides are derived from tumor genomic DNA or RNA. In some embodiments, the polynucleotides are derived from cell-free polynucleotides, exosomal polynucleotides, bacterial polynucleotides or viral polynucleotides. In some embodiments of any of the methods herein, the method further comprises the detection and/or association of affected molecular pathways. In some embodiments of any of the methods herein, the method further comprises serial monitoring of the health or disease state of an individual. In some embodiments the phylogeny of a genome associated with a disease within an individual is inferred. In some embodiments, any of the methods described herein further comprise diagnosis, monitoring or treatment of a disease. In some embodiments, the treatment regimen is selected or modified based on detected polymorphic forms or CNVs or associated pathways. In some embodiments, the treatment comprises of a combination therapy. In some embodiments, the diagnosis further comprises localizing the disease using a radiographic technique, such as, a CT-Scan, PET-CT, MRI, Ultrasound, Ultraound with microbubbles, etc.

The disclosure also provides for a computer readable medium comprising non-transitory machine-executable code that, upon execution by a computer processor, implements a method, the method comprising: selecting predefined regions in a genome; accessing sequence reads and enumerating number of sequence reads in the predefined regions; normalizing the number of sequence reads across the predefined regions; and determining percent of copy number variation in the predefined regions.

The disclosure also provides for a computer readable medium comprising non-transitory machine-executable code that, upon execution by a computer processor, implements a method, the method comprising: accessing a data file comprising a plurality of sequencing reads; filtering out reads that fail to meet a set threshold; mapping sequence reads derived from the sequencing onto a reference sequence; identifying a subset of mapped sequence reads that align with a variant of the reference sequence at each mappable base position; for each mappable base position, calculating a ratio of (a) a number of mapped sequence reads that include a variant as compared to the reference sequence, to (b) a number of total sequence reads for each mappable base position; normalizing the ratios or frequency of variance for each mappable base position and determining potential rare variant(s) or other genetic alteration(s); and comparing the resulting number for each of the regions with potential rare variant(s) or mutation(s) to similarly derived numbers from a reference sample.

The disclosure also provides for a computer readable medium comprising non-transitory machine-executable code that, upon execution by a computer processor, implements a method, the method comprising: a) accessing a data file comprising a plurality of sequencing reads, wherein the sequence reads derive from a set of progeny polynucleotides amplified from at least one set of tagged parent polynucleotides; and b) collapsing the set of sequencing reads to generate a set of consensus sequences, each consensus sequence corresponding to a unique polynucleotide among the set of tagged parent polynucleotides.

The disclosure also provides for a computer readable medium comprising non-transitory machine-executable code that, upon execution by a computer processor, implements a method, the method comprising: a) accessing a data file comprising a plurality of sequencing reads, wherein the sequence reads derive from a set of progeny polynucleotides amplified from at least one set of tagged parent polynucleotides; b) collapsing the set of sequencing reads to generate a set of consensus sequences, each consensus sequence corresponding to a unique polynucleotide among the set of tagged parent polynucleotides; and c) filtering out from among the consensus sequences those that fail to meet a quality threshold.

A computer readable medium comprising non-transitory machine-executable code that, upon execution by a computer processor, implements a method, the method comprising: a) accessing a data file comprising a plurality of sequencing reads, wherein the sequence reads derive from a set of progeny polynucleotides amplified from at least one set of tagged parent polynucleotides; and i) collapsing the sequence reads by: (1) grouping sequences reads sequenced from amplified progeny polynucleotides into families, each family amplified from the same tagged parent polynucleotide and, optionally, (2) determining a quantitative measure of sequence reads in each family.

In some embodiments, the executable code, upon execution by a computer processor, further performs the steps of: b) determining a quantitative measure of unique families; and c) based on (1) the quantitative measure of unique families and (2) the quantitative measure of sequence reads in each group, inferring a measure of unique tagged parent polynucleotides in the set.

In some embodiments, the executable code, upon execution by a computer processor, further performs the steps of: d) determining a quantitative measure of polymorphic forms among the families; and e) based on the determined quantitative measure of polymorphic forms, inferring a quantitative measure of polymorphic forms in the number of inferred unique tagged parent polynucleotides.

The disclosure also provides for a computer readable medium comprising non-transitory machine-executable code that, upon execution by a computer processor, implements a method, the method comprising: a) accessing a data file comprising a plurality of sequencing reads, wherein the sequence reads derive from a set of progeny polynucleotides amplified from at least one set of tagged parent polynucleotides grouping sequences reads sequenced from amplified polynucleotides into families, each family amplified from the same first polynucleotide in the set; b) inferring a quantitative measure of families in the set; and c) determining copy number variation by comparing the quantitative measure of families in each set.

The disclosure also provides for a computer readable medium comprising non-transitory machine-executable code that, upon execution by a computer processor, implements a method, the method comprising: a) accessing a data file comprising a plurality of sequencing reads, wherein the sequence reads derive from a set of progeny polynucleotides amplified from at least one set of tagged parent polynucleotides grouping the sequence reads into families, each family comprising sequence reads of amplified polynucleotides amplified from the same first polynucleotide; b) inferring, for each set of first polynucleotides, a call frequency for one or more bases in the set of first polynucleotides, wherein inferring comprises: c) assigning, for each family, confidence score for each of a plurality of calls, the confidence score taking into consideration a frequency of the call among members of the family; and d) estimating a frequency of the one or more calls taking into consideration the confidence scores of the one or more calls assigned to each family.

The disclosure also provides for a computer readable medium comprising non-transitory machine-executable code that, upon execution by a computer processor, implements a method, the method comprising: a) accessing a data file comprising a received signal that comprises endoded sequence information from at least one individual polynucleotide molecule wherein the received signal comprises noise and/or distortion; b) decoding the received signal to produce a message comprising sequence information about the at least one individual polynucleotide molecule, wherein decoding reduces noise and/or distortion about each individual polynucleotide in the message; and c) writing the message comprising sequence information about the at least one individual polynucleotide molecule to a computer file.

The disclosure also provides for a computer readable medium comprising non-transitory machine-executable code that, upon execution by a computer processor, implements a method, the method comprising: a) accessing a data file comprising a plurality of sequencing reads, wherein the sequence reads derive from a set of progeny polynucleotides amplified from at least one set of tagged parent polynucleotides; b) collapsing the set of sequencing reads to generate a set of consensus sequences, each consensus sequence corresponding to a unique polynucleotide among the set of tagged parent polynucleotides; and c) filtering out from among the consensus sequences those that fail to meet a quality threshold.

The disclosure also provides for a computer readable medium comprising non-transitory machine-executable code that, upon execution by a computer processor, implements a method, the method comprising: a) accessing a data file comprising a plurality of sequencing reads, wherein the sequence reads derive from a set of progeny polynucleotides amplified from at least one set of tagged parent polynucleotides; and b) collapsing the sequence reads by: (i) grouping sequences reads sequenced from amplified progeny polynucleotides into families, each family amplified from the same tagged parent polynucleotide; and (ii) optionally, determining a quantitative measure of sequence reads in each family.

In some embodiments, the executable code, upon execution by a computer processor, further performs the steps of: d) determining a quantitative measure of unique families; e) based on (1) the quantitative measure of unique families and (2) the quantitative measure of sequence reads in each group, inferring a measure of unique tagged parent polynucleotides in the set.

In some embodiments, the executable code, upon execution by a computer processor, further performs the steps of: e) determining a quantitative measure of polymorphic forms among the families; and f) based on the determined quantitative measure of polymorphic forms, inferring a quantitative measure of polymorphic forms in the number of inferred unique tagged parent polynucleotides.

In some embodiments, the executable code, upon execution by a computer processor, further performs the steps of: e) inferring copy number variation for the plurality of sets based on a comparison of the inferred number of tagged parent polynucleotides in each set mapping to each of a plurality of reference sequences.

The disclosure also provides for a computer readable medium comprising non-transitory machine-executable code that, upon execution by a computer processor, implements a method, the method comprising: a) accessing a data file comprising a plurality of sequencing reads, wherein the sequence reads derive from a set of progeny polynucleotides amplified from at least one set of tagged parent polynucleotides; b) grouping sequences reads sequenced from amplified polynucleotides into families, each family amplified from the same first polynucleotide in the set; c) inferring a quantitative measure of families in the set; d) determining copy number variation by comparing the quantitative measure of families in each set.

The disclosure also provides for a computer readable medium comprising non-transitory machine-executable code that, upon execution by a computer processor, implements a method, the method comprising: accessing a data file comprising a plurality of sequencing reads, wherein the sequence reads derive from a set of progeny polynucleotides amplified from at least one set of tagged parent polynucleotides grouping the sequence reads into families, each family comprising sequence reads of amplified polynucleotides amplified from the same first polynucleotide; and inferring, for each set of first polynucleotides, a call frequency for one or more bases in the set of first polynucleotides, wherein inferring comprises: (i) assigning, for each family, confidence score for each of a plurality of calls, the confidence score taking into consideration a frequency of the call among members of the family; and (ii) estimating a frequency of the one or more calls taking into consideration the confidence scores of the one or more calls assigned to each family.

The disclosure also provides for a composition comprising between 100 and 100,000 human haploid genome equivalents of cfDNA polynucleotides, wherein the polynucleotides are tagged with between 2 and 1,000,000 unique identifiers.

In some embodiments, the composition comprises between 1000 and 50,000 haploid human genome equivalents of cfDNA polynucleotides, wherein the polynucleotides are tagged with between 2 and 1,000 unique identifiers. In some embodiments, the unique identifiers comprise nucleotide barcodes. The disclosure also provides for a method comprising: a) providing a sample comprising between 100 and 100,000 haploid human genome equivalents of cfDNA polynucleotides; and b) tagging the polynucleotides with between 2 and 1,000,000 unique identifiers.

The disclosure also provides for a method comprising: a) providing a sample comprising a plurality of human haploid genome equivalents of fragmented polynucleotides; b) determining z, wherein z is a measure of central tendency (e.g., mean, median or mode) of expected number of duplicate polynucleotides starting at any position in the genome, wherein duplicate polynucleotides have the same start and stop positions; and c) tagging polynucleotides in sample with n unique identifiers, wherein n is between 2 and 100,000*z, 2 and 10,000*z, 2 and 1,000*z or 2 and 100*z. The disclosure also provides for a method comprising: a) providing at least one set of tagged parent polynucleotides, and for each set of tagged parent polynucleotides; b) producing a plurality of sequence reads for each tagged parent polynucleotide in the set to produce a set of sequencing reads; and c) collapsing the set of sequencing reads to generate a set of consensus sequences, each consensus sequence corresponding to a unique polynucleotide among the set of tagged parent polynucleotides.

The disclosure also provides for a system comprising a computer readable medium comprising machine-executable code as described herein. The disclosure also provides for a system comprising a computer readable medium comprising machine-executable code that, upon execution by a computer processor, implements a method as described herein.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of a system and methods of this disclosure are set forth with particularity in the appended claims. A better understanding of the features and advantages of this disclosure will be obtained by reference to the following detailed description that sets forth illustrative embodiments, in which the principles of a systems and methods of this disclosure are utilized, and the accompanying drawings of which:

DETAILED DESCRIPTION OF THE INVENTION

I. General Overview

Figure 1:
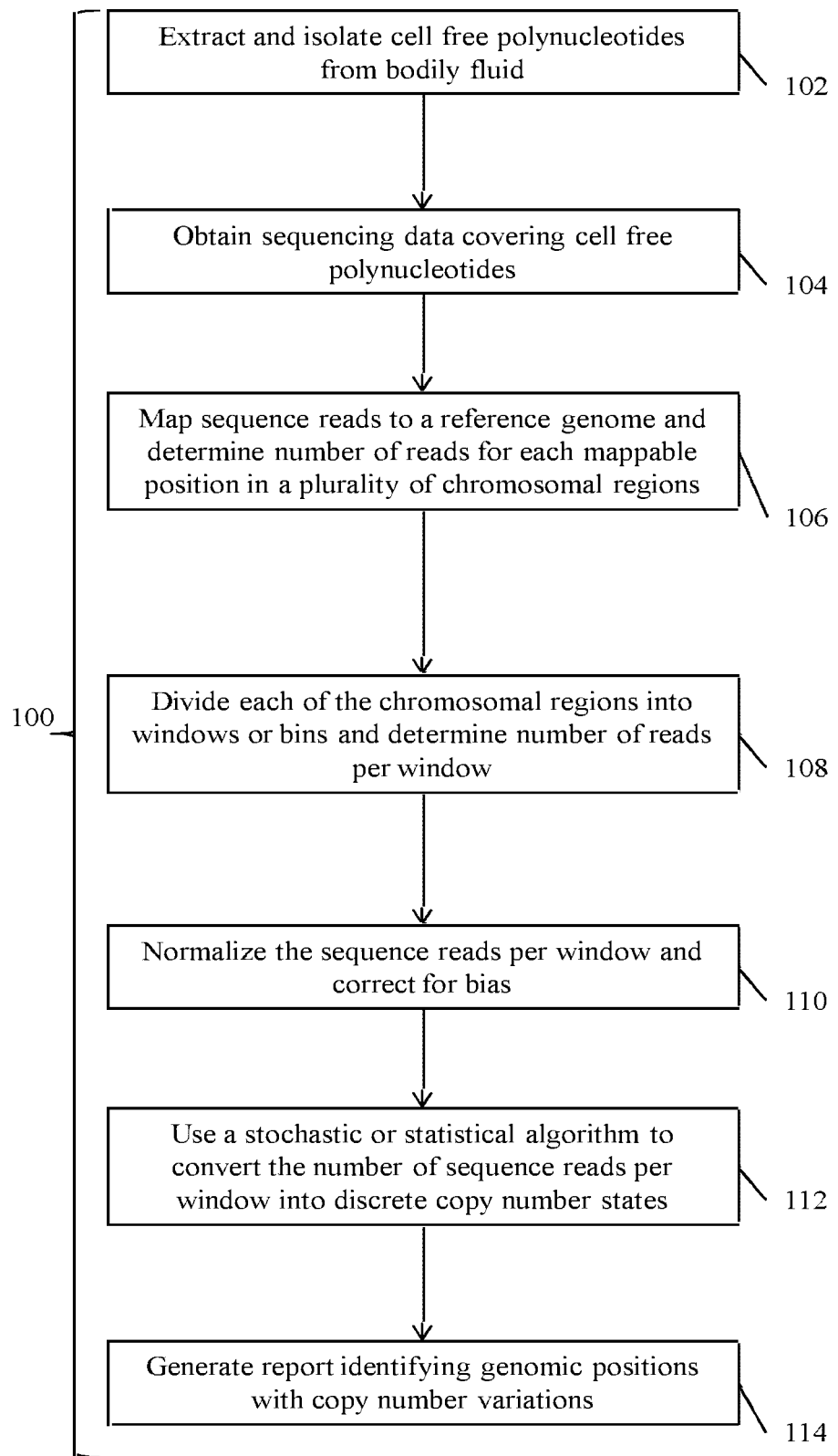
FIG. 1 is a flow chart representation of a method of detection of copy number variation using a single sample.

The present disclosure provides a system and method for the detection of rare mutations (e.g., single or multiple nucleotide variations) and copy number variations in cell free polynucleotides. Generally, the systems and methods comprise sample preparation, or the extraction and isolation of cell free polynucleotide sequences from a bodily fluid; subsequent sequencing of cell free polynucleotides by techniques known in the art; and application of bioinformatics tools to detect rare mutations and copy number variations as compared to a reference. The systems and methods also may contain a database or collection of different rare mutations or copy number variation profiles of different diseases, to be used as additional references in aiding detection of rare mutations (e.g., single nucleotide variation profiling), copy number variation profiling or general genetic profiling of a disease.

The systems and methods may be particularly useful in the analysis of cell free DNAs. In some cases, cell free DNA are extracted and isolated from a readily accessible bodily fluid such as blood. For example, cell free DNA can be extracted using a variety of methods known in the art, including but not limited to isopropanol precipitation and/or silica based purification. Cell free DNA may be extracted from any number of subjects, such as subjects without cancer, subjects at risk for cancer, or subjects known to have cancer (e.g. through other means).

Following the isolation/extraction step, any of a number of different sequencing operations may be performed on the cell free polynucleotide sample. Samples may be processed before sequencing with one or more reagents (e.g., enzymes, unique identifiers (e.g., barcodes), probes, etc.). In some cases if the sample is processed with a unique identifier such as a barcode, the samples or fragments of samples may be tagged individually or in subgroups with the unique identifier. The tagged sample may then be used in a downstream application such as a sequencing reaction by which individual molecules may be tracked to parent molecules.

After sequencing data of cell free polynucleotide sequences is collected, one or more bioinformatics processes may be applied to the sequence data to detect genetic features or aberrations such as copy number variation, rare mutations (e.g., single or multiple nucleotide variations) or changes in epigenetic markers, including but not limited to methylation profiles. In some cases, in which copy number variation analysis is desired, sequence data may be: 1) aligned with a reference genome; 2) filtered and mapped; 3) partitioned into windows or bins of sequence; 4) coverage reads counted for each window; 5) coverage reads can then be normalized using a stochastic or statistical modeling algorithm; 6) and an output file can be generated reflecting discrete copy number states at various positions in the genome. In other cases, in which rare mutation analysis is desired, sequence data may be 1) aligned with a reference genome; 2) filtered and mapped; 3) frequency of variant bases calculated based on coverage reads for that specific base; 4) variant base frequency normalized using a stochastic, statistical or probabilistic modeling algorithm; 5) and an output file can be generated reflecting mutation states at various positions in the genome.

A variety of different reactions and/or operations may occur within the systems and methods disclosed herein, including but not limited to: nucleic acid sequencing, nucleic acid quantification, sequencing optimization, detecting gene expression, quantifying gene expression, genomic profiling, cancer profiling, or analysis of expressed markers. More-over, the systems and methods have numerous medical applications. For example, it may be used for the identification, detection, diagnosis, treatment, staging of, or risk prediction of various genetic and non-genetic diseases and disorders including cancer. It may be used to assess subject response to different treatments of said genetic and non-genetic diseases, or provide information regarding disease progression and prognosis.

Polynucleotide sequencing can be compared with a problem in communication theory. An initial individual polynucleotide or ensemble of polynucleotides is thought of as an original message. Tagging and/or amplifying can be thought of as encoding the original message into a signal. Sequencing can be thought of as communication channel. The output of a sequencer, e.g., sequence reads, can be thought of as a received signal. Bioinformatic processing can be thought of as a receiver that decodes the received signal to produce a transmitted message, e.g., a nucleotide sequence or sequences. The received signal can include artifacts, such as noise and distortion. Noise can be thought of as an unwanted random addition to a signal. Distortion can be thought of as an alteration in the amplitude of a signal or portion of a signal.

Noise can be introduced through errors in copying and/or reading a polynucleotide. For example, in a sequencing process a single polynucleotide can first be subject to amplification. Amplification can introduce errors, so that a subset of the amplified polynucleotides may contain, at a particular locus, a base that is not the same as the original base at that locus. Furthermore, in the reading process a base at any particular locus may be read incorrectly. As a consequence, the collection of sequence reads can include a certain percentage of base calls at a locus that are not the same as the original base. In typical sequencing technologies this error rate can be in the single digits, e.g., 2%-3%. When a collection of molecules that are all presumed to have the same sequence are sequenced, this noise is sufficiently small that one can identify the original base with high reliability.

However, if a collection of parent polynucleotides includes a subset of polynucleotides having sequence variants at a particular locus, noise can be a significant problem. This can be the case, for example, when cell free DNA includes not only germline DNA, but DNA from another source, such as fetal DNA or DNA from a cancer cell. In this case, if the frequency of molecules with sequence variants is in the same range as the frequency of errors introduced by the sequencing process, then true sequence variants may not be distinguishable from noise. This could interfere, for example, with detecting sequence variants in a sample.

Distortion can be manifested in the sequencing process as a difference in signal strength, e.g., total number of sequence reads, produced by molecules in a parent population at the same frequency. Distortion can be introduced, for example, through amplification bias, GC bias, or sequencing bias. This could interfere with detecting copy number variation in a sample. GC bias results in the uneven representation of areas rich or poor in GC content in the sequence reading.

This invention provides methods of reducing sequencing artifacts, such as noise and/or distortion, in a polynucleotide sequencing process. Grouping sequence reads into families derived from original individual molecules can reduce noise and/or distortion from a single individual molecule or from an ensemble of molecules. With respect to a single molecule, grouping reads into a family reduces distortion by, for example, indicating that many sequence reads actually represent a single molecule rather than many different molecules. Collapsing sequence reads into a consensus sequence is one way to reduce noise in the received message from one molecule. Using probabilistic functions that convert received frequencies is another way. With respect to an ensemble of molecules, grouping reads into families and determining a quantitative measure of the families reduces distortion, for example, in the quantity of molecules at each of a plurality of different loci. Again, collapsing sequence reads of different families into consensus sequences eliminate errors introduced by amplification and/or sequencing error. Furthermore, determining frequencies of base calls based on probabilities derived from family information also reduces noise in the received message from an ensemble of molecules.

Methods of reducing noise and/or distortion from a sequencing process are known. These include, for example, filtering sequences, e.g., requiring them to meet a quality threshold, or reducing GC bias. Such methods typically are performed on the collection of sequence reads that are the output of a sequencer, and can be performed sequence read-by-sequence read, without regard for family structure (sub-collections of sequences derived from a single original parent molecule). Certain methods of this invention reduce noise and distortion by reducing noise and/or distortion within families of sequence reads, that is, operating on sequence reads grouped into families derived from a single parent polynucleotide molecule. Signal artifact reduction at the family level can produce significantly less noise and distortion in the ultimate message that is provided than artifact reduction performed at a sequence read-by-sequence read level or on sequencer output as a whole.

The present disclosure further provides methods and systems for detecting with high sensitivity genetic variation in a sample of initial genetic material. The methods involve using one or both of the following tools: First, the efficient conversion of individual polynucleotides in a sample of initial genetic material into sequence-ready tagged parent polynucleotides, so as to increase the probability that individual polynucleotides in a sample of initial genetic material will be represented in a sequence-ready sample. This can produce sequence information about more polynucleotides in the initial sample. Second, high yield generation of consensus sequences for tagged parent polynucleotides by high rate sampling of progeny polynucleotides amplified from the tagged parent polynucleotides, and collapsing of generated sequence reads into consensus sequences representing sequences of parent tagged polynucleotides. This can reduce noise introduced by amplification bias and/or sequencing errors, and can increase sensitivity of detection. Collapsing is performed on a plurality of sequence reads, generated either from reads of amplified molecules, or multiple reads of a single molecule.

Sequencing methods typically involve sample preparation, sequencing of polynucleotides in the prepared sample to produce sequence reads and bioinformatic manipulation of the sequence reads to produce quantitative and/or qualitative genetic information about the sample. Sample preparation typically involves converting polynucleotides in a sample into a form compatible with the sequencing platform used. This conversion can involve tagging polynucleotides. In certain embodiments of this invention the tags comprise polynucleotide sequence tags. Conversion methodologies used in sequencing may not be 100% efficient. For example, it is not uncommon to convert polynucleotides in a sample with a conversion efficiency of about 1-5%, that is, about 1-5% of the polynucleotides in a sample are converted into tagged polynucleotides. Polynucleotides that are not converted into tagged molecules are not represented in a tagged library for sequencing. Accordingly, polynucleotides having genetic variants represented at low frequency in the initial genetic material may not be represented in the tagged library and, therefore may not be sequenced or detected. By increasing conversion efficiency, the probability that a rare polynucleotide in the initial genetic material will be represented in the tagged library and, consequently, detected by sequencing is increased. Furthermore, rather than directly address the low conversion efficiency issue of library preparation, most protocols to date call for greater than 1 microgram of DNA as input material. However, when input sample material is limited or detection of polynucleotides with low representation is desired, high conversion efficiency can efficiently sequence the sample and/or to adequately detect such polynucleotides.

This disclosure provides methods of converting initial polynucleotides into tagged polynucleotides with a conversion efficiency of at least 10%, at least 20%, at least 30%, at least 40%, at least 50%, at least 60%, at least 80% or at least 90%. The methods involve, for example, using any of blunt-end ligation, sticky end ligation, molecular inversion probes, PCR, ligation-based PCR, multiplex PCR, single strand ligation and single strand circularization. The methods can also involve limiting the amount of initial genetic material. For example, the amount of initial genetic material can be less than 1 ug, less than 100 ng or less than 10 ng. These methods are described in more detail herein.

Obtaining accurate quantitative and qualitative information about polynucleotides in a tagged library can result in a more sensitive characterization of the initial genetic material. Typically, polynucleotides in a tagged library are amplified and the resulting amplified molecules are sequenced. Depending on the throughput of the sequencing platform used, only a subset of the molecules in the amplified library produce sequence reads. So, for example, the number of amplified molecules sampled for sequencing may be about only 50% of the unique polynucleotides in the tagged library. Furthermore, amplification may be biased in favor of or against certain sequences or certain members of the tagged library. This may distort quantitative measurement of sequences in the tagged library. Also, sequencing platforms can introduce errors in sequencing. For example, sequences can have a per-base error rate of 0.5-1%. Amplification bias and sequencing errors introduce noise into the final sequencing product. This noise can diminish sensitivity of detection. For example, sequence variants whose frequency in the tagged population is less than the sequencing error rate can be mistaken for noise. Also, by providing reads of sequences in greater or less amounts than their actual number in a population, amplification bias can distort measurements of copy number variation. Alternatively, a plurality of sequence reads from a single polynucleotide can be produced without amplification. This can be done, for example, with nanopore methods.

This disclosure provides methods of accurately detecting and reading unique polynucleotides in a tagged pool. In certain embodiments this disclosure provides sequence-tagged polynucleotides that, when amplified and sequenced, or when sequenced a plurality of times to produce a plurality of sequence reads, provide information that allowed the tracing back, or collapsing, of progeny polynucleotides to the unique tag parent polynucleotide molecule. Collapsing families of amplified progeny polynucleotides reduces amplification bias by providing information about original unique parent molecules. Collapsing also reduces sequencing errors by eliminating from sequencing data mutant sequences of progeny molecules.

Detecting and reading unique polynucleotides in the tagged library can involve two strategies. In one strategy a sufficiently large subset of the amplified progeny polynucleotide pool is a sequenced such that, for a large percentage of unique tagged parent polynucleotides in the set of tagged parent polynucleotides, there is a sequence read that is produced for at least one amplified progeny polynucleotide in a family produced from a unique tagged parent polynucleotide. In a second strategy, the amplified progeny polynucleotide set is sampled for sequencing at a level to produce sequence reads from multiple progeny members of a family derived from a unique parent polynucleotide. Generation of sequence reads from multiple progeny members of a family allows collapsing of sequences into consensus parent sequences.

So, for example, sampling a number of amplified progeny polynucleotides from the set of amplified progeny polynucleotides that is equal to the number of unique tagged parent polynucleotides in the set of tagged parent polynucleotides (particularly when the number is at least 10,000) will produce, statistically, a sequence read for at least one of progeny of about 68% of the tagged parent polynucleotides in the set, and about 40% of the unique tagged parent polynucleotides in the original set will be represented by at least two progeny sequence reads. In certain embodiments the amplified progeny polynucleotide set is sampled sufficiently so as to produce an average of five to ten sequence reads for each family. Sampling from the amplified progeny set of 10-times as many molecules as the number of unique tagged parent polynucleotides will produce, statistically, sequence information about 99.995% of the families, of which 99.95% of the total families will be covered by a plurality of sequence reads. A consensus sequence can be built from the progeny polynucleotides in each family so as to dramatically reduce the error rate from the nominal per-base sequencing error rate to a rate possibly many orders of magnitude lower. For example, if the sequencer has a random per-base error rate of 1% and the chosen family has 10 reads, a consensus sequence built from these 10 reads would possess an error rate of below 0.0001%. Accordingly, the sampling size of the amplified progeny to be sequenced can be chosen so as to ensure a sequence having a frequency in the sample that is no greater than the nominal per-base sequencing error rate to a rate of the sequencing platform used, has at least 99% chance being represented by at least one read.

In another embodiment the set of amplified progeny polynucleotides is sampled to a level to produce a high probability e.g., at least 90%, that a sequence represented in the set of tagged parent polynucleotides at a frequency that is about the same as the per base sequencing error rate of the sequencing platform used is covered by at least one sequence read and preferably a plurality of sequence reads. So, for example, if the sequencing platform has a per base error rate of 0.2% in a sequence or set of sequences is represented in the set of tagged parent polynucleotides at a frequency of about 0.2%, then the number of polynucleotides in the amplified progeny pool that are sequenced can be about X times the number of unique molecules in the set of tagged parent polynucleotides.

These methods can be combined with any of the noise reduction methods described. Including, for example, qualifying sequence reads for inclusion in the pool of sequences used to generate consensus sequences.

This information can now be used for both qualitative and quantitative analysis. For example, for quantitative analysis, a measure, e.g., a count, of the amount of tagged parent molecules mapping to a reference sequence is determined. This measure can be compared with a measure of tagged parent molecules mapping to a different genomic region. That is, the amount of tagged parent molecules mapping to a first location or mappable position in a reference sequence, such as the human genome, can be compared with a measure of tagged parent molecules mapping to a second location or mappable position in a reference sequence. This comparison can reveal, for example, the relative amounts of parent molecules mapping to each region. This, in turn, provides an indication of copy number variation for molecules mapping to a particular region. For example, if the measure of polynucleotides mapping to a first reference sequence is greater than the measure of polynucleotides mapping to a second reference sequence, this may indicate that the parent population, and by extension the original sample, included polynucleotides from cells exhibiting aneuploidy. The measures can be normalized against a control sample to eliminate various biases. Quantitative measures can include, for example, number, count, frequency (whether relative, inferred or absolute).

A reference genome can include the genome of any species of interest. Human genome sequences useful as references can include the hg19 assembly or any previous or available hg assembly. Such sequences can be interrogated using the genome browser available at genome.ucsc.edu/index.html. Other species genomes include, for example PanTro2 (chimp) and mm9 (mouse).

For qualitative analysis, sequences from a set of tagged polynucleotides mapping to a reference sequence can be analyzed for variant sequences and their frequency in the population of tagged parent polynucleotides can be measured.

II. Sample Preparation

A. Polynucleotide Isolation and Extraction

The systems and methods of this disclosure may have a wide variety of uses in the manipulation, preparation, identification and/or quantification of cell free polynucleotides. Examples of polynucleotides include but are not limited to: DNA, RNA, amplicons, cDNA, dsDNA, ssDNA, plasmid DNA, cosmid DNA, high Molecular Weight (MW) DNA, chromosomal DNA, genomic DNA, viral DNA, bacterial DNA, mtDNA (mitochondrial DNA), mRNA, rRNA, tRNA, nRNA, siRNA, snRNA, snoRNA, scaRNA, microRNA, dsRNA, ribozyme, riboswitch and viral RNA (e.g., retroviral RNA).

Cell free polynucleotides may be derived from a variety of sources including human, mammal, non-human mammal, ape, monkey, chimpanzee, reptilian, amphibian, or avian, sources. Further, samples may be extracted from variety of animal fluids containing cell free sequences, including but not limited to blood, serum, plasma, vitreous, sputum, urine, tears, perspiration, saliva, semen, mucosal excretions, mucus, spinal fluid, amniotic fluid, lymph fluid and the like. Cell free polynucleotides may be fetal in origin (via fluid taken from a pregnant subject), or may be derived from tissue of the subject itself.

Isolation and extraction of cell free polynucleotides may be performed through collection of bodily fluids using a variety of techniques. In some cases, collection may comprise aspiration of a bodily fluid from a subject using a syringe. In other cases collection may comprise pipetting or direct collection of fluid into a collecting vessel.

After collection of bodily fluid, cell free polynucleotides may be isolated and extracted using a variety of techniques known in the art. In some cases, cell free DNA may be isolated, extracted and prepared using commercially available kits such as the Qiagen Qiamp® Circulating Nucleic Acid Kit protocol. In other examples, Qiagen Qubit™ dsDNA HS Assay kit protocol, Agilent™ DNA 1000 kit, or TruSeq™ Sequencing Library Preparation; Low-Throughput (LT) protocol may be used.

Generally, cell free polynucleotides are extracted and isolated by from bodily fluids through a partitioning step in which cell free DNAs, as found in solution, are separated from cells and other non soluble components of the bodily fluid. Partitioning may include, but is not limited to, techniques such as centrifugation or filtration. In other cases, cells are not partitioned from cell free DNA first, but rather lysed. In this example, the genomic DNA of intact cells is partitioned through selective precipitation. Cell free polynucleotides, including DNA, may remain soluble and may be separated from insoluble genomic DNA and extracted. Generally, after addition of buffers and other wash steps specific to different kits, DNA may be precipitated using isopropanol precipitation. Further clean up steps may be used such as silica based columns to remove contaminants or salts. General steps may be optimized for specific applications. Non specific bulk carrier polynucleotides, for example, may be added throughout the reaction to optimize certain aspects of the procedure such as yield.

Isolation and purification of cell free DNA may be accomplished using any means, including, but not limited to, the use of commercial kits and protocols provided by companies such as Sigma Aldrich, Life Technologies, Promega, Affymetrix, IBI or the like. Kits and protocols may also be non-commercially available.

After isolation, in some cases, the cell free polynucleotides are pre-mixed with one or more additional materials, such as one or more reagents (e.g., ligase, protease, polymerase) prior to sequencing.

One method of increasing conversion efficiency involves using a ligase engineered for optimal reactivity on single-stranded DNA, such as a ThermoPhage ssDNA ligase derivative. Such ligases bypass traditional steps in library preparation of end-repair and A-tailing that can have poor efficiencies and/or accumulated losses due to intermediate cleanup steps, and allows for twice the probability that either the sense or anti-sense starting polynucleotide will be converted into an appropriately tagged polynucleotide. It also converts double-stranded polynucleotides that may possess overhangs that may not be sufficiently blunt-ended by the typical end-repair reaction. Optimal reactions conditions for this ssDNA reaction are: 1× reaction buffer (50 mM MOPS (pH 7.5), 1 mM DTT, 5 mM MgCl2, 10 mM KCl). With 50 mM ATP, 25 mg/ml BSA, 2.5 mM MnCl2, 200 pmol 85 nt ssDNA oligomer and 5 U ssDNA ligase incubated at 65° C. for 1 hour. Subsequent amplification using PCR can further convert the tagged single-stranded library to a double-stranded library and yield an overall conversion efficiency of well above 20%. Other methods of increasing conversion rate, e.g., to above 10%, include, for example, any of the following, alone or in combination: Annealing-optimized molecular-inversion probes, blunt-end ligation with a well-controlled polynucleotide size range, sticky-end ligation or an upfront multiplex amplification step with or without the use of fusion primers.

B. Molecular Bar Coding of Cell Free Polynucleotides

The systems and methods of this disclosure may also enable the cell free polynucleotides to be tagged or tracked in order to permit subsequent identification and origin of the particular polynucleotide. This feature is in contrast with other methods that use pooled or multiplex reactions and that only provide measurements or analyses as an average of multiple samples. Here, the assignment of an identifier to individual or subgroups of polynucleotides may allow for a unique identity to be assigned to individual sequences or fragments of sequences. This may allow acquisition of data from individual samples and is not limited to averages of samples.

In some examples, nucleic acids or other molecules derived from a single strand may share a common tag or identifier and therefore may be later identified as being derived from that strand. Similarly, all of the fragments from a single strand of nucleic acid may be tagged with the same identifier or tag, thereby permitting subsequent identification of fragments from the parent strand. In other cases, gene expression products (e.g., mRNA) may be tagged in order to quantify expression, by which the barcode, or the barcode in combination with sequence to which it is attached can be counted. In still other cases, the systems and methods can be used as a PCR amplification control. In such cases, multiple amplification products from a PCR reaction can be tagged with the same tag or identifier. If the products are later sequenced and demonstrate sequence differences, differences among products with the same identifier can then be attributed to PCR error.

Additionally, individual sequences may be identified based upon characteristics of sequence data for the read themselves. For example, the detection of unique sequence data at the beginning (start) and end (stop) portions of individual sequencing reads may be used, alone or in combination, with the length, or number of base pairs of each sequence read unique sequence to assign unique identities to individual molecules. Fragments from a single strand of nucleic acid, having been assigned a unique identity, may thereby permit subsequent identification of fragments from the parent strand. This can be used in conjunction with bottlenecking the initial starting genetic material to limit diversity.

Further, using unique sequence data at the beginning (start) and end (stop) portions of individual sequencing reads and sequencing read length may be used, alone or combination, with the use of barcodes. In some cases, the barcodes may be unique as described herein. In other cases, the barcodes themselves may not be unique. In this case, the use of non unique barcodes, in combination with sequence data at the beginning (start) and end (stop) portions of individual sequencing reads and sequencing read length may allow for the assignment of a unique identity to individual sequences. Similarly, fragments from a single strand of nucleic acid having been assigned a unique identity, may thereby permit subsequent identification of fragments from the parent strand.

Generally, the methods and systems provided herein are useful for preparation of cell free polynucleotide sequences to a down-stream application sequencing reaction. Often, a sequencing method is classic Sanger sequencing. Sequencing methods may include, but are not limited to: high-throughput sequencing, pyrosequencing, sequencing-by-synthesis, single-molecule sequencing, nanopore sequencing, semiconductor sequencing, sequencing-by-ligation, sequencing-by-hybridization, RNA-Seq (Illumina), Digital Gene Expression (Helicos), Next generation sequencing, Single Molecule Sequencing by Synthesis (SMSS)(Helicos), massively-parallel sequencing, Clonal Single Molecule Array (Solexa), shotgun sequencing, Maxim-Gilbert sequencing, primer walking, and any other sequencing methods known in the art.

C. Assignment of Barcodes to Cell Free Polynucleotide Sequences

The systems and methods disclosed herein may be used in applications that involve the assignment of unique or non-unique identifiers, or molecular barcodes, to cell free polynucleotides. Often, the identifier is a bar-code oligonucleotide that is used to tag the polynucleotide; but, in some cases, different unique identifiers are used. For example, in some cases, the unique identifier is a hybridization probe. In other cases, the unique identifier is a dye, in which case the attachment may comprise intercalation of the dye into the analyte molecule (such as intercalation into DNA or RNA) or binding to a probe labeled with the dye. In still other cases, the unique identifier may be a nucleic acid oligonucleotide, in which case the attachment to the polynucleotide sequences may comprise a ligation reaction between the oligonucleotide and the sequences or incorporation through PCR. In other cases, the reaction may comprise addition of a metal isotope, either directly to the analyte or by a probe labeled with the isotope. Generally, assignment of unique or non-unique identifiers, or molecular barcodes in reactions of this disclosure may follow methods and systems described by, for example, US patent applications 20010053519, 20030152490, 20110160078 and U.S. Pat. No. 6,582,908.

Often, the method comprises attaching oligonucleotide barcodes to nucleic acid analytes through an enzymatic reaction including but not limited to a ligation reaction. For example, the ligase enzyme may covalently attach a DNA barcode to fragmented DNA (e.g., high molecular-weight DNA). Following the attachment of the barcodes, the molecules may be subjected to a sequencing reaction.

However, other reactions may be used as well. For example, oligonucleotide primers containing barcode sequences may be used in amplification reactions (e.g., PCR, qPCR, reverse-transcriptase PCR, digital PCR, etc.) of the DNA template analytes, thereby producing tagged analytes. After assignment of barcodes to individual cell free polynucleotide sequences, the pool of molecules may be sequenced.

In some cases, PCR may be used for global amplification of cell free polynucleotide sequences. This may comprise using adapter sequences that may be first ligated to different molecules followed by PCR amplification using universal primers. PCR for sequencing may be performed using any means, including but not limited to use of commercial kits provided by Nugen (WGA kit), Life Technologies, Affymetrix, Promega, Qiagen and the like. In other cases, only certain target molecules within a population of cell free polynucleotide molecules may be amplified. Specific primers, may in conjunction with adapter ligation, may be used to selectively amplify certain targets for downstream sequencing.

The unique identifiers (e.g., oligonucleotide bar-codes, antibodies, probes, etc.) may be introduced to cell free polynucleotide sequences randomly or non-randomly. In some cases, they are introduced at an expected ratio of unique identifiers to microwells. For example, the unique identifiers may be loaded so that more than about 1, 2, 3, 4, 5, 6, 7, 8, 9, 10, 20, 50, 100, 500, 1000, 5000, 10000, 50,000, 100,000, 500,000, 1,000,000, 10,000,000, 50,000,000 or 1,000,000,000 unique identifiers are loaded per genome sample. In some cases, the unique identifiers may be loaded so that less than about 2, 3, 4, 5, 6, 7, 8, 9, 10, 20, 50, 100, 500, 1000, 5000, 10000, 50,000, 100,000, 500,000, 1,000, 000, 10,000,000, 50,000,000 or 1,000,000,000 unique identifiers are loaded per genome sample. In some cases, the average number of unique identifiers loaded per sample genome is less than, or greater than, about 1, 2, 3, 4, 5, 6, 7, 8, 9, 10, 20, 50, 100, 500, 1000, 5000, 10000, 50,000, 100,000, 500,000, 1,000,000, 10,000,000, 50,000,000 or 1,000,000,000 unique identifiers per genome sample.

In some cases, the unique identifiers may be a variety of lengths such that each barcode is at least about 1, 2, 3, 4, 5, 6, 7, 8, 9, 10, 20, 50, 100, 500, 1000 base pairs. In other cases, the barcodes may comprise less than 1, 2, 3, 4, 5, 6, 7, 8, 9, 10, 20, 50, 100, 500, 1000 base pairs.

In some cases, unique identifiers may be predetermined or random or semi-random sequence oligonucleotides. In other cases, a plurality of barcodes may be used such that barcodes are not necessarily unique to one another in the plurality. In this example, barcodes may be ligated to individual molecules such that the combination of the bar code and the sequence it may be ligated to creates a unique sequence that may be individually tracked. As described herein, detection of non unique barcodes in combination with sequence data of beginning (start) and end (stop) portions of sequence reads may allow assignment of a unique identity to a particular molecule. The length, or number of base pairs, of an individual sequence read may also be used to assign a unique identity to such a molecule. As described herein, fragments from a single strand of nucleic acid having been assigned a unique identity, may thereby permit subsequent identification of fragments from the parent strand. In this way the polynucleotides in the sample can be uniquely or substantially uniquely tagged.

The unique identifiers may be used to tag a wide range of analytes, including but not limited to RNA or DNA molecules. For example, unique identifiers (e.g., barcode oligonucleotides) may be attached to whole strands of nucleic acids or to fragments of nucleic acids (e.g., fragmented genomic DNA, fragmented RNA). The unique identifiers (e.g., oligonucleotides) may also bind to gene expression products, genomic DNA, mitochondrial DNA, RNA, mRNA, and the like.

In many applications, it may be important to determine whether individual cell free polynucleotide sequences each receive a different unique identifier (e.g., oligonucleotide barcode). If the population of unique identifiers introduced into the systems and methods is not significantly diverse, different analytes may possibly be tagged with identical identifiers. The systems and methods disclosed herein may enable detection of cell free polynucleotide sequences tagged with the same identifier. In some cases, a reference sequences may be included with the population of cell free polynucleotide sequences to be analyzed. The reference sequence may be, for example, a nucleic acid with a known sequence and a known quantity. If the unique identifiers are oligonucleotide barcodes and the analytes are nucleic acids, the tagged analytes may subsequently be sequenced and quantified. These methods may indicate if one or more fragments and/or analytes may have been assigned an identical barcode.

A method disclosed herein may comprise utilizing reagents necessary for the assignment of barcodes to the analytes. In the case of ligation reactions, reagents including, but not limited to, ligase enzyme, buffer, adapter oligonucleotides, a plurality of unique identifier DNA barcodes and the like may be loaded into the systems and methods. In the case of enrichment, reagents including but not limited to a plurality of PCR primers, oligonucleotides containing unique identifying sequence, or barcode sequence, DNA polymerase, DNTPs, and buffer and the like may be used in preparation for sequencing.

Generally, the method and system of this disclosure may utilize the methods of U.S. Pat. No. 7,537,897 in using molecular barcodes to count molecules or analytes.

In a sample comprising fragmented genomic DNA, e.g., cell-free DNA (cfDNA), from a plurality of genomes, there is some likelihood that more than one polynucleotide from different genomes will have the same start and stop positions ("duplicates" or "cognates"). The probable number of duplicates beginning at any position is a function of the number of haploid genome equivalents in a sample and the distribution of fragment sizes. For example, cfDNA has a peak of fragments at about 160 nucleotides, and most of the fragments in this peak range from about 140 nucleotides to 180 nucleotides. Accordingly, cfDNA from a genome of about 3 billion bases (e.g., the human genome) may be comprised of almost 20 million ($2 \times 10^7$) polynucleotide fragments. A sample of about 30 ng DNA can contain about 10,000 haploid human genome equivalents. (Similarly, a sample of about 100 ng of DNA can contain about 30,000 haploid human genome equivalents.) A sample containing about 10,000 ($10^4$) haploid genome equivalents of such DNA can have about 200 billion ($2 \times 10^{11}$) individual polynucleotide molecules. It has been empirically determined that in a sample of about 10,000 haploid genome equivalents of human DNA, there are about 3 duplicate polynucleotides beginning at any given position. Thus, such a collection can contain a diversity of about $6 \times 10^{10}$-$8 \times 10^{10}$ (about 60 billion-80 billion e.g., about 70 billion ($7 \times 10^{10}$)) differently sequenced polynucleotide molecules.

The probability of correctly identifying molecules is dependent on initial number of genome equivalents, the length distribution of sequenced molecules, sequence uniformity and number of tags. When the tag count is equal to one, that is, equivalent to having no unique tags or not tagging. The table below lists the probability of correctly identifying a molecule as unique assuming a typical cell-free size distribution as above.

| Tag Count | Tag % Correctly uniquely identified |
|---|---|
| 1000 human haploid genome equivalents | |
| 1 | 96.9643 |
| 4 | 99.2290 |
| 9 | 99.6539 |
| 16 | 99.8064 |
| 25 | 99.8741 |
| 100 | 99.9685 |
| 3000 human haploid genome equivalents | |
| 1 | 91.7233 |
| 4 | 97.8178 |
| 9 | 99.0198 |
| 16 | 99.4424 |
| 25 | 99.6412 |
| 100 | 99.9107 |

In this case, upon sequencing the genomic DNA, it may not be possible to determine which sequence reads are derived from which parent molecules. This problem can be diminished by tagging parent molecules with a sufficient number of unique identifiers (e.g., the tag count) such that there is a likelihood that two duplicate molecules, i.e., molecules having the same start and stop positions, bear different unique identifiers so that sequence reads are traceable back to particular parent molecules. One approach to this problem is to uniquely tag every, or nearly every, different parent molecule in the sample. However, depending on the number of haploid gene equivalents and distribution of fragment sizes in the sample, this may require billions of different unique identifiers.

This method can be cumbersome and expensive. This invention provides methods and compositions in which a population of polynucleotides in a sample of fragmented genomic DNA is tagged with n different unique identifiers, wherein n is at least 2 and no more than 100,000*z, wherein z is a measure of central tendency (e.g., mean, median, mode) of an expected number of duplicate molecules having the same start and stop positions. In certain embodiments, n is at least any of 2*z, 3*z, 4*z, 5*z, 6*z, 7*z, 8*z, 9*z, 10*z, 11*z, 12*z, 13*z, 14*z, 15*z, 16*z, 17*z, 18*z, 19*z, or 20*z (e.g., lower limit). In other embodiments, n is no greater than 100,000*z, 10,000*z, 1000*z or 100*z (e.g., upper limit). Thus, n can range between any combination of these lower and upper limits. In certain embodiments, n is between 5*z and 15*z, between 8*z and 12*z, or about 10*z. For example, a haploid human genome equivalent has about 3 picograms of DNA. A sample of about 1 microgram of DNA contains about 300,000 haploid human genome equivalents. The number n can be between 15 and 45, between 24 and 36 or about 30. Improvements in sequencing can be achieved as long as at least some of the duplicate or cognate polynucleotides bear unique identifiers, that is, bear different tags. However, in certain embodiments, the number of tags used is selected so that there is at least a 95% chance that all duplicate molecules starting at any one position bear unique identifiers. For example, a sample comprising about 10,000 haploid human genome equivalents of cfDNA can be tagged with about 36 unique identifiers. The unique identifiers can comprise six unique DNA barcodes. Attached to both ends of a polynucleotide, 36 possible unique identifiers are produced. Samples tagged in such a way can be those with a range of about 10 ng to any of about 100 ng, about 1 gig, about 10 μg of fragmented polynucleotides, e.g., genomic DNA, e.g. cfDNA.

Accordingly, this invention also provides compositions of tagged polynucleotides. The polynucleotides can comprise fragmented DNA, e.g. cfDNA. A set of polynucleotides in the composition that map to a mappable base position in a genome can be non-uniquely tagged, that is, the number of different identifiers can be at least at least 2 and fewer than the number of polynucleotides that map to the mappable base position. A composition of between about 10 ng to about 10 μg (e.g., any of about 10 ng-1 gig, about 10 ng-100 ng, about 100 ng-10 gig, about 100 ng-1 gig, about 1 μg-10 μg) can bear between any of 2, 5, 10, 50 or 100 to any of 100, 1000, 10,000 or 100,000 different identifiers. For example, between 5 and 100 different identifiers can be used to tag the polynucleotides in such a composition.

III. Nucleic Acid Sequencing Platforms

After extraction and isolation of cell free polynucleotides from bodily fluids, cell free sequences may be sequenced. Often, a sequencing method is classic Sanger sequencing. Sequencing methods may include, but are not limited to: high-throughput sequencing, pyrosequencing, sequencing-by-synthesis, single-molecule sequencing, nanopore sequencing, semiconductor sequencing, sequencing-by-ligation, sequencing-by-hybridization, RNA-Seq (Illumina), Digital Gene Expression (Helicos), Next generation sequencing, Single Molecule Sequencing by Synthesis (SMSS)(Helicos), massively-parallel sequencing, Clonal Single Molecule Array (Solexa), shotgun sequencing, Maxim-Gilbert sequencing, primer walking, sequencing using PacBio, SOLiD, Ion Torrent, or Nanopore platforms and any other sequencing methods known in the art.

In some cases, sequencing reactions various types, as described herein, may comprise a variety of sample processing units. Sample processing units may include but are not limited to multiple lanes, multiple channels, multiple wells, or other mean of processing multiple sample sets substantially simultaneously. Additionally, the sample processing unit may include multiple sample chambers to enable processing of multiple runs simultaneously.

In some examples, simultaneous sequencing reactions may be performed using multiplex sequencing. In some cases, cell free polynucleotides may be sequenced with at least 1000, 2000, 3000, 4000, 5000, 6000, 7000, 8000, 9000, 10000, 50000, 100,000 sequencing reactions. In other cases cell free poly nucleotides may be sequenced with less than 1000, 2000, 3000, 4000, 5000, 6000, 7000, 8000, 9000, 10000, 50000, 100,000 sequencing reactions. Sequencing reactions may be performed sequentially or simultaneously. Subsequent data analysis may be performed on all or part of the sequencing reactions. In some cases, data analysis may be performed on at least 1000, 2000, 3000, 4000, 5000, 6000, 7000, 8000, 9000, 10000, 50000, 100,000 sequencing reactions. In other cases data analysis may be performed on less than 1000, 2000, 3000, 4000, 5000, 6000, 7000, 8000, 9000, 10000, 50000, 100,000 sequencing reactions.

In other examples, the number of sequence reactions may provide coverage for different amounts of the genome. In some cases, sequence coverage of the genome may be at least 5%, 10%, 15%, 20%, 25%, 30%, 40%, 50%, 60%, 70%, 80%, 90%, 95%, 99%, 99.9% or 100%. In other cases, sequence coverage of the genome may be less than 5%, 10%, 15%, 20%, 25%, 30%, 40%, 50%, 60%, 70%, 80%, 90%, 95%, 99%, 99.9% or 100%.

In some examples, sequencing can be performed on cell free polynucleotides that may comprise a variety of different types of nucleic acids. Nucleic acids may be polynucleotides or oligonucleotides. Nucleic acids included, but are not limited to DNA or RNA, single stranded or double stranded or a RNA/cDNA pair.

IV. Polynucleotide Analysis Strategy

Figure 8:
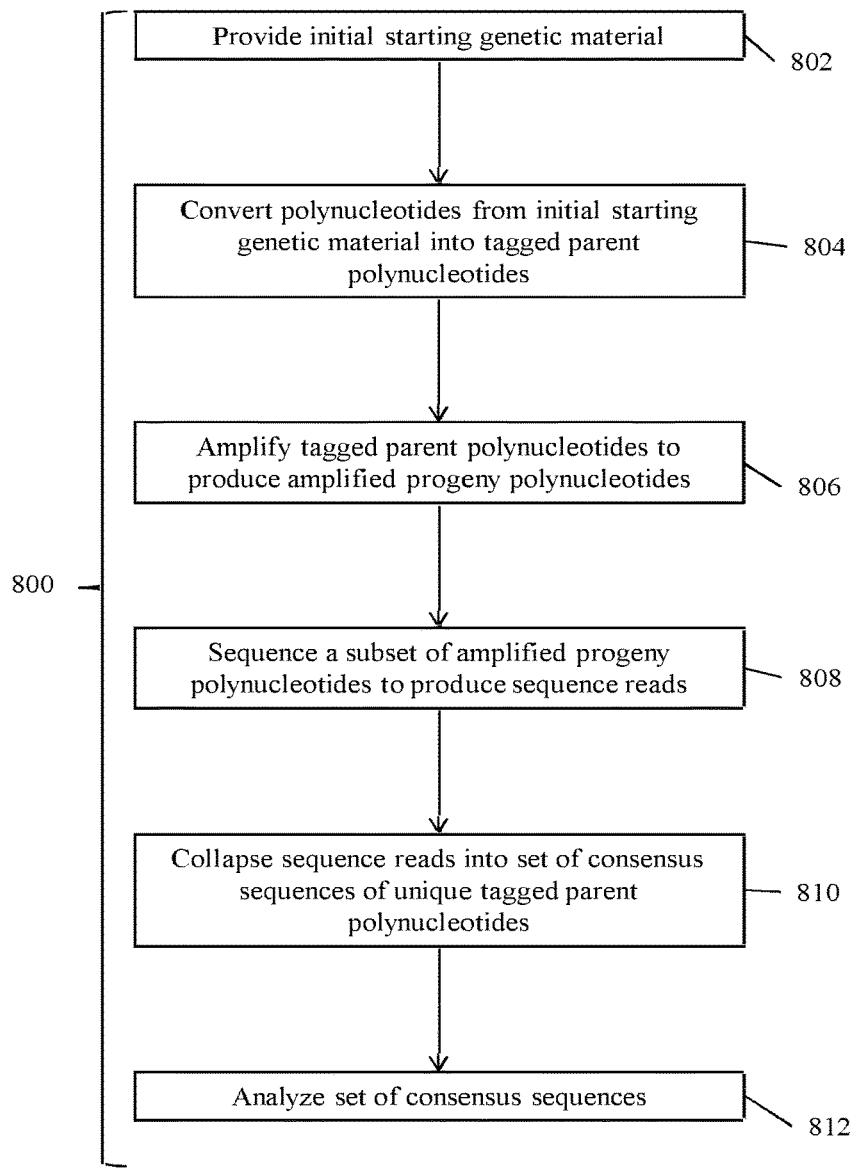
FIG. 8 is a flow chart representation of a method of analyzing genetic material.

FIG. 8. is a diagram, 800, showing a strategy for analyzing polynucleotides in a sample of initial genetic material. In step 802, a sample containing initial genetic material is provided. The sample can include target nucleic acid in low abundance. For example, nucleic acid from a normal or wild-type genome (e.g., a germline genome) can predominate in a sample that also includes no more than 20%, no more than 10%, no more than 5%, no more than 1%, no more than 0.5% or no more than 0.1% nucleic acid from at least one other genome containing genetic variation, e.g., a cancer genome or a fetal genome, or a genome from another species. The sample can include, for example, cell free nucleic acid or cells comprising nucleic acid. The initial genetic material can constitute no more than 100 ng nucleic acid. This can contribute to proper oversampling of the original polynucleotides by the sequencing or genetic analysis process. Alternatively, the sample can be artificially capped or bottlenecked to reduce the amount of nucleic acid to no more than 100 ng or selectively enriched to analyze only sequences of interest. The sample can be modified to selectively produce sequence reads of molecules mapping to each of one or more selected locations in a reference sequence. A sample of 100 ng of nucleic acid can contain about 30,000 human haploid genome equivalents, that is, molecules that, together, provide 30,000-fold coverage of a human genome.

In step 804 the initial genetic material is converted into a set of tagged parent polynucleotides. Tagging can include attaching sequenced tags to molecules in the initial genetic material. Sequenced tags can be selected so that all unique polynucleotides mapping to the same location in a reference sequence had a unique identifying tag. Conversion can be performed at high efficiency, for example at least 50%.

In step 806, the set of tagged parent polynucleotides is amplified to produce a set of amplified progeny polynucleotides. Amplification may be, for example, 1,000-fold.

In step 808, the set of amplified progeny polynucleotides are sampled for sequencing. The sampling rate is chosen so that the sequence reads produced both (1) cover a target number of unique molecules in the set of tagged parent polynucleotides and (2) cover unique molecules in the set of tagged parent polynucleotides at a target coverage fold (e.g., 5- to 10-fold coverage of parent polynucleotides.

In step 810, the set of sequence reads is collapsed to produce a set of consensus sequences corresponding to unique tagged parent polynucleotides. Sequence reads can be qualified for inclusion in the analysis. For example, sequence reads that fail to meet a quality control scores can be removed from the pool. Sequence reads can be sorted into families representing reads of progeny molecules derived from a particular unique parent molecule. For example, a family of amplified progeny polynucleotides can constitute those amplified molecules derived from a single parent polynucleotide. By comparing sequences of progeny in a family, a consensus sequence of the original parent polynucleotide can be deduced. This produces a set of consensus sequences representing unique parent polynucleotides in the tagged pool.

In step 812, the set of consensus sequences is analyzed using any of the analytical methods described herein. For example, consensus sequences mapping to a particular reference sequence location can be analyzed to detect instances of genetic variation. Consensus sequences mapping to particular reference sequences can be measured and normalized against control samples. Measures of molecules mapping to reference sequences can be compared across a genome to identify areas in the genome in which copy number varies, or heterozygosity is lost.

Figure 9:
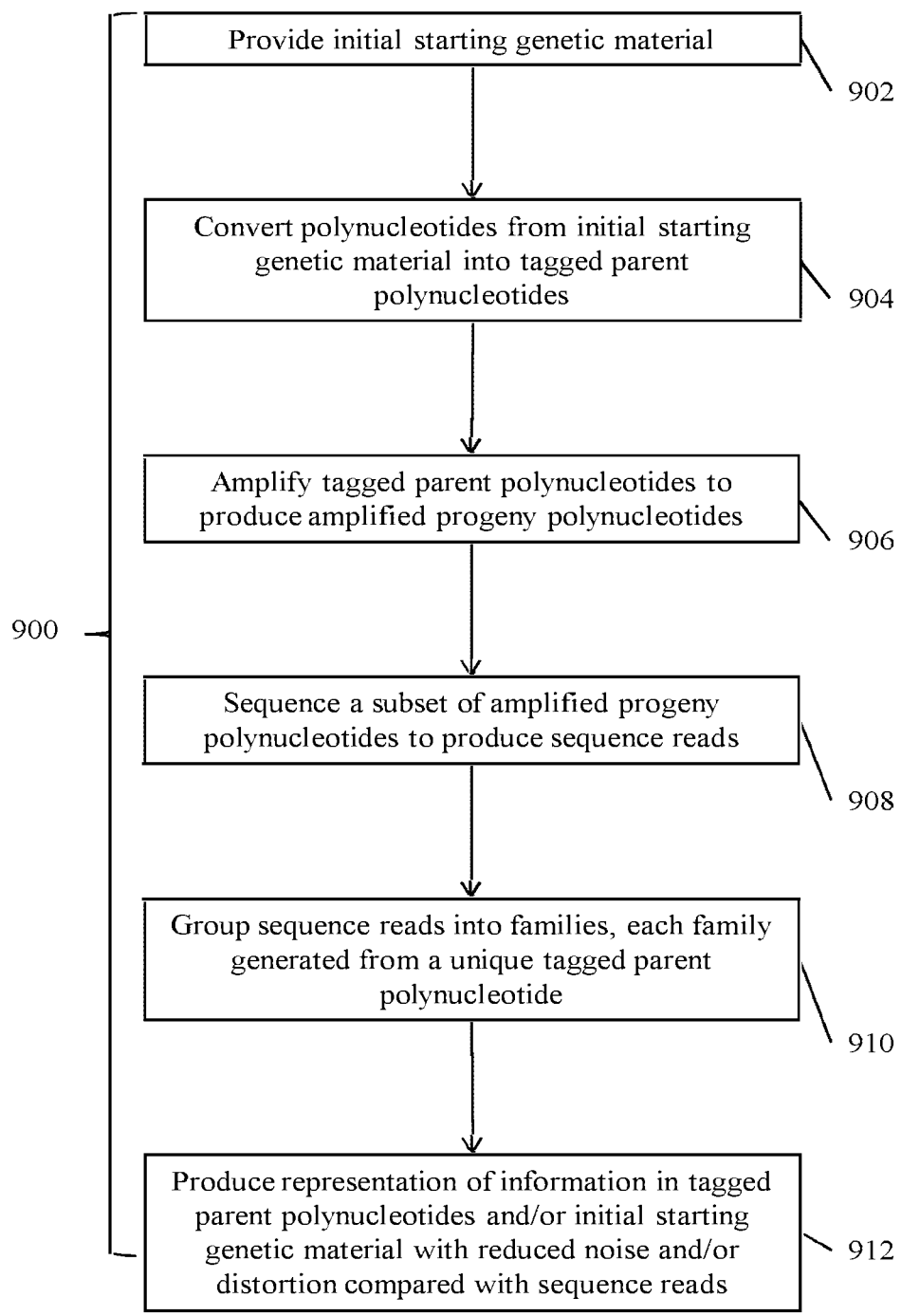
FIG. 9 is a flow chart representation of a method of decoding information in a set of sequence reads to produce, with reduced noise and/or distortion, a representation of information in a set of tagged parent polynucleotides.

FIG. 9 is a diagram presenting a more generic method of extracting information from a signal represented by a collection of sequence reads. In this method, after sequencing amplified progeny polynucleotides, the sequence reads are grouped into families of molecules amplified from a molecule of unique identity (910). This grouping can be a jumping off point for methods of interpreting the information in the sequence to determine the contents of the tagged parent polynucleotides with higher fidelity, e.g., less noise and/or distortion.

Analysis of the collection of sequence reads allows one to make inferences about the parent polynucleotide population from which the sequence reads were generated. Such inferences may be useful because sequencing typically involves reading only a partial subset of the global total amplified polynucleotides. Therefore, one cannot be certain that every parent polynucleotide will be represented by at least one sequence read in the collection of sequence reads.

One such inference is the number of unique parent polynucleotides in the original pool. Such an inference can be made based on the number of unique families into which the sequence reads can be grouped and the number of sequence reads in each family. In this case, a family refers to a collection of sequence reads traceable back to an original parent polynucleotide. The inference can be made using well-known statistical methods. For example, if grouping produces many families, each represented by one or a few progeny, then one can infer that the original population included more unique parent polynucleotides that were not sequenced. On the other hand, if grouping produces only a few families, each family represented by many progeny, then one can infer that most of the unique polynucleotides in the parent population are represented by at least one sequence read group into that family.

Another such inference is the frequency of a base or sequence of bases at a particular locus in an original pool of polynucleotides. Such an inference can be made based on the number of unique families into which the sequence reads can be grouped and the number of sequence reads in each family. Analyzing the base calls at a locus in a family of sequence reads, a confidence score is assigned to each particular base call or sequence. Then, taking into consideration the confidence score for each base call in a plurality of the families, the frequency of each base or sequence at the locus is determined.

V. Copy Number Variation Detection

A. Copy Number Variation Detection Using Single Sample

FIG. 1. is a diagram, 100, showing a strategy for detection of copy number variation in a single subject. As shown herein, copy number variation detection methods can be implemented as follows. After extraction and isolation of cell free polynucleotides in step 102, a single unique sample can be sequenced by a nucleic acid sequencing platform known in the art in step 104. This step generates a plurality of genomic fragment sequence reads. In some cases, these sequences reads may contain barcode information. In other examples, barcodes are not utilized. After sequencing, reads are assigned a quality score. A quality score may be a representation of reads that indicates whether those reads may be useful in subsequent analysis based on a threshold. In some cases, some reads are not of sufficient quality or length to perform the subsequent mapping step. Sequencing reads with a quality score at least 90%, 95%, 99%, 99.9%, 99.99% or 99.999% may be filtered out of the data. In other cases, sequencing reads assigned a quality scored less than 90%, 95%, 99%, 99.9%, 99.99% or 99.999% may be filtered out of the data set. In step 106, the genomic fragment reads that meet a specified quality score threshold are mapped to a reference genome, or a template sequence that is known not to contain copy number variations. After mapping alignment, sequence reads are assigned a mapping score. A mapping score may be a representation or reads mapped back to the reference sequence indicating whether each position is or is not uniquely mappable. In instances, reads may be sequences unrelated to copy number variation analysis. For example, some sequence reads may originate from contaminant polynucleotides. Sequencing reads with a mapping score at least 90%, 95%, 99%, 99.9%, 99.99% or 99.999% may be filtered out of the data set. In other cases, sequencing reads assigned a mapping scored less than 90%, 95%, 99%, 99.9%, 99.99% or 99.999% may be filtered out of the data set.

After data filtering and mapping, the plurality of sequence reads generates a chromosomal region of coverage. In step 108 these chromosomal regions may be divided into variable length windows or bins. A window or bin may be at least 5 kb, 10, kb, 25 kb, 30 kb, 35, kb, 40 kb, 50 kb, 60 kb, 75 kb, 100 kb, 150 kb, 200 kb, 500 kb, or 1000 kb. A window or bin may also have bases up to 5 kb, 10, kb, 25 kb, 30 kb, 35, kb, 40 kb, 50 kb, 60 kb, 75 kb, 100 kb, 150 kb, 200 kb, 500 kb, or 1000 kb. A window or bin may also be about 5 kb, 10, kb, 25 kb, 30 kb, 35, kb, 40 kb, 50 kb, 60 kb, 75 kb, 100 kb, 150 kb, 200 kb, 500 kb, or 1000 kb.

For coverage normalization in step 110, each window or bin is selected to contain about the same number of mappable bases. In some cases, each window or bin in a chromosomal region may contain the exact number of mappable bases. In other cases, each window or bin may contain a different number of mappable bases. Additionally, each window or bin may be non-overlapping with an adjacent window or bin. In other cases, a window or bin may overlap with another adjacent window or bin. In some cases a window or bin may overlap by at least 1 bp, 2, bp, 3 bp, 4 bp, 5, bp, 10 bp, 20 bp, 25 bp, 50 bp, 100 bp, 200 bp, 250 bp, 500 bp, or 1000 bp. In other cases, a window or bin may overlap by up to 1 bp, 2, bp, 3 bp, 4 bp, 5, bp, 10 bp, 20 bp, 25 bp, 50 bp, 100 bp, 200 bp, 250 bp, 500 bp, or 1000 bp. In some cases a window or bin may overlap by about 1 bp, 2, bp, 3 bp, 4 bp, 5, bp, 10 bp, 20 bp, 25 bp, 50 bp, 100 bp, 200 bp, 250 bp, 500 bp, or 1000 bp.

In some cases, each of the window regions may be sized so they contain about the same number of uniquely mappable bases. The mappability of each base that comprise a window region is determined and used to generate a mappability file which contains a representation of reads from the references that are mapped back to the reference for each file. The mappability file contains one row per every position, indicating whether each position is or is not uniquely mappable.

Additionally, predefined windows, known throughout the genome to be hard to sequence, or contain a substantially high GC bias, may be filtered from the data set. For example, regions known to fall near the centromere of chromosomes (i.e., centromeric DNA) are known to contain highly repetitive sequences that may produce false positive results. These regions may be filtered out. Other regions of the genome, such as regions that contain an unusually high concentration of other highly repetitive sequences such as microsatellite DNA, may be filtered from the data set.

The number of windows analyzed may also vary. In some cases, at least 10, 20, 30, 40, 50, 100, 200, 500, 1000, 2000, 5,000, 10,000, 20,000, 50,000 or 100,000 windows are analyzed. In other cases, the number of widows analyzed is up to 10, 20, 30, 40, 50, 100, 200, 500, 1000, 2000, 5,000, 10,000, 20,000, 50,000 or 100,000 windows are analyzed.

For an exemplary genome derived from cell free polynucleotide sequences, the next step comprises determining read coverage for each window region. This may be performed using either reads with barcodes, or without barcodes. In cases without barcodes, the previous mapping steps will provide coverage of different base positions. Sequence reads that have sufficient mapping and quality scores and fall within chromosome windows that are not filtered, may be counted. The number of coverage reads may be assigned a score per each mappable position. In cases involving barcodes, all sequences with the same barcode, physical properties or combination of the two may be collapsed into one read, as they are all derived from the sample parent molecule. This step reduces biases which may have been introduced during any of the preceding steps, such as steps involving amplification. For example, if one molecule is amplified 10 times but another is amplified 1000 times, each molecule is only represented once after collapse thereby negating the effect of uneven amplification. Only reads with unique barcodes may be counted for each mappable position and influence the assigned score.

Consensus sequences can be generated from families of sequence reads by any method known in the art. Such methods include, for example, linear or non-linear methods of building consensus sequences (such as voting, averaging, statistical, maximum a posteriori or maximum likelihood detection, dynamic programming, Bayesian, hidden Markov or support vector machine methods, etc.) derived from digital communication theory, information theory, or bioinformatics.

After the sequence read coverage has been determined, a stochastic modeling algorithm is applied to convert the normalized nucleic acid sequence read coverage for each window region to the discrete copy number states. In some cases, this algorithm may comprise one or more of the following: Hidden Markov Model, dynamic programming, support vector machine, Bayesian network, trellis decoding, Viterbi decoding, expectation maximization, Kalman filtering methodologies and neural networks.

In step 112, the discrete copy number states of each window region can be utilized to identify copy number variation in the chromosomal regions. In some cases, all adjacent window regions with the same copy number can be merged into a segment to report the presence or absence of copy number variation state. In some cases, various windows can be filtered before they are merged with other segments.

In step 114, the copy number variation may be reported as graph, indicating various positions in the genome and a corresponding increase or decrease or maintenance of copy number variation at each respective position. Additionally, copy number variation may be used to report a percentage score indicating how much disease material (or nucleic acids having a copy number variation) exists in the cell free polynucleotide sample.

Figure 10:
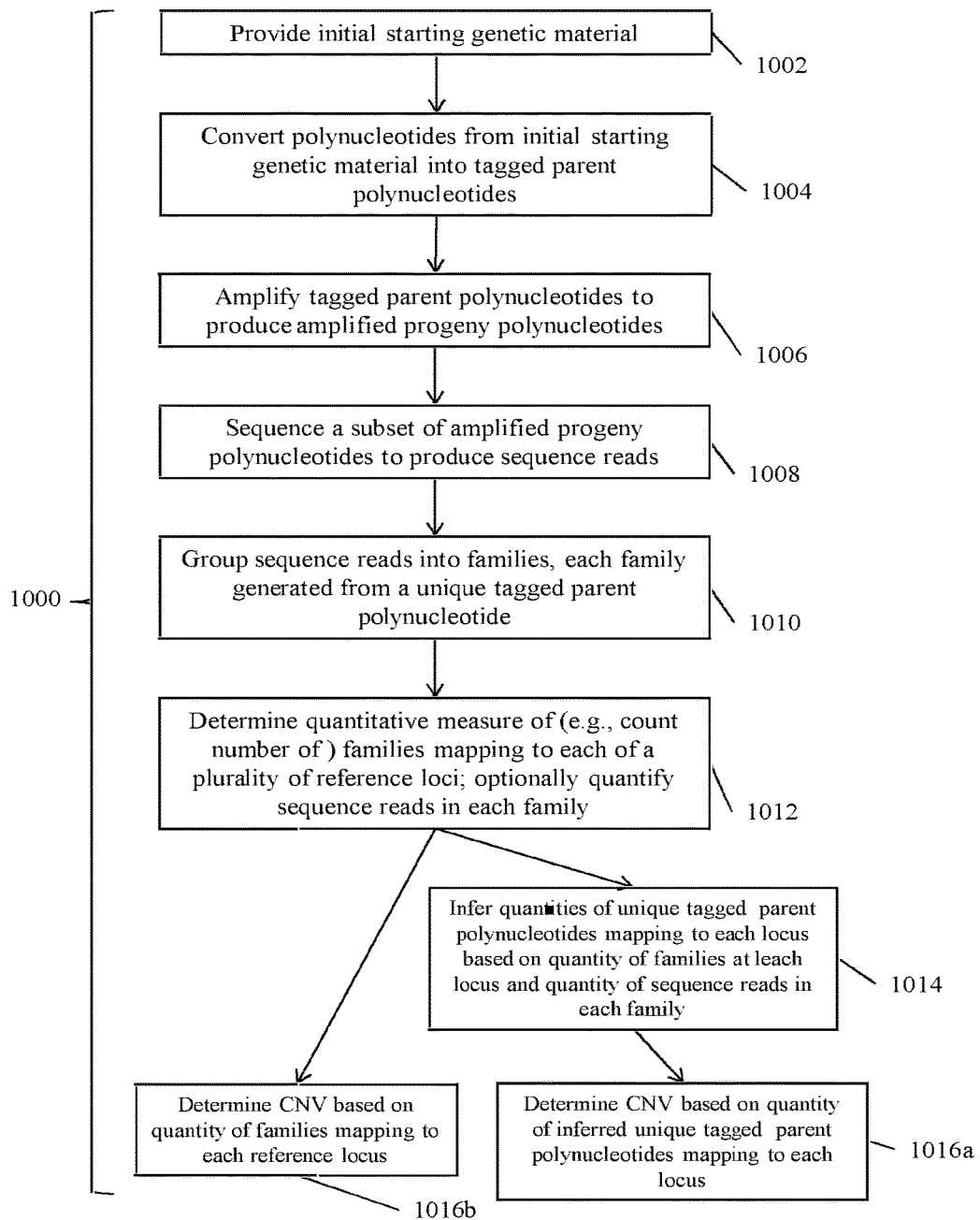
FIG. 10 is a flow chart representation of a method of reducing distortion in the determination of CNV from a set of sequence reads.

One method of determining copy number variation is shown in FIG. 10. In that method, after grouping sequence reads into families generated from a single parent polynucleotide (1010), the families are quantified, for example, by determining the number of families mapping to each of a plurality of different reference sequence locations. CNVs can be determined directly by comparing a quantitative measure of families at each of a plurality of different loci (1016*b*). Alternatively, one can infer a quantitative measure of families in the population of tagged parent polynucleotides using both a quantitative measure of families and a quantitative measure of family members in each family, e.g., as discussed above. Then, CNV can be determined by comparing the inferred measure of quantity at the plurality of loci. In other embodiments, a hybrid approach can be taken whereby a similar inference of original quantity can be made following normalization for representational bias during the sequencing process, such as GC bias, etc B. Copy Number Variation Detection Using Paired Sample Paired sample copy number variation detection shares many of the steps and parameters as the single sample approach described herein. However, as depicted in 200 of FIG. 2 of copy number variation detection using paired samples requires comparison of sequence coverage to a control sample rather than comparing it the predicted mappability of the genome. This approach may aid in normalization across windows.

Figure 2:
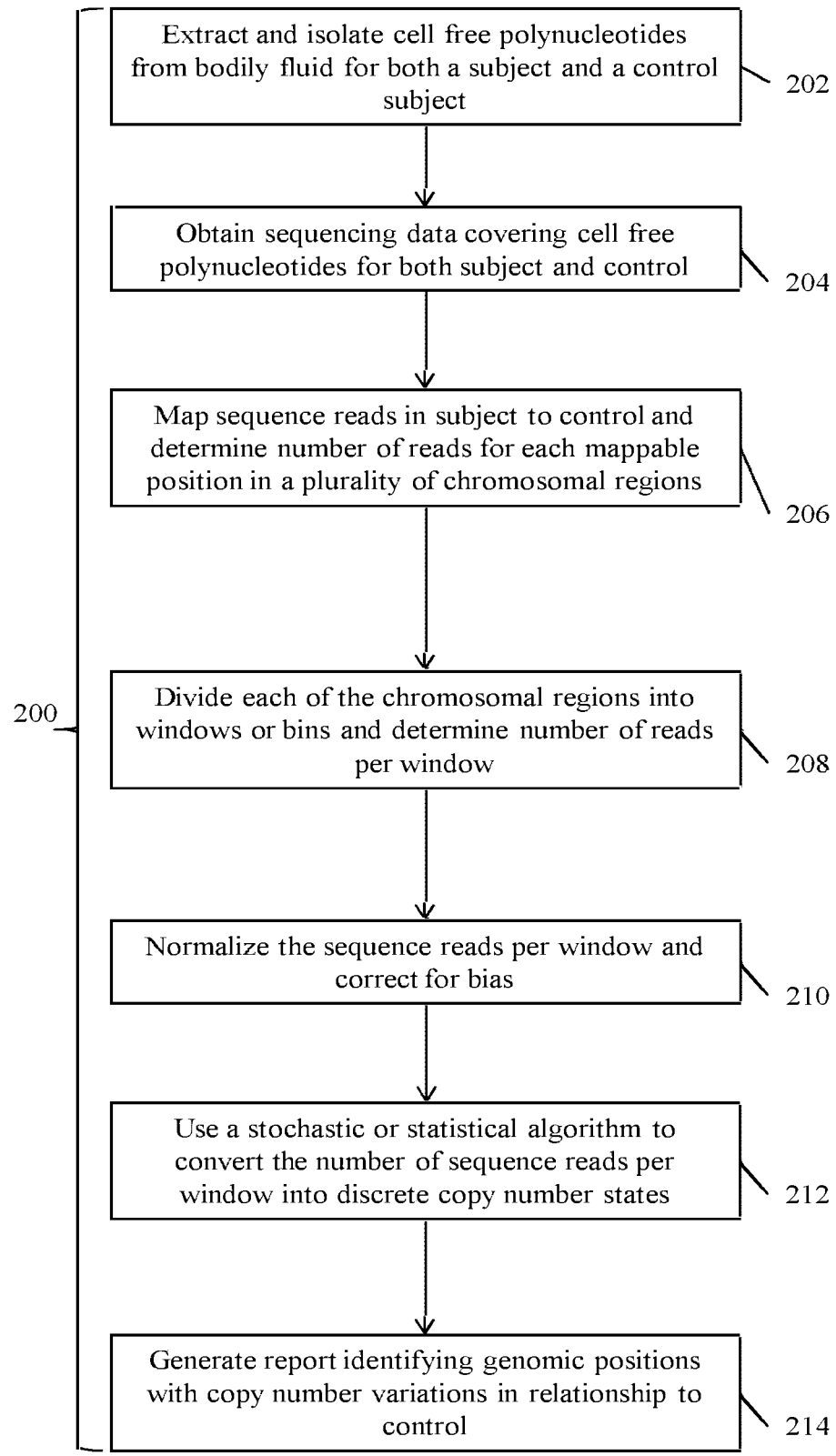
FIG. 2 is a flow chart representation of a method of detection of copy number variation using paired samples.

FIG. 2. is a diagram, 200 showing a strategy for detection of copy number variation in paired subject. As shown herein, copy number variation detection methods can be implemented as follows. In step 204, a single unique sample can be sequenced by a nucleic acid sequencing platform known in the art after extraction and isolation of the sample in step 202. This step generates a plurality of genomic fragment sequence reads. Additionally, a sample or control sample is taken from another subject. In some cases, the control subject may be a subject not known to have disease, whereas the other subject may have or be at risk for a particular disease. In some cases, these sequences reads may contain barcode information. In other examples, barcodes are not utilized. After sequencing, reads are assigned a quality score. In some cases, some reads are not of sufficient quality or length to perform the subsequent mapping step. Sequencing reads with a quality score at least 90%, 95%, 99%, 99.9%, 99.99% or 99.999% may be filtered out of the data set. In other cases, sequencing reads assigned a quality scored less than 90%, 95%, 99%, 99.9%, 99.99% or 99.999% may be filtered out of the data set. In step 206, the genomic fragment reads that meet a specified quality score threshold are mapped to a reference genome, or a template sequence that is known not to contain copy number variations. After mapping alignment, sequence reads are assigned a mapping score. In instances, reads may be sequences unrelated to copy number variation analysis. For example, some sequence reads may originate from contaminant polynucleotides. Sequencing reads with a mapping score at least 90%, 95%, 99%, 99.9%, 99.99% or 99.999% may be filtered out of the data set. In other cases, sequencing reads assigned a mapping scored less than 90%, 95%, 99%, 99.9%, 99.99% or 99.999% may be filtered out of the data set.

After data filtering and mapping, the plurality of sequence reads generates a chromosomal region of coverage for each of the test and control subjects. In step 208 these chromosomal regions may be divided into variable length windows or bins. A window or bin may be at least 5 kb, 10, kb, 25 kb, 30 kb, 35, kb, 40 kb, 50 kb, 60 kb, 75 kb, 100 kb, 150 kb, 200 kb, 500 kb, or 1000 kb. A window or bin may also be less than 5 kb, 10, kb, 25 kb, 30 kb, 35, kb, 40 kb, 50 kb, 60 kb, 75 kb, 100 kb, 150 kb, 200 kb, 500 kb, or 1000 kb.

For coverage normalization in step 210, each window or bin is selected to contain about the same number of mappable bases for each of the test and control subjects. In some cases, each window or bin in a chromosomal region may contain the exact number of mappable bases. In other cases, each window or bin may contain a different number of mappable bases. Additionally, each window or bin may be non-overlapping with an adjacent window or bin. In other cases, a window or bin may overlap with another adjacent window or bin. In some cases a window or bin may overlap by at least 1 bp, 2, bp, 3 bp, 4 bp, 5, bp, 10 bp, 20 bp, 25 bp, 50 bp, 100 bp, 200 bp, 250 bp, 500 bp, or 1000 bp. In other cases, a window or bin may overlap by less than 1 bp, 2, bp, 3 bp, 4 bp, 5, bp, 10 bp, 20 bp, 25 bp, 50 bp, 100 bp, 200 bp, 250 bp, 500 bp, or 1000 bp.

In some cases, each of the window regions is sized so they contain about the same number of uniquely mappable bases for each of the test and control subjects. The mappability of each base that comprise a window region is determined and used to generate a mappability file which contains a representation of reads from the references that are mapped back to the reference for each file. The mappability file contains one row per every position, indicating whether each position is or is not uniquely mappable.

Additionally, predefined windows, known throughout the genome to be hard to sequence, or contain a substantially high GC bias, are filtered from the data set. For example, regions known to fall near the centromere of chromosomes (i.e., centromeric DNA) are known to contain highly repetitive sequences that may produce false positive results. These regions may be filtered. Other regions of the genome, such as regions that contain an unusually high concentration of other highly repetitive sequences such as microsatellite DNA, may be filtered from the data set.

The number of windows analyzed may also vary. In some cases, at least 10, 20, 30, 40, 50, 100, 200, 500, 1000, 2000, 5,000, 10,000, 20,000, 50,000 or 100,000 windows are analyzed. In other cases, less than 10, 20, 30, 40, 50, 100, 200, 500, 1000, 2000, 5,000, 10,000, 20,000, 50,000 or 100,000 windows are analyzed.

For an exemplary genome derived from cell free polynucleotide sequences, the next step comprises determining read coverage for each window region for each of the test and control subjects. This may be performed using either reads with barcodes, or without barcodes. In cases without barcodes, the pervious mapping steps will provide coverage of different base positions. Sequence reads that have sufficient mapping and quality scores and fall within chromosome windows that are not filtered, may be counted. The number of coverage reads may be assigned a score per each mappable position. In cases involving barcodes, all sequences with the same barcode may be collapsed into one read, as they are all derived from the sample parent molecule. This step reduces biases which may have been introduced during any of the preceding steps, such as steps involving amplification. Only reads with unique barcodes may be counted for each mappable position and influence the assigned score. For this reason, it is important that the barcode ligation step be performed in a manner optimized for producing the lowest amount of bias.

In determining the nucleic acid read coverage for each window, the coverage of each window can be normalized by the mean coverage of that sample. Using such an approach, it may be desirable to sequence both the test subject and the control under similar conditions. The read coverage for each window may be then expressed as a ratio across similar windows Nucleic acid read coverage ratios for each window of the test subject can be determined by dividing the read coverage of each window region of the test sample with read coverage of a corresponding window region of the control ample.

After the sequence read coverage ratios have been determined, a stochastic modeling algorithm is applied to convert the normalized ratios for each window region into discrete copy number states. In some cases, this algorithm may comprise a Hidden Markov Model. In other cases, the stochastic model may comprise dynamic programming, support vector machine, Bayesian modeling, probabilistic modeling, trellis decoding, Viterbi decoding, expectation maximization, Kalman filtering methodologies, or neural networks.

In step 212, the discrete copy number states of each window region can be utilized to identify copy number variation in the chromosomal regions. In some cases, all adjacent window regions with the same copy number can be merged into a segment to report the presence or absence of copy number variation state. In some cases, various windows can be filtered before they are merged with other segments.

In step 214, the copy number variation may be reported as graph, indicating various positions in the genome and a corresponding increase or decrease or maintenance of copy number variation at each respective position. Additionally, copy number variation may be used to report a percentage score indicating how much disease material exists in the cell free poly nucleotide sample.

VI. Rare Mutation Detection

Figure 3:
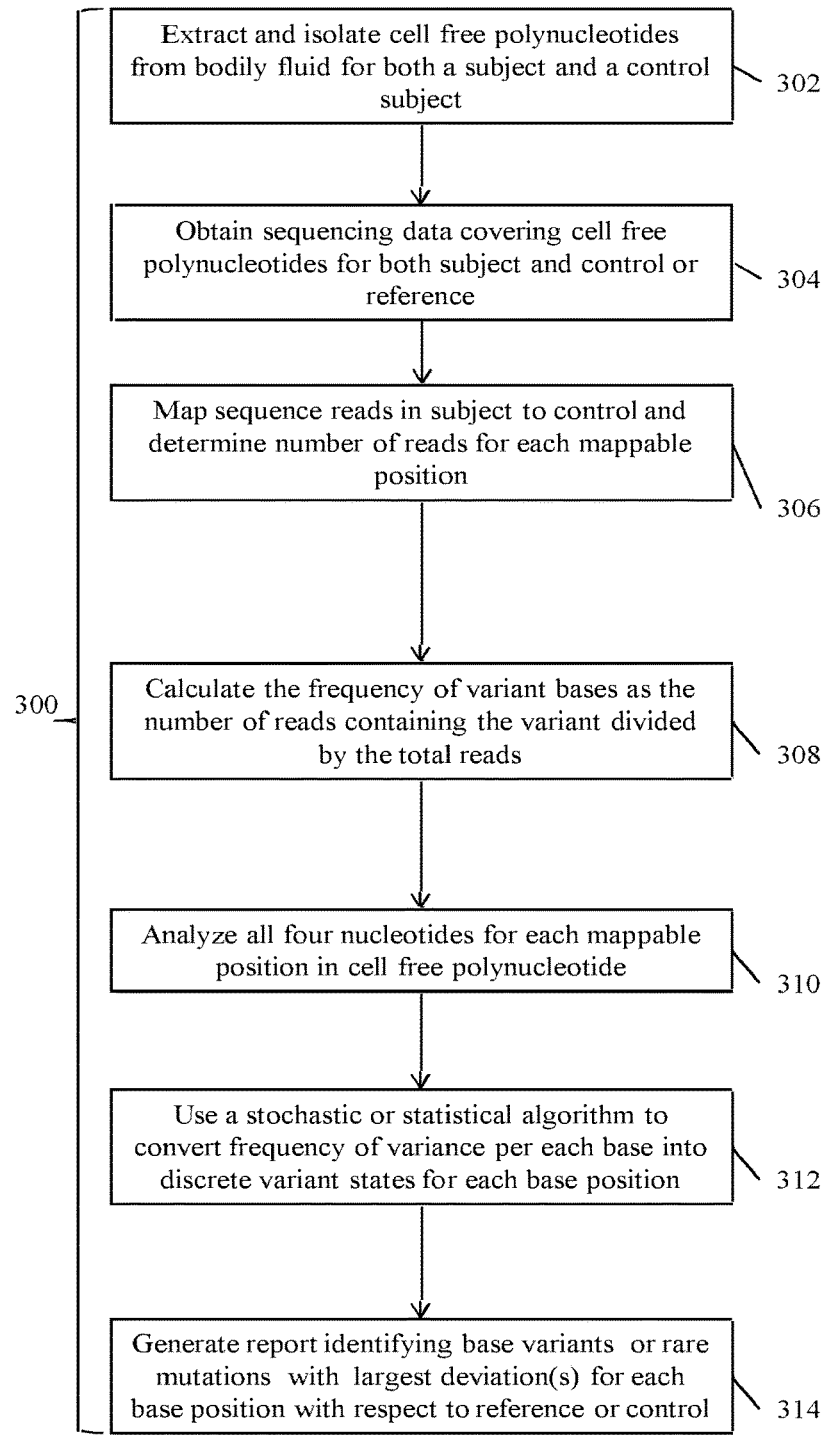
FIG. 3 is a flow chart representation of a method of detection of rare mutations (e.g., single nucleotide variants).

Rare mutation detection shares similar features as both copy number variation approaches. However, as depicted in FIG. 3, 300, rare mutation detection uses comparison of sequence coverage to a control sample or reference sequence rather than comparing it the relative mappability of the genome. This approach may aid in normalization across windows.

Generally, rare mutation detection may be performed on selectively enriched regions of the genome or transcriptome purified and isolated in step 302. As described herein, specific regions, which may include but are not limited to genes, oncogenes, tumor suppressor genes, promoters, regulatory sequence elements, non-coding regions, miRNAs, snRNAs and the like may be selectively amplified from a total population of cell free polynucleotides. This may be performed as herein described. In one example, multiplex sequencing may be used, with or without barcode labels for individual polynucleotide sequences. In other examples, sequencing may be performed using any nucleic acid sequencing platforms known in the art. This step generates a plurality of genomic fragment sequence reads as in step 304. Additionally, a reference sequence is obtained from a control sample, taken from another subject. In some cases, the control subject may be a subject known to not have known genetic aberrations or disease. In some cases, these sequence reads may contain barcode information. In other examples, barcodes are not utilized. After sequencing, reads are assigned a quality score. A quality score may be a representation of reads that indicates whether those reads may be useful in subsequent analysis based on a threshold. In some cases, some reads are not of sufficient quality or length to perform the subsequent mapping step. Sequencing reads with a quality score at least 90%, 95%, 99%, 99.9%, 99.99% or 99.999% may be filtered out of the data set. In other cases, sequencing reads assigned a quality scored at least 90%, 95%, 99%, 99.9%, 99.99% or 99.999% may be filtered out of the data set. In step 306, the genomic fragment reads that meet a specified quality score threshold are mapped to a reference genome, or a reference sequence that is known not to contain rare mutations. After mapping alignment, sequence reads are assigned a mapping score. A mapping score may be a representation or reads mapped back to the reference sequence indicating whether each position is or is not uniquely mappable. In instances, reads may be sequences unrelated to rare mutation analysis. For example, some sequence reads may originate from contaminant polynucleotides. Sequencing reads with a mapping score at least 90%, 95%, 99%, 99.9%, 99.99% or 99.999% may be filtered out of the data set. In other cases, sequencing reads assigned a mapping scored less than 90%, 95%, 99%, 99.9%, 99.99% or 99.999% may be filtered out of the data set.

For each mappable base, bases that do not meet the minimum threshold for mappability, or low quality bases, may be replaced by the corresponding bases as found in the reference sequence.

After data filtering and mapping, variant bases found between the sequence reads obtained from the subject and the reference sequence are analyzed.

For an exemplary genome derived from cell free polynucleotide sequences, the next step comprises determining read coverage for each mappable base position. This may be performed using either reads with barcodes, or without barcodes. In cases without barcodes, the previous mapping steps will provide coverage of different base positions. Sequence reads that have sufficient mapping and quality scores may be counted. The number of coverage reads may be assigned a score per each mappable position. In cases involving barcodes, all sequences with the same barcode may be collapsed into one consensus read, as they are all derived from the sample parent molecule. The sequence for each base is aligned as the most dominant nucleotide read for that specific location. Further, the number of unique molecules can be counted at each position to derive simultaneous quantification at each position. This step reduces biases which may have been introduced during any of the preceding steps, such as steps involving amplification. Only reads with unique barcodes may be counted for each mappable position and influence the assigned score.

Once read coverage may be ascertained and variant bases relative to the control sequence in each read are identified, the frequency of variant bases may be calculated as the number of reads containing the variant divided by the total number of reads. This may be expressed as a ratio for each mappable position in the genome.

For each base position, the frequencies of all four nucleotides, cytosine, guanine, thymine, adenine are analyzed in comparison to the reference sequence. A stochastic or statistical modeling algorithm is applied to convert the normalized ratios for each mappable position to reflect frequency states for each base variant. In some cases, this algorithm may comprise one or more of the following: Hidden Markov Model, dynamic programming, support vector machine, Bayesian or probabilistic modeling, trellis decoding, Viterbi decoding, expectation maximization, Kalman filtering methodologies, and neural networks.

In step 312, the discrete rare mutation states of each base position can be utilized to identify a base variant with high frequency of variance as compared to the baseline of the reference sequence. In some cases, the baseline might represent a frequency of at least 0.0001%, 0.001%, 0.01%, 0.1%, 1.0%, 2.0%, 3.0%, 4.0% 5.0%, 10%, or 25%. In other cases the baseline might represent a frequency of at least 0.0001%, 0.001%, 0.01%, 0.1%, 1.0%, 2.0%, 3.0%, 4.0% 5.0%. 10%, or 25%. In some cases, all adjacent base positions with the base variant or mutation can be merged into a segment to report the presence or absence of a rare mutation. In some cases, various positions can be filtered before they are merged with other segments.

After calculation of frequencies of variance for each base position, the variant with largest deviation for a specific position in the sequence derived from the subject as compared to the reference sequence is identified as a rare mutation. In some cases, a rare mutation may be a cancer mutation. In other cases, a rare mutation might be correlated with a disease state.

A rare mutation or variant may comprise a genetic aberration that includes, but is not limited to a single base substitution, or small indels, transversions, translocations, inversion, deletions, truncations or gene truncations. In some cases, a rare mutation may be at most 1, 2, 3, 4, 5, 6, 7, 8, 9, 10, 15 or 20 nucleotides in length. On other cases a rare mutation may be at least 1, 2, 3, 4, 5, 6, 7, 8, 9, 10, 15 or 20 nucleotides in length.

In step 314, the presence or absence of a mutation may be reflected in graphical form, indicating various positions in the genome and a corresponding increase or decrease or maintenance of a frequency of mutation at each respective position. Additionally, rare mutations may be used to report a percentage score indicating how much disease material exists in the cell free polynucleotide sample. A confidence score may accompany each detected mutation, given known statistics of typical variances at reported positions in non-disease reference sequences. Mutations may also be ranked in order of abundance in the subject or ranked by clinically actionable importance.

Figure 11:
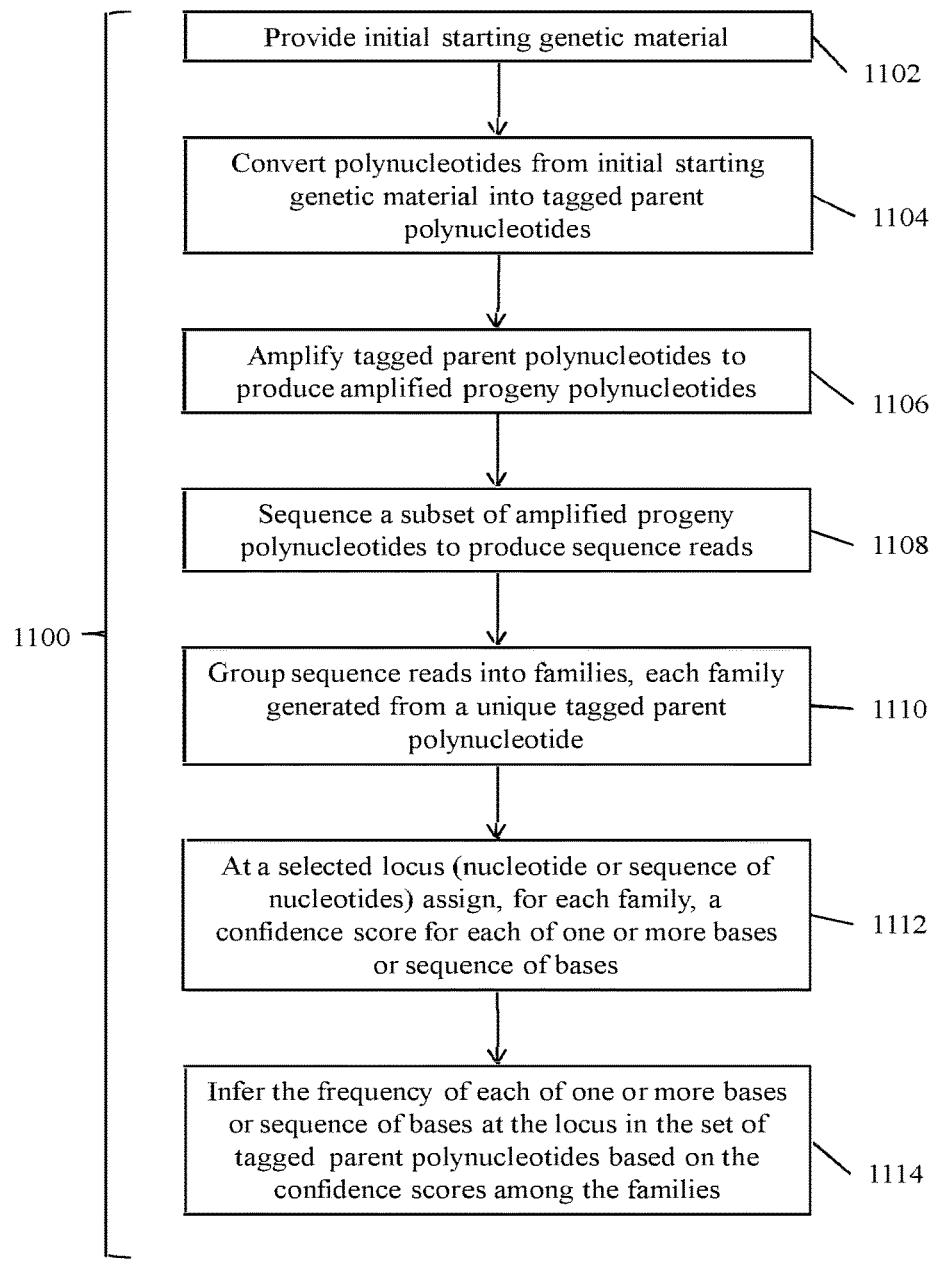
FIG. 11 is a flow chart representation of a method of estimating frequency of a base or sequence of bases at a locus in a tagged parent polynucleotide population from a set of sequence reads.
Figure 12:
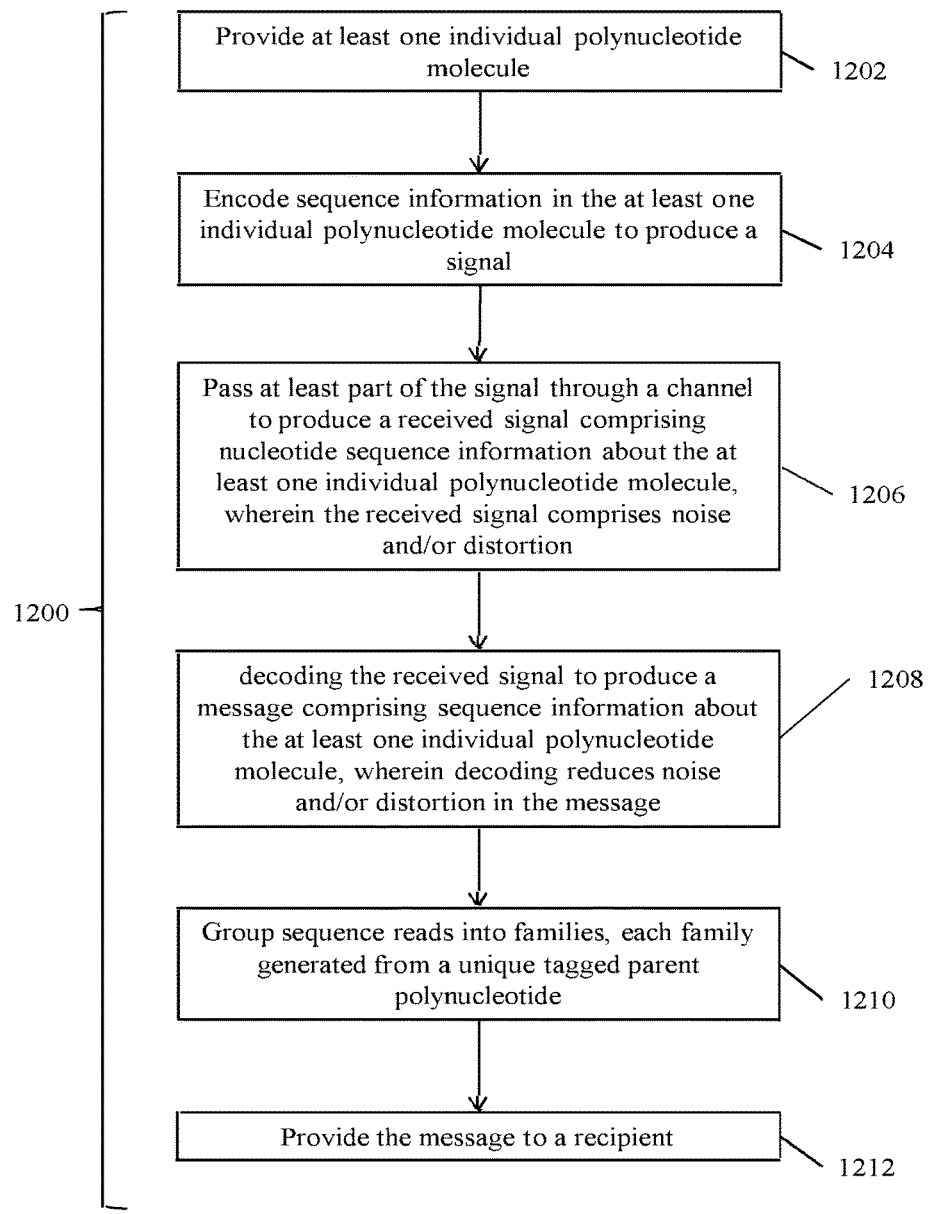
FIG. 12 shows a method of communicating sequence information.

FIG. 11 shows a method of inferring the frequency of a base or sequence of bases at a particular locus in a population polynucleotides. Sequence reads are grouped into families generated from an original tagged polynucleotide (1110). For each family, one or more bases at the locus is each assigned a confidence score. The confidence score can be assigned by any of a number of known statistical methods is assigned and can be based, at least in part, on the frequency at which a base appears among the sequence reads belonging to the family (1112). For example, the confidence score can be the frequency at which the base appears among the sequence reads. As another example, for each family, a hidden Markov model can be built, such that a maximum likelihood or maximum a posteriori decision can be made based on the frequency of occurrence of a particular base in a single family. As part of this model, the probability of error and resultant confidence score for a particular decision can be output as well. A frequency of the base in the original population can then be assigned based on the confidence scores among the families (1114).

VII. Applications

A. Early Detection of Cancer

Numerous cancers may be detected using the methods and systems described herein. Cancers cells, as most cells, can be characterized by a rate of turnover, in which old cells die and replaced by newer cells. Generally dead cells, in contact with vasculature in a given subject, may release DNA or fragments of DNA into the blood stream. This is also true of cancer cells during various stages of the disease. Cancer cells may also be characterized, dependent on the stage of the disease, by various genetic aberrations such as copy number variation as well as rare mutations. This phenomenon may be used to detect the presence or absence of cancers individuals using the methods and systems described herein.

For example, blood from subjects at risk for cancer may be drawn and prepared as described herein to generate a population of cell free polynucleotides. In one example, this might be cell free DNA. The systems and methods of the disclosure may be employed to detect rare mutations or copy number variations that may exist in certain cancers present. The method may help detect the presence of cancerous cells in the body, despite the absence of symptoms or other hallmarks of disease.

The types and number of cancers that may be detected may include but are not limited to blood cancers, brain cancers, lung cancers, skin cancers, nose cancers, throat cancers, liver cancers, bone cancers, lymphomas, pancreatic cancers, skin cancers, bowel cancers, rectal cancers, thyroid cancers, bladder cancers, kidney cancers, mouth cancers, stomach cancers, solid state tumors, heterogeneous tumors, homogenous tumors and the like.

In the early detection of cancers, any of the systems or methods herein described, including rare mutation detection or copy number variation detection may be utilized to detect cancers. These system and methods may be used to detect any number of genetic aberrations that may cause or result from cancers. These may include but are not limited to mutations, rare mutations, indels, copy number variations, transversions, translocations, inversion, deletions, aneuploidy, partial aneuploidy, polyploidy, chromosomal instability, chromosomal structure alterations, gene fusions, chromosome fusions, gene truncations, gene amplification, gene duplications, chromosomal lesions, DNA lesions, abnormal changes in nucleic acid chemical modifications, abnormal changes in epigenetic patterns, abnormal changes in nucleic acid methylation infection and cancer.

Additionally, the systems and methods described herein may also be used to help characterize certain cancers. Genetic data produced from the system and methods of this disclosure may allow practitioners to help better characterize a specific form of cancer. Often times, cancers are heterogeneous in both composition and staging. Genetic profile data may allow characterization of specific sub-types of cancer that may be important in the diagnosis or treatment of that specific sub-type. This information may also provide a subject or practitioner clues regarding the prognosis of a specific type of cancer.

B. Cancer Monitoring and Prognosis

The systems and methods provided herein may be used to monitor already known cancers, or other diseases in a particular subject. This may allow either a subject or practitioner to adapt treatment options in accord with the progress of the disease. In this example, the systems and methods described herein may be used to construct genetic profiles of a particular subject of the course of the disease. In some instances, cancers can progress, becoming more aggressive and genetically unstable. In other examples, cancers may remain benign, inactive, dormant or in remission. The system and methods of this disclosure may be useful in determining disease progression, remission or recurrence.

Further, the systems and methods described herein may be useful in determining the efficacy of a particular treatment option. In one example, successful treatment options may actually increase the amount of copy number variation or rare mutations detected in subject's blood if the treatment is successful as more cancers may die and shed DNA. In other examples, this may not occur. In another example, perhaps certain treatment options may be correlated with genetic profiles of cancers over time. This correlation may be useful in selecting a therapy. Additionally, if a cancer is observed to be in remission after treatment, the systems and methods described herein may be useful in monitoring residual disease or recurrence of disease.

For example, mutations occurring within a range of frequency beginning at threshold level can be determined from DNA in a sample from a subject, e.g., a patient. The mutations can be, e.g., cancer related mutations. The frequency can range from, for example, at least 0.1%, at least 1%, or at least 5% to 100%. The sample can be, e.g., cell free DNA or a tumor sample. A course of treatment can be prescribed based on any or all of mutations occurring within the frequency range including, e.g., their frequencies. A sample can be taken from the subject at any subsequent time. Mutations occurring within the original range of frequency or a different range of frequency can be determined. The course of treatment can be adjusted based on the subsequent measurements.

C. Early Detection and Monitoring of Other Diseases or Disease States

The methods and systems described herein may not be limited to detection of rare mutations and copy number variations associated with only cancers. Various other diseases and infections may result in other types of conditions that may be suitable for early detection and monitoring. For example, in certain cases, genetic disorders or infectious diseases may cause a certain genetic mosaicism within a subject. This genetic mosaicism may cause copy number variation and rare mutations that could be observed. In another example, the system and methods of the disclosure may also be used to monitor the genomes of immune cells within the body. Immune cells, such as B cells, may undergo rapid clonal expansion upon the presence certain diseases. Clonal expansions may be monitored using copy number variation detection and certain immune states may be monitored. In this example, copy number variation analysis may be performed over time to produce a profile of how a particular disease may be progressing.

Further, the systems and methods of this disclosure may also be used to monitor systemic infections themselves, as may be caused by a pathogen such as a bacteria or virus. Copy number variation or even rare mutation detection may be used to determine how a population of pathogens are changing during the course of infection. This may be particularly important during chronic infections, such as HIV/AIDs or Hepatitis infections, whereby viruses may change life cycle state and/or mutate into more virulent forms during the course of infection.

Yet another example that the system and methods of this disclosure may be used for is the monitoring of transplant subjects. Generally, transplanted tissue undergoes a certain degree of rejection by the body upon transplantation. The methods of this disclosure may be used to determine or profile rejection activities of the host body, as immune cells attempt to destroy transplanted tissue. This may be useful in monitoring the status of transplanted tissue as well as altering the course of treatment or prevention of rejection.

Further, the methods of the disclosure may be used to characterize the heterogeneity of an abnormal condition in a subject, the method comprising generating a genetic profile of extracellular polynucleotides in the subject, wherein the genetic profile comprises a plurality of data resulting from copy number variation and rare mutation analyses. In some cases, including but not limited to cancer, a disease may be heterogeneous. Disease cells may not be identical. In the example of cancer, some tumors are known to comprise different types of tumor cells, some cells in different stages of the cancer. In other examples, heterogeneity may comprise multiple foci of disease. Again, in the example of cancer, there may be multiple tumor foci, perhaps where one or more foci are the result of metastases that have spread from a primary site.

The methods of this disclosure may be used to generate or profile, fingerprint or set of data that is a summation of genetic information derived from different cells in a heterogeneous disease. This set of data may comprise copy number variation and rare mutation analyses alone or in combination.

D. Early Detection and Monitoring of Other Diseases or Disease States of Fetal Origin Additionally, the systems and methods of the disclosure may be used to diagnose, prognose, monitor or observe cancers or other diseases of fetal origin. That is, these methodologies may be employed in a pregnant subject to diagnose, prognose, monitor or observe cancers or other diseases in a unborn subject whose DNA and other polynucleotides may co-circulate with maternal molecules.

VIII. Terminology

The terminology used therein is for the purpose of describing particular embodiments only and is not intended to be limiting of a systems and methods of this disclosure. As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising".

Several aspects of a systems and methods of this disclosure are described above with reference to example applications for illustration. It should be understood that numerous specific details, relationships, and methods are set forth to provide a full understanding of a systems and methods. One having ordinary skill in the relevant art, however, will readily recognize that a systems and methods can be practiced without one or more of the specific details or with other methods. This disclosure is not limited by the illustrated ordering of acts or events, as some acts may occur in different orders and/or concurrently with other acts or events. Furthermore, not all illustrated acts or events are required to implement a methodology in accordance with this disclosure.

Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. The term "about" as used herein refers to a range that is 15% plus or minus from a stated numerical value within the context of the particular usage. For example, about 10 would include a range from 8.5 to 11.5.

Computer Systems

Figure 15:
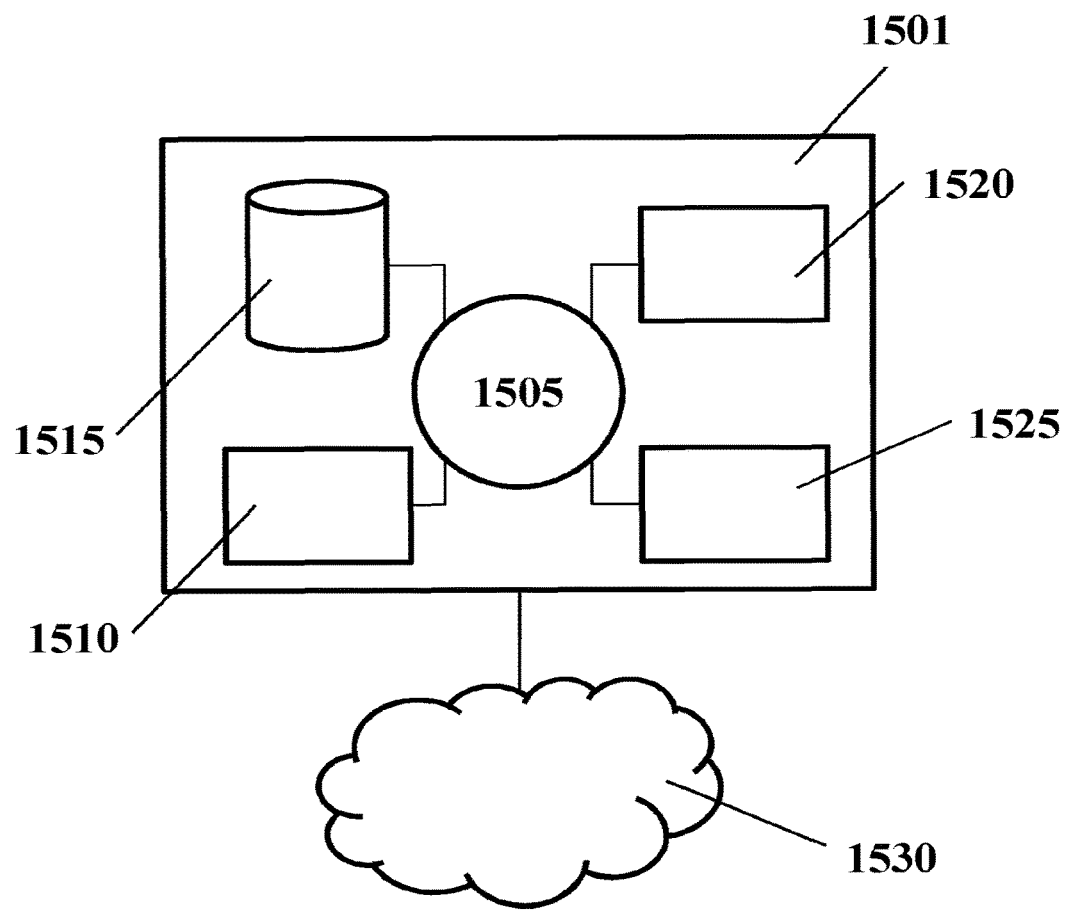
FIG. 15 shows a computer system that is programmed or otherwise configured to implement various methods of the present disclosure.

Methods of the present disclosure can be implemented using, or with the aid of, computer systems. FIG. 15 shows a computer system 1501 that is programmed or otherwise configured to implement the methods of the present disclosure. The computer system 1501 can regulate various aspects sample preparation, sequencing and/or analysis. In some examples, the computer system 1501 is configured to perform sample preparation and sample analysis, including nucleic acid sequencing.

The computer system 1501 includes a central processing unit (CPU, also "processor" and "computer processor" herein) 1505, which can be a single core or multi core processor, or a plurality of processors for parallel processing. The computer system 1501 also includes memory or memory location 1510 (e.g., random-access memory, read-only memory, flash memory), electronic storage unit 1515 (e.g., hard disk), communication interface 1520 (e.g., network adapter) for communicating with one or more other systems, and peripheral devices 1525, such as cache, other memory, data storage and/or electronic display adapters. The memory 1510, storage unit 1515, interface 1520 and peripheral devices 1525 are in communication with the CPU 1505 through a communication bus (solid lines), such as a motherboard. The storage unit 1515 can be a data storage unit (or data repository) for storing data. The computer system 1501 can be operatively coupled to a computer network ("network") 1530 with the aid of the communication interface 1520. The network 1530 can be the Internet, an internet and/or extranet, or an intranet and/or extranet that is in communication with the Internet. The network 1530 in some cases is a telecommunication and/or data network. The network 1530 can include one or more computer servers, which can enable distributed computing, such as cloud computing. The network 1530, in some cases with the aid of the computer system 1501, can implement a peer-to-peer network, which may enable devices coupled to the computer system 1501 to behave as a client or a server.

The CPU 1505 can execute a sequence of machine-readable instructions, which can be embodied in a program or software. The instructions may be stored in a memory location, such as the memory 1510. Examples of operations performed by the CPU 1505 can include fetch, decode, execute, and writeback.

The storage unit 1515 can store files, such as drivers, libraries and saved programs. The storage unit 1515 can store programs generated by users and recorded sessions, as well as output(s) associated with the programs. The storage unit 1515 can store user data, e.g., user preferences and user programs. The computer system 1501 in some cases can include one or more additional data storage units that are external to the computer system 1501, such as located on a remote server that is in communication with the computer system 1501 through an intranet or the Internet.

The computer system 1501 can communicate with one or more remote computer systems through the network 1530. For instance, the computer system 1501 can communicate with a remote computer system of a user (e.g., operator). Examples of remote computer systems include personal computers (e.g., portable PC), slate or tablet PC's (e.g., Apple® iPad, Samsung® Galaxy Tab), telephones, Smart phones (e.g., Apple® iPhone, Android-enabled device, Blackberry®), or personal digital assistants. The user can access the computer system 1501 via the network 1530.

Methods as described herein can be implemented by way of machine (e.g., computer processor) executable code stored on an electronic storage location of the computer system 1501, such as, for example, on the memory 1510 or electronic storage unit 1515. The machine executable or machine readable code can be provided in the form of software. During use, the code can be executed by the processor 1505. In some cases, the code can be retrieved from the storage unit 1515 and stored on the memory 1510 for ready access by the processor 1505. In some situations, the electronic storage unit 1515 can be precluded, and machine-executable instructions are stored on memory 1510.

The code can be pre-compiled and configured for use with a machine have a processor adapted to execute the code, or can be compiled during runtime. The code can be supplied in a programming language that can be selected to enable the code to execute in a pre-compiled or as-compiled fashion.

Aspects of the systems and methods provided herein, such as the computer system 1501, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system 1501 can include or be in communication with an electronic display that comprises a user interface (UI) for providing, for example, one or more results of sample analysis. Examples of UI's include, without limitation, a graphical user interface (GUI) and web-based user interface.

EXAMPLES

Example 1—Prostate Cancer Prognosis and Treatment

A blood sample is taken from a prostate cancer subject. Previously, an oncologist determines that the subject has stage II prostate cancer and recommends a treatment. Cell free DNA is extracted, isolated, sequenced and analyzed every 6 months after the initial diagnosis.

Cell free DNA is extracted and isolated from blood using the Qiagen Qubit kit protocol. A carrier DNA is added to increase yields. DNA is amplified using PCR and universal primers. 10 ng of DNA is sequenced using a massively parallel sequencing approach with an Illumina MiSeq personal sequencer. 90% of the subject's genome is covered through sequencing of cell free DNA.

Sequence data is assembled and analyzed for copy number variation. Sequence reads are mapped and compared to a healthy individual (control). Based on the number of sequence reads, chromosomal regions are divided into 50 kb non overlapping regions. Sequence reads are compared to one another and a ratio is determined for each mappable position.

A Hidden Markov Model is applied to convert copy numbers into discrete states for each window.

Figure 4A:
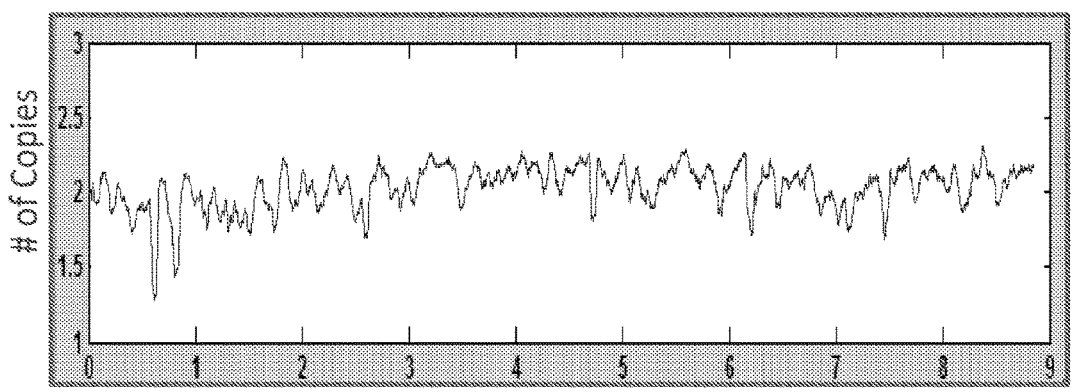
FIG. 4A is graphical copy number variation detection report generated from a normal, non cancerous subject.
Figure 4B:
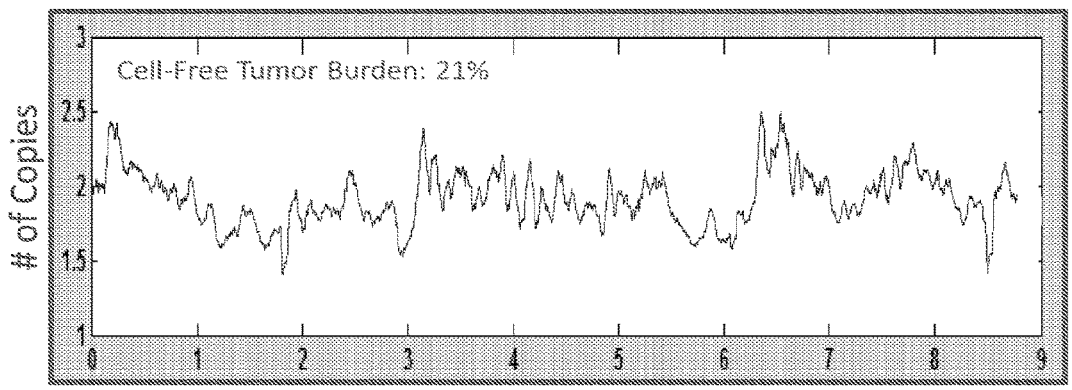
FIG. 4B is a graphical copy number variation detection report generated from a subject with prostate cancer.

Reports are generated, mapping genome positions and copy number variation show in FIG. 4A (for a healthy individual) and FIG. 4B for the subject with cancer.

These reports, in comparison to other profiles of subjects with known outcomes, indicate that this particular cancer is aggressive and resistant to treatment. The cell free tumor burden is 21%. The subject is monitored for 18 months. At month 18, the copy number variation profile begins to increase dramatically, from cell free tumor burden of 21% to 30%. A comparison is done with genetic profiles of other prostate subjects. It is determined that this increase in copy number variation indicates that the prostate cancer is advancing from stage II to stage III. The original treatment regiment as prescribed is no longer treating the cancer. A new treatment is prescribed.

Figure 4C:
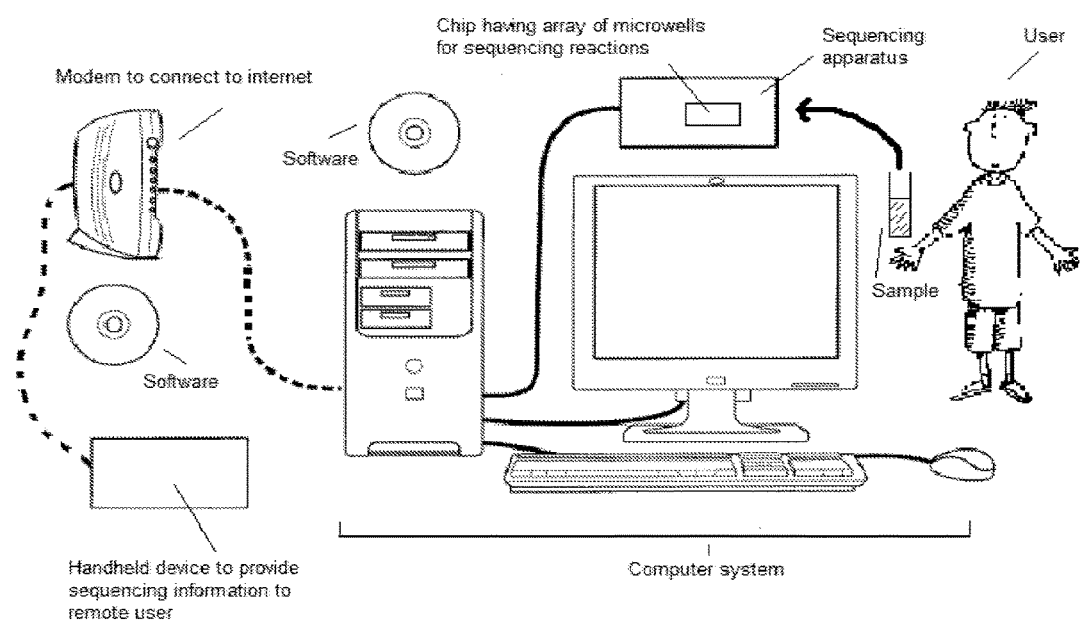
FIG. 4C is schematic representation of internet enabled access of reports generated from copy number variation analysis of a subject with prostate cancer.

Further, these reports are submitted and accessed electronically via the internet. Analysis of sequence data occurs at a site other than the location of the subject. The report is generated and transmitted to the subject's location. Via an internet enabled computer, the subject accesses the reports reflecting his tumor burden (FIG. 4C).

Example 2—Prostate Cancer Remission and Recurrence

A blood sample is taken from a prostate cancer survivor. The subject had previously undergone numerous rounds of chemotherapy and radiation. The subject at the time of testing did not present symptoms or health issues related to the cancer. Standard scans and assays reveal the subject to be cancer free.

Cell free DNA is extracted and isolated from blood using the Qiagen TruSeq kit protocol. A carrier DNA is added to increase yields. DNA is amplified using PCR and universal primers. 10 ng of DNA is sequenced using a massively parallel sequencing approach with an Illumina MiSeq personal sequencer. 12 mer barcodes are added to individual molecules using a ligation method.

Sequence data is assembled and analyzed for copy number variation. Sequence reads are mapped and compared to a healthy individual (control). Based on the number of sequence reads, chromosomal regions are divided into 40 kb non overlapping regions. Sequence reads are compared to one another and a ratio is determined for each mappable position.

Non unique barcoded sequences are collapsed into a single read to help normalize bias from amplification.

A Hidden Markov Model is applied to convert copy numbers into discrete states for each window.

Figure 5A:
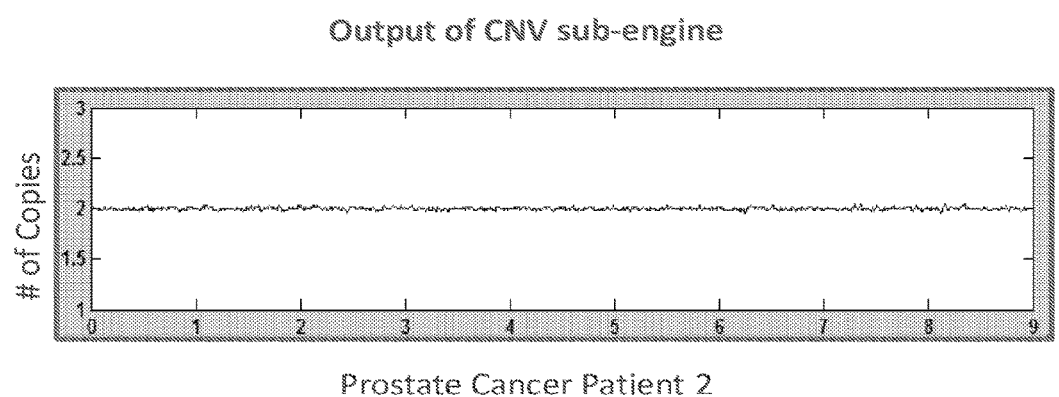
FIG. 5A is a graphical copy number variation detection report generated from a subject with prostate cancer remission.
Figure 5B:
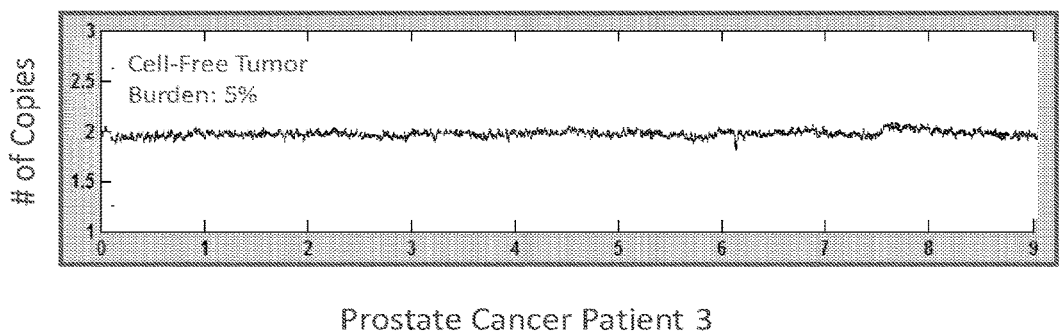
FIG. 5B is a graphical copy number variation detection report generated from a subject with prostate recurrence cancer.

Reports are generated, mapping genome positions and copy number variation shown in FIG. 5A, for a subject with cancer in remission and FIG. 5B for a subject with cancer in recurrence.

This report in comparison to other profiles of subjects with known outcomes indicates that at month 18, rare mutation analysis for copy number variation is detected at cell free tumor burden of 5%. An oncologist prescribes treatment again.

Example 3—Thyroid Cancer and Treatment

A subject is known to have Stage IV thyroid cancer and undergoes standard treatment, including radiation therapy with 1-131. CT scans are inconclusive as to whether the radiation therapy is destroying cancerous masses. Blood is drawn before and after the latest radiation session.

Cell free DNA is extracted and isolated from blood using the Qiagen Qubit kit protocol. A sample of non specific bulk DNA is added to the sample preparation reactions increase yields.

It is known that the BRAF gene may be mutated at amino acid position 600 in this thyroid cancer. From population of cell free DNA, BRAF DNA is selectively amplified using primers specific to the gene. 20mer barcodes are added to the parent molecule as a control for counting reads.

10 ng of DNA is sequenced using massively parallel sequencing approach with an Illumina MiSeq personal sequencer.

Sequence data is assembled and analyzed for copy number variation detection. Sequence reads are mapped and compared to a healthy individual (control). Based on the number of sequence reads, as determined by counting the barcode sequences, chromosomal regions are divided into 50 kb non overlapping regions. Sequence reads are compared to one another and a ratio is determined for each mappable position.

A Hidden Markov Model is applied to convert copy numbers into discrete states for each window.

A report is generated, mapping genome positions and copy number variation.

The reports generated before and after treatment are compared. The tumor cell burden percentage jumps from 30% to 60% after the radiation session. The jump in tumor burden is determined to be an increase in necrosis of cancer tissue versus normal tissue as a result of treatment. Oncologists recommend the subject continue the prescribed treatment.

Example 4—Sensitivity of Rare Mutation Detection

In order to determine the detection ranges of rare mutation present in a population of DNA, mixing experiments are performed. Sequences of DNA, some containing wildtype copies of the genes TP53, HRAS and MET and some containing copies with rare mutations in the same genes, are mixed together in distinct ratios. DNA mixtures are prepared such that ratios or percentages of mutant DNA to wildtype DNA range from 100% to 0.01%.

10 ng of DNA is sequenced for each mixing experiment using a massively parallel sequencing approach with an Illumina MiSeq personal sequencer.

Sequence data is assembled and analyzed for rare mutation detection. Sequence reads are mapped and compared to a reference sequence (control). Based on the number of sequence reads, the frequency of variance for each mappable position is determined.

A Hidden Markov Model is applied to convert frequency of variance for each mappable position into discrete states for base position.

Figure 6A:
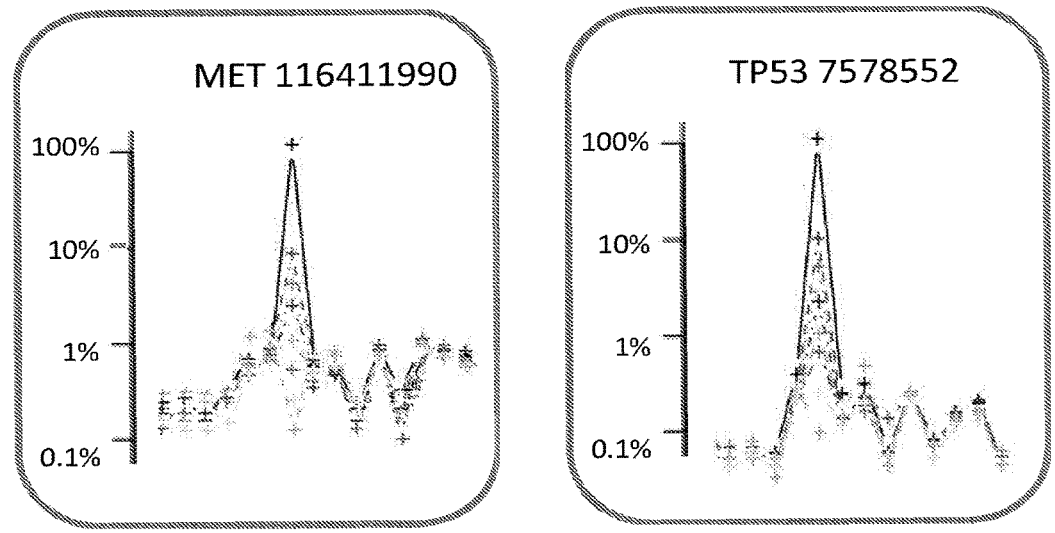
FIG. 6A is graphical detection report (e.g., for single nucleotide variants) generated from various mixing experiments using DNA samples containing both wildtype and mutant copies of MET and TP53.

A report is generated, mapping genome base positions and percentage detection of the rare mutation over baseline as determined by the reference sequence (FIG. 6A).

Figure 6B:
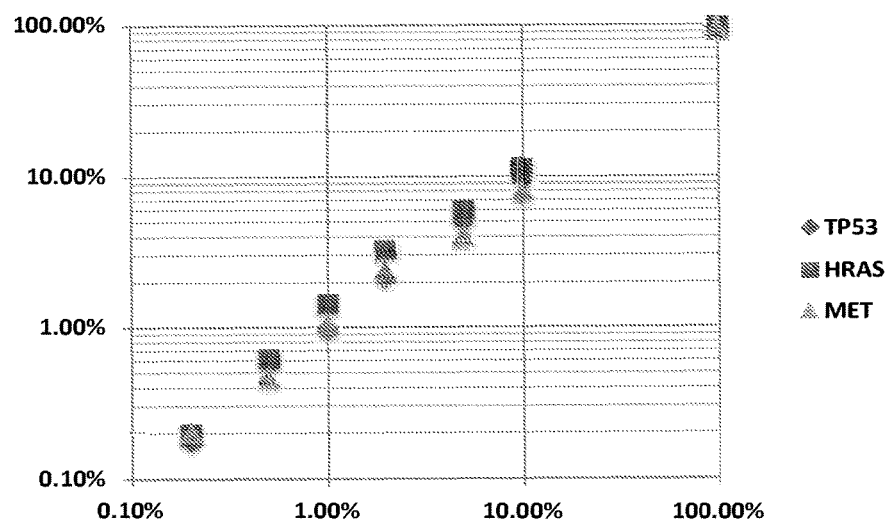
FIG. 6B is logarithmic graphical representation of (e.g., single nucleotide variant) detection results. Observed vs. expected percent cancer measurements are shown for various mixing experiments using DNAs samples containing both wildtype and mutant copies of MET, HRAS and TP53.

The results of various mixing experiments ranging from 0.1% to 100% are represented in a logarithmic scale graph, with measured percentage of DNA with a rare mutation graphed as a function of the actual percentage of DNA with a rare mutation (FIG. 6B). The three genes, TP53, HRAS and MET are represented. A strong linear correlation is found between measured and expected rare mutation populations. Additionally, a lower sensitivity threshold of about 0.1% of DNA with a rare mutation in a population of non mutated DNA is found with these experiments (FIG. 6B).

Example 5—Rare Mutation Detection in Prostate Cancer Subject

A subject is thought to have early stage prostate cancer. Other clinical tests provide inconclusive results. Blood is drawn from the subject and cell free DNA is extracted, isolated, prepared and sequenced.

A panel of various oncogenes and tumor suppressor genes are selected for selective amplification using a TaqMan© PCR kit (Invitrogen) using gene specific primers. DNA regions amplified include DNA containing PIK3CA and TP53 genes.

10 ng of DNA is sequenced using a massively parallel sequencing approach with an Illumina MiSeq personal sequencer.

Sequence data is assembled and analyzed for rare mutation detection. Sequence reads are mapped and compared to a reference sequence (control). Based on the number of sequence reads, the frequency of variance for each mappable position was determined.

A Hidden Markov Model is applied to convert frequency of variance for each mappable position into discrete states for each base position.

Figure 7A:
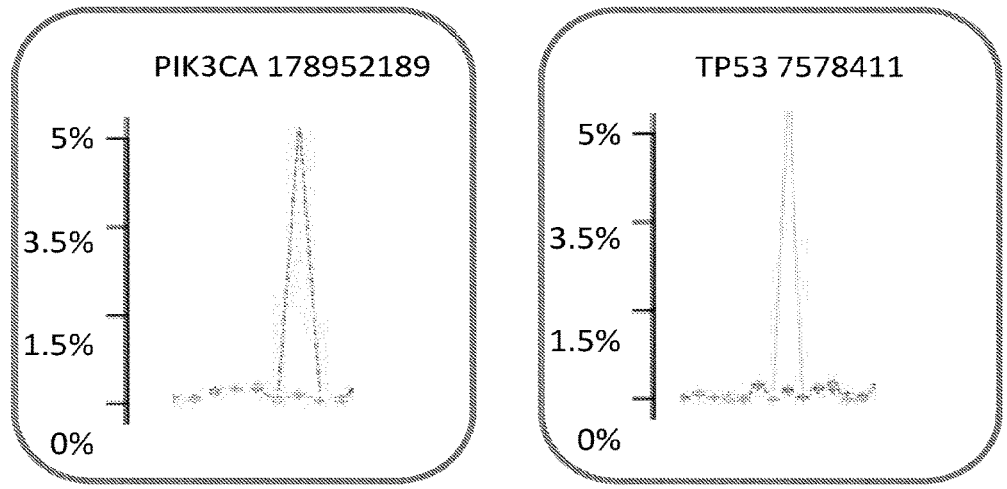
FIG. 7A is graphical report of percentage of two (e.g., single nucleotide variants) in two genes, PIK3CA and TP53, in a subject with prostate cancer as compared to a reference (control).

A report is generated, mapping genomic base positions and percentage detection of the rare mutation over baseline as determined by the reference sequence (FIG. 7A). Rare mutations are found at an incidence of 5% in two genes, PIK3CA and TP53, respectively, indicating that the subject has an early stage cancer. Treatment is initiated.

Figure 7B:
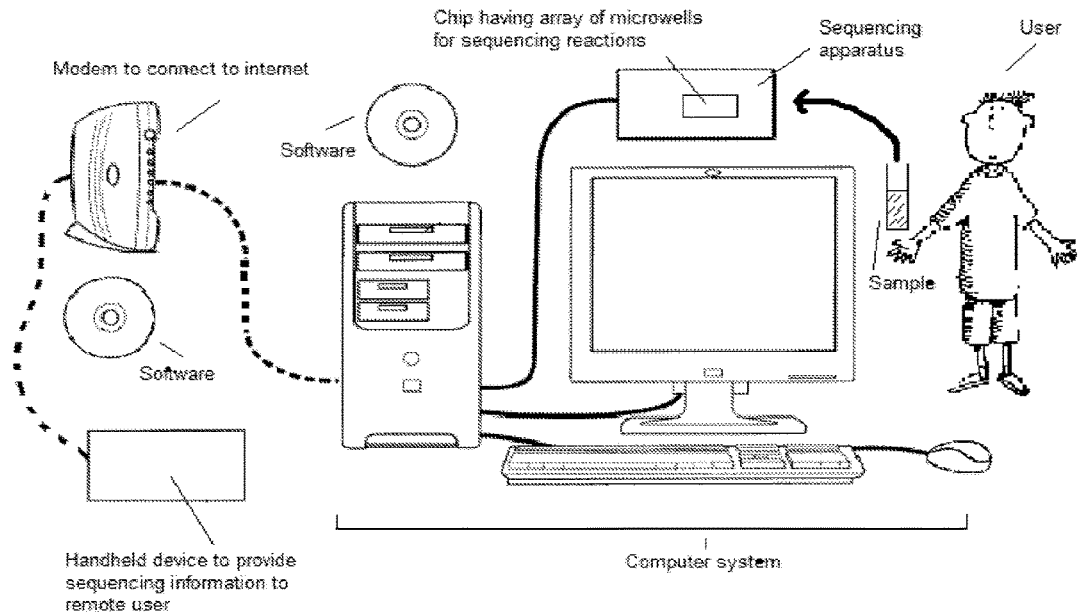
FIG. 7B is schematic representation of internet enabled access of reports generated from (e.g., single nucleotide variant) analysis of a subject with prostate cancer.

Further, these reports are submitted and accessed electronically via the internet. Analysis of sequence data occurs at a site other than the location of the subject. The report is generated and transmitted to the subject's location. Via an internet enabled computer, the subject accesses the reports reflecting his tumor burden (FIG. 7B).

Example 6—Rare Mutation Detection in Colorectal Cancer Subjects

A subject is thought to have mid-stage colorectal cancer. Other clinical tests provide inconclusive results. Blood is drawn from the subject and cell free DNA is extracted.

10 ng of the cell-free genetic material that is extracted from a single tube of plasma is used. The initial genetic material is converted into a set of tagged parent polynucleotides. The tagging included attaching tags required for sequencing as well as non-unique identifiers for tracking progeny molecules to the parent nucleic acids. The conversion is performed through an optimized ligation reaction as described above and conversion yield is confirmed by looking at the size profile of molecules post-ligation. Conversion yield is measured as the percentage of starting initial molecules that have both ends ligated with tags. Conversion using this approach is performed at high efficiency, for example, at least 50%.

The tagged library is PCR-amplified and enriched for genes most associated with colorectal cancer, (e.g., KRAS, APC, TP53, etc) and the resulting DNA is sequenced using a massively parallel sequencing approach with an Illumina MiSeq personal sequencer.

Sequence data is assembled and analyzed for rare mutation detection. Sequence reads are collapsed into familial groups belonging to a parent molecule (as well as error-corrected upon collapse) and mapped using a reference sequence (control). Based on the number of sequence reads, the frequency of rare variations (substitutions, insertions, deletions, etc) and variations in copy number and heterozygosity (when appropriate) for each mappable position is determined.

A report is generated, mapping genomic base positions and percentage detection of the rare mutation over baseline as determined by the reference sequence. Rare mutations are found at an incidence of 0.3-0.4% in two genes, KRAS and FBXW7, respectively, indicating that the subject has residual cancer. Treatment is initiated.

Further, these reports are submitted and accessed electronically via the internet. Analysis of sequence data occurs at a site other than the location of the subject. The report is generated and transmitted to the subject's location. Via an internet enabled computer, the subject accesses the reports reflecting his tumor burden.

Example 7—Digital Sequencing Technology

The concentrations of tumor-shed nucleic acids are typically so low that current next-generation sequencing technologies can only detect such signals sporadically or in patients with terminally high tumor burden. The main reason being that such technologies are plagued by error rates and bias that can be orders of magnitude higher than what is required to reliably detect de novo genetic alterations associated with cancer in circulating DNA. Shown here is a new sequencing methodology, Digital Sequencing Technology (DST), which increases the sensitivity and specificity of detecting and quantifying rare tumor-derived nucleic acids among germline fragments by at least 1-2 orders of magnitude.

DST architecture is inspired by state-of-the-art digital communication systems that combat the high noise and distortion caused by modern communication channels and are able to transmit digital information flawlessly at exceedingly high data rates. Similarly, current next-gen workflows are plagued by extremely high noise and distortion (due to sample-prep, PCR-based amplification and sequencing). Digital sequencing is able to eliminate the error and distortion created by these processes and produce near-perfect representation of all rare variants (including CNVs).

High-Diversity Library Preparation

Unlike conventional sequencing library preparation protocols, whereby the majority of extracted circulating DNA fragments are lost due to inefficient library conversion, our Digital Sequencing Technology workflow enables the vast majority of starting molecules to be converted and sequenced. This is critically important for detection of rare variants as there may only be a handful of somatically mutated molecules in an entire 10 mL tube of blood. The efficient molecular biology conversion process developed enables the highest possible sensitivity for detection of rare variants.

Comprehensive Actionable Oncogene Panel

The workflow engineered around the DST platform is flexible and highly tunable as targeted regions can be as small as single exons or as broad as whole exomes (or even whole genomes). A standard panel consists of all exonic bases of 15 actionable cancer-related genes and coverage of the "hot" exons of an additional 36 onco-/tumor-suppressor genes (e.g., exons containing at least one or more reported somatic mutations in COSMIC).

Example 8: Analytical Studies

Figure 13A:
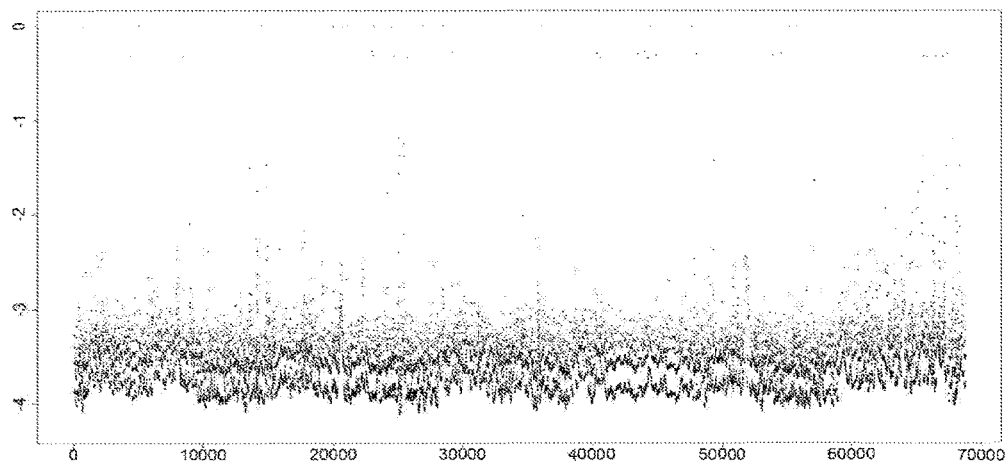
FIGS. 13A and 13B show detected minor allele frequencies across an entire 70 kb panel in 0.3% LNCaP cfDNA titration using standard sequencing and Digital Sequencing workflows. Standard "analog" sequencing (FIG. 13A) masks all true-positive rare variants in tremendous noise due to PCR and sequencing errors despite Q30 filtering. Digital Sequencing (FIG. 13B) eliminates all PCR and sequencing noise, revealing true mutations with no false positives: green circles are SNP points in normal cfDNA and red circles are detected LNCaP mutations.
Figure 13B:
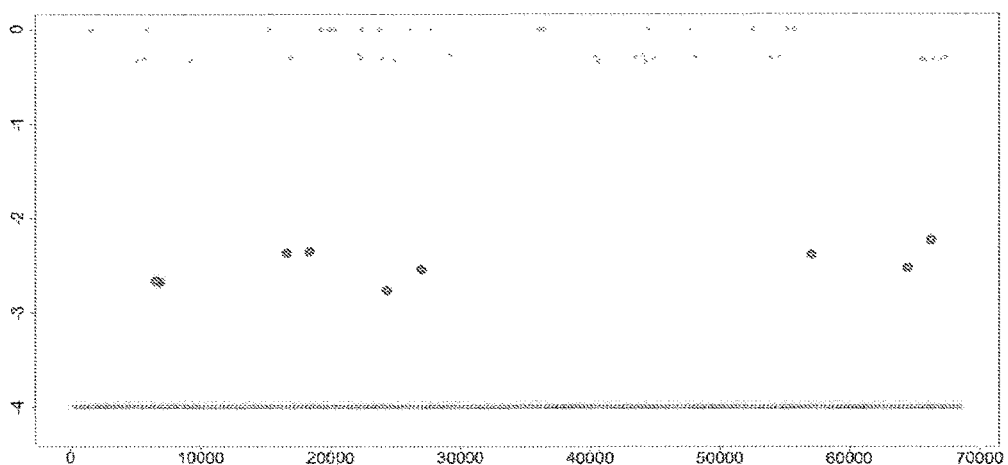
Figure 14:
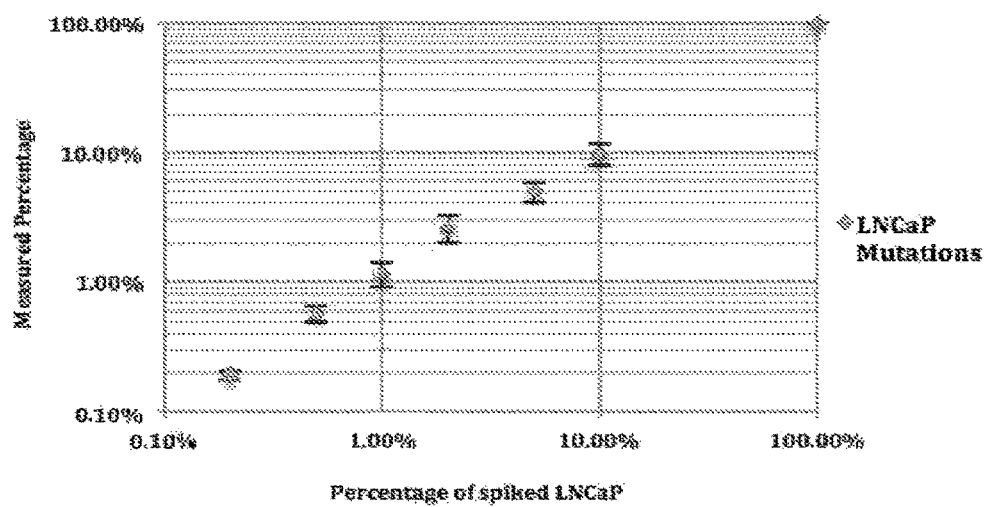
FIG. 14: Shows titration of LNCap cfDNA.

To study the performance of our technology, its sensitivity in analytical samples was evaluated. We spiked varying amounts of LNCaP cancer cell line DNA into a background of normal cfDNA and were able to successfully detect somatic mutations down to 0.1% sensitivity (see FIG. 13).

Preclinical Studies

The concordance of circulating DNA with tumor gDNA in human xenograft models in mice was investigated. In seven CTC-negative mice, each with one of two different human breast cancer tumors, all somatic mutations detected in tumor gDNA were also detected in mouse blood cfDNA using DST further validating the utility of cfDNA for non-invasive tumor genetic profiling.

Pilot Clinical Studies

Correlation of Tumor Biopsy Vs. Circulating DNA Somatic Mutations

A pilot study was initiated on human samples across different cancer types. The concordance of tumor mutation profiles derived from circulating cell-free DNA with those derived from matched tumor biopsy samples was investigated. Higher than 93% concordance between tumor and cfDNA somatic mutation profiles in both colorectal and melanoma cancers across 14 patients was found (Table 1).

TABLE 1

| Patient ID | Stage | Mutant Genes in Matched Tumor | Percentage of mutant cfDNA |
| --- | --- | --- | --- |
| CRC #1 | II-B | TP53 | 0.2% |
| CRC #2 | II-C | KRAS | 0.6% |
| | | SMAD4 | 1.5% |
| | | GNAS | 1.4% |
| | | FBXW7 | 0.8% |
| CRC #3 | III-B | KRAS | 1.1% |
| | | TP53 | 1.4% |
| | | PIK3CA | 1.7% |
| | | APC | 0.7% |
| CRC #4 | III-B | KRAS | 0.3% |
| | | TP53 | 0.4% |
| CRC #5 | III-B | KRAS | 0.04% |
| CRC #6 | III-C | KRAS | 0.03% |
| CRC #7 | IV | PIK3CA | 1.3% |
| | | KRAS | 0.6% |
| | | TP53 | 0.8% |
| CRC #8 | IV | APC | 0.3% |
| | | SMO | 0.6% |
| | | TP53 | 0.4% |
| | | KRAS | 0.0% |
| CRC #9 | IV | APC | 47.3% |
| | | APC | 40.2% |
| | | KRAS | 37.7% |
| | | PTEN | 0.0% |
| | | TP53 | 12.9% |
| CRC #10 | IV | TP53 | 0.9% |
| Melanoma #1 | IV | BRAF | 0.2% |
| Melanoma #2 | IV | APC | 0.3% |
| | | EGFR | 0.9% |
| | | MYC | 10.5% |
| Melanoma #3 | IV | BRAF | 3.3% |
| Melanoma #4 | IV | BRAF | 0.7% |

It should be understood from the foregoing that, while particular implementations have been illustrated and described, various modifications can be made thereto and are contemplated herein. It is also not intended that the invention be limited by the specific examples provided within the specification. While the invention has been described with reference to the aforementioned specification, the descriptions and illustrations of the preferable embodiments herein are not meant to be construed in a limiting sense. Furthermore, it shall be understood that all aspects of the invention are not limited to the specific depictions, configurations or relative proportions set forth herein which depend upon a variety of conditions and variables. Various modifications in form and detail of the embodiments of the invention will be apparent to a person skilled in the art. It is therefore contemplated that the invention shall also cover any such modifications, variations and equivalents.

What is claimed is:

1. A method for detecting copy number variation, comprising:
   a) attaching a set of molecular barcodes to cell-free nucleic acid molecules obtained or derived from a sample of a subject to produce tagged parent polynucleotides, wherein a plurality of the tagged parent polynucleotides has identical molecular barcodes;
   b) amplifying the plurality of the tagged parent polynucleotides, thereby producing progeny polynucleotides;
   c) sequencing at least a portion of the progeny polynucleotides to generate sequence reads;
   d) mapping the sequence reads derived from the sequencing to a reference sequence to produce mapped reads;
   e) grouping the mapped sequence reads into families, wherein, of the families, a family corresponds to sequence reads of one or more progeny polynucleotides amplified from a same tagged parent polynucleotide of the plurality of the tagged parent polynucleotides;
   f) quantifying numbers of families mapping to predefined regions of the reference sequence; and
   g) determining copy number variation in one or more of the predefined regions from the numbers of families mapping to the predefined regions of the reference sequence.

2. The method of claim 1, wherein the sample is a bodily fluid selected from the group consisting of blood, plasma, and serum.

3. The method of claim 1, wherein the subject has cancer.

4. The method of claim 1, wherein the cell-free nucleic acid molecules comprise circulating tumor DNA.

5. The method of claim 1, further comprising selectively enriching regions from a genome or transcriptome of the subject prior to sequencing.

6. The method of claim 1, wherein, in a) attaching comprises ligating the set of molecular barcodes to the cell-free nucleic acid molecules.

7. The method of claim 1, wherein the set of molecular barcodes comprises between 2 to 1,000,000 different molecular barcodes.

8. The method of claim 7, wherein the set of molecular barcodes comprises between 5 to 100 different molecular barcodes.

9. The method of claim 1, wherein, in a), a molecular barcode is attached to each end of a cell-free nucleic acid molecule.

10. The method of claim 1, wherein a predefined region of the predefined regions is at least a single base.

11. The method of claim 1, wherein a predefined region of the predefined regions comprises at least a portion of a gene.

12. The method of claim 1, wherein the reference sequence is a sequence of a human genome.

13. The method of claim 1, wherein the sample comprises no more than 1% of cell-free nucleic acids from a cancer genome.

14. The method of claim 1, wherein the sample comprises no more than 0.5% of cell-free nucleic acids from a cancer genome.

15. The method of claim 1, wherein the sample comprises no more than 0.1% of cell-free nucleic acids from a cancer genome.

16. The method of claim 1, wherein, in e), grouping mapped sequence reads into families is based on a combination of sequence information from the molecular barcodes and sequence information from a cell-free nucleic acid molecule portion of the progeny polynucleotides.

17. The method of claim 1, wherein the amount of cell-free nucleic acid molecules in the sample is between 10 nanograms (ng) and 100 ng.

18. The method of claim 1, wherein the cell-free nucleic acid molecules are double-stranded deoxyribonucleic acid (DNA).

19. The method of claim 8, wherein the length of the molecular barcodes is at least 5 nucleotides in length.

20. The method of claim 1, further comprising determining a quantity of sequence reads in one or more of the families.

21. The method of claim 1, wherein the predefined regions are overlapping.

22. The method of claim 1, wherein the predefined regions are non-overlapping.

23. The method of claim 1, wherein the numbers of families mapping to the predefined regions are normalized for representational bias during the sequencing process.

24. The method of claim 1, wherein g) comprises normalizing the numbers of families mapping to the predefined regions to each other to determine copy number variation.

25. The method of claim 24, further comprising adjusting the normalized numbers of the families mapping to the predefined regions with a normalized number of families mapping to the predefined regions obtained from at least one control sample.

26. The method of claim 1, wherein g) comprises normalizing the numbers of families mapping to the predefined regions against numbers of families mapping to the predefined regions in at least one control sample.

* * * * *